(12) United States Patent
Sneider et al.

(10) Patent No.: US 12,303,526 B2
(45) Date of Patent: *May 20, 2025

(54) DNA COMPOSITIONS AND RELATED METHODS

(71) Applicant: FLAGSHIP PIONEERING INNOVATIONS VII, LLC, Cambridge, MA (US)

(72) Inventors: Alexandra Rachael Sneider, Cambridge, MA (US); Jacob Rosenblum Rubens, Cambridge, MA (US); Narahari Subbanna Pujar, Berwyn, PA (US); Molly Krisann Gibson, Medford, MA (US); Benjamin Andrew Portney, Somerville, MA (US); Geoffrey A. Von Maltzahn, Somerville, MA (US); Camilo Ayala Breton, Andover, MA (US)

(73) Assignee: FLAGSHIP PIONEERING INNOVATIONS VII, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,813

(22) Filed: Nov. 11, 2022

(65) Prior Publication Data

US 2023/0255999 A1 Aug. 17, 2023

Related U.S. Application Data

(63) Continuation of application No. PCT/US2022/078301, filed on Oct. 18, 2022.

(60) Provisional application No. 63/262,690, filed on Oct. 18, 2021, provisional application No. 63/304,913, filed on Jan. 31, 2022, provisional application No. 63/373,293, filed on Aug. 23, 2022, provisional application No. 63/402,772, filed on Aug. 31, 2022.

(51) Int. Cl.
| | | |
|---|---|---|
| *C12N 15/11* | (2006.01) | |
| *A61K 9/127* | (2006.01) | |
| *A61K 31/7115* | (2006.01) | |
| *A61K 48/00* | (2006.01) | |

(52) U.S. Cl.
CPC .......... *A61K 31/7115* (2013.01); *A61K 9/127* (2013.01); *A61K 48/00* (2013.01); *C12N 15/11* (2013.01); *C12N 2320/30* (2013.01)

(58) Field of Classification Search
CPC ..... A61K 31/7115; A61K 48/00; C12N 15/11
See application file for complete search history.

(56) References Cited

U.S. PATENT DOCUMENTS

| | | | |
|---|---|---|---|
| 6,369,038 B1 | 4/2002 | Blumenfeld et al. | |
| 6,867,028 B2 | 3/2005 | Janulaitis et al. | |
| 8,080,393 B2 | 12/2011 | Koch et al. | |
| 9,109,250 B2 | 8/2015 | Hill | |
| 9,499,847 B2 | 11/2016 | Porter et al. | |
| 10,286,399 B2 | 5/2019 | Porter et al. | |
| 10,501,782 B1 | 12/2019 | Porter et al. | |
| 11,149,302 B2 | 10/2021 | Rothwell et al. | |
| 11,339,442 B2 | 5/2022 | Bernstein et al. | |
| 11,384,388 B2 | 7/2022 | Hill | |
| 11,446,393 B2 | 9/2022 | Pouton et al. | |
| 2008/0305142 A1 | 12/2008 | Chen et al. | |
| 2008/0305535 A1 | 12/2008 | Auerbach | |
| 2010/0055744 A1 | 3/2010 | Nelson et al. | |
| 2016/0008815 A1 | 1/2016 | Porter et al. | |
| 2018/0037943 A1 | 2/2018 | Rothwell et al. | |
| 2018/0185516 A1 | 7/2018 | Ansell et al. | |
| 2018/0305701 A1* | 10/2018 | Zechiedrich | C12N 15/10 |
| 2019/0185924 A1 | 6/2019 | Adie et al. | |
| 2019/0211361 A1* | 7/2019 | Kahvejian | C12N 15/86 |
| 2019/0270991 A1* | 9/2019 | Foot | C12N 15/11 |
| 2020/0224220 A1 | 7/2020 | Finer et al. | |
| 2021/0139971 A1 | 5/2021 | Deng et al. | |
| 2021/0147869 A1 | 5/2021 | Karbowniczek et al. | |
| 2021/0269828 A1 | 9/2021 | Samulski | |
| 2021/0301312 A1 | 9/2021 | Porter et al. | |
| 2021/0346306 A1 | 11/2021 | Dimitrov et al. | |
| 2022/0127667 A1 | 4/2022 | Rothwell et al. | |
| 2022/0168222 A1 | 6/2022 | Heyes et al. | |
| 2022/0175968 A1 | 6/2022 | Stanton et al. | |

(Continued)

FOREIGN PATENT DOCUMENTS

| | | |
|---|---|---|
| WO | 1992/001813 A1 | 2/1992 |
| WO | 2000/015779 A2 | 3/2000 |

(Continued)

OTHER PUBLICATIONS

Duan et al, Circular Intermediates of Recombinant Adeno-Associated Virus Have Defined Structural Characteristics Responsible for Long-Term Episomal Persistence in Muscle Tissue, Journal of Virology, 1998, vol. 72, No. 11, pp. 8568-8577 (Year: 1998).*
International Search Report and Written Opinion in International Patent Application No. PCT/US2022/078301 mailed Feb. 23, 2023.
Zhang, P. et al. "Engineering BspQI nicking enzymes and application of N.BspQI in DNA labeling and production of single-strand DNA," Protein Expression and Purification (2010) vol. 69, No. 2, pp. 226-234.
Ford, A. et al. "Generating single-stranded DNA circles with minimal resources," MethodsX (2021) vol. 8, 1011300.

(Continued)

*Primary Examiner* — Ekaterina Poliakova-Georgantas
(74) *Attorney, Agent, or Firm* — K&L Gates LLP

(57) ABSTRACT

The disclosure provides, for example, single stranded, covalently closed DNA that does not form a double stranded structure longer than 100 base pairs. The ssDNA may encode an effector sequence, for instance a therapeutic protein. The ssDNA may comprise a nuclear targeting sequence (NTS). In some embodiments, the ssDNA shows decreased activation of the innate immune system compared to an otherwise similar dsDNA.

22 Claims, 23 Drawing Sheets

Specification includes a Sequence Listing.

(56) References Cited

U.S. PATENT DOCUMENTS

| | | |
|---|---|---|
| 2022/0177545 A1 | 6/2022 | Kerr et al. |
| 2022/0195415 A1 | 6/2022 | Adie et al. |
| 2022/0228171 A1 | 7/2022 | Alkan et al. |
| 2022/0290186 A1 | 9/2022 | Kotin et al. |
| 2022/0296517 A1 | 9/2022 | Benenato et al. |

FOREIGN PATENT DOCUMENTS

| | | | |
|---|---|---|---|
| WO | 2010094040 A1 | 8/2010 | |
| WO | WO-2012123430 A1 * | 9/2012 | ............... A61P 21/00 |
| WO | WO-2019051255 A1 * | 3/2019 | ............ A61K 48/005 |
| WO | 2019/089828 A1 | 5/2019 | |
| WO | 2019/094725 A2 | 5/2019 | |
| WO | 2019/118806 A1 | 6/2019 | |
| WO | 2020123795 A2 | 6/2020 | |
| WO | 2021011840 A1 | 1/2021 | |
| WO | 2021/119585 A1 | 6/2021 | |
| WO | 2021/161051 A1 | 8/2021 | |
| WO | 2021/178709 A1 | 9/2021 | |
| WO | 2021/178725 A1 | 9/2021 | |
| WO | 2021/195214 A1 | 9/2021 | |
| WO | 2021/202397 A2 | 10/2021 | |
| WO | 2021/247507 A1 | 12/2021 | |
| WO | 2021/252354 A1 | 12/2021 | |
| WO | 2021/257830 A1 | 12/2021 | |
| WO | 2022/069577 A1 | 4/2022 | |
| WO | 2022/094238 A2 | 5/2022 | |
| WO | 2022/133246 A1 | 6/2022 | |
| WO | 2022/198025 A2 | 9/2022 | |

OTHER PUBLICATIONS

Iyer, S. et al. "Efficient Homology-Directed Repair with Circular Single-Stranded DNA Donors," The CRISPR Journal (2022) vol. 5, 5, pp. 685-701, doi: 10.1089/crispr.2022.0058 (Epub Sep. 7, 2022).

Lin-Shiao, E. et al. "CRISPR-Cas9 mediated nuclear transport and genomic integration of nanostructured genes in human primary cells," bioRxiv preprint doi: https://doi.org/10.1101/2021.11.08.467750 Nov. 9, 2021.

Lin-Shiao, E. et al. "CRISPR-Cas9-mediated nuclear transport and genomic integration of nanostructured genes in human primary cells," Nucleic Acids Research (2022) vol. 50, 3, pp. 1256-1268.

Shepherd, T. R. et al. "Bioproduction of pure, kilobase-scale single-stranded DNA," Scientific Reports (2019) vol. 9, 6121.

Shy, B. R. et al. "Hybrid ssDNA repair templates enable high yield genome engineering in primary cells for disease modeling and cell therapy manufacturing," bioRxiv preprint doi: https://doi.org/10.1101/2021.09.02.458799 Sep. 4, 2021.

Shy, B. R. et al. "High-yield genome engineering in primary cells using a hybrid ssDNA repair template and small-molecule cocktails," Nature Biotechnology (2022).

Thermo Scientific Protocol. "Production of Single-stranded Circular DNA Molecules from Supercoiled Double-stranded Plasmids in vitro" (2012).

U.S. Department of Health and Human Services. "Chemistry, Manufacturing, and Control (CMC) Information for Human Gene Therapy Investigational New Drug Applications (INDs): Guidance for Industry," (2020) pp. 1-56.

U.S. National Phase U.S. Appl. No. 18/702,197, filed Apr. 17, 2024.

"PCR & Reaction Cleanup." New England Biolabs (<https://www.neb.com/en-gb/applications/dna-amplification-pcr-and-qpcr/pcr-and-reaction-cleanup>) n.d. Retrieved Feb. 16, 2024.

Barbier, F.F. et al. "A phenol/chloroform-free method to extract nucleic acids from recalcitrant, woody tropical species for gene expression and sequencing." Plant methods vol. 15, 62 (2019).

Chan, Siu-Hong et al. "Natural and engineered nicking endonucleases—from cleavage mechanism to engineering of strand-specificity." Nucleic Acids Research vol. 39,1 (2011): 1-18. Epub Aug. 30, 2010.

Zhao, Y. and Huang, L. "Chapter 2—Lipid nanoparticles for gene delivery." Advances in Genetics vol. 88 (2014): 13-36.

Sahin et al. "mRNA-based therapeutics—developing a new class of drugs." Nature Reviews. Drug Discovery vol. 3 (2014): 759-80.

Third Party Observation received in International Patent Application No. PCT/US2022/078301 submitted Feb. 16, 2024.

* cited by examiner

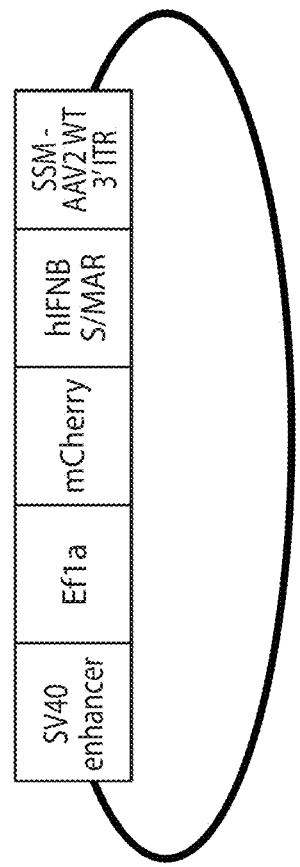
FIG. 1C
FIG. 1D
FIG. 1E

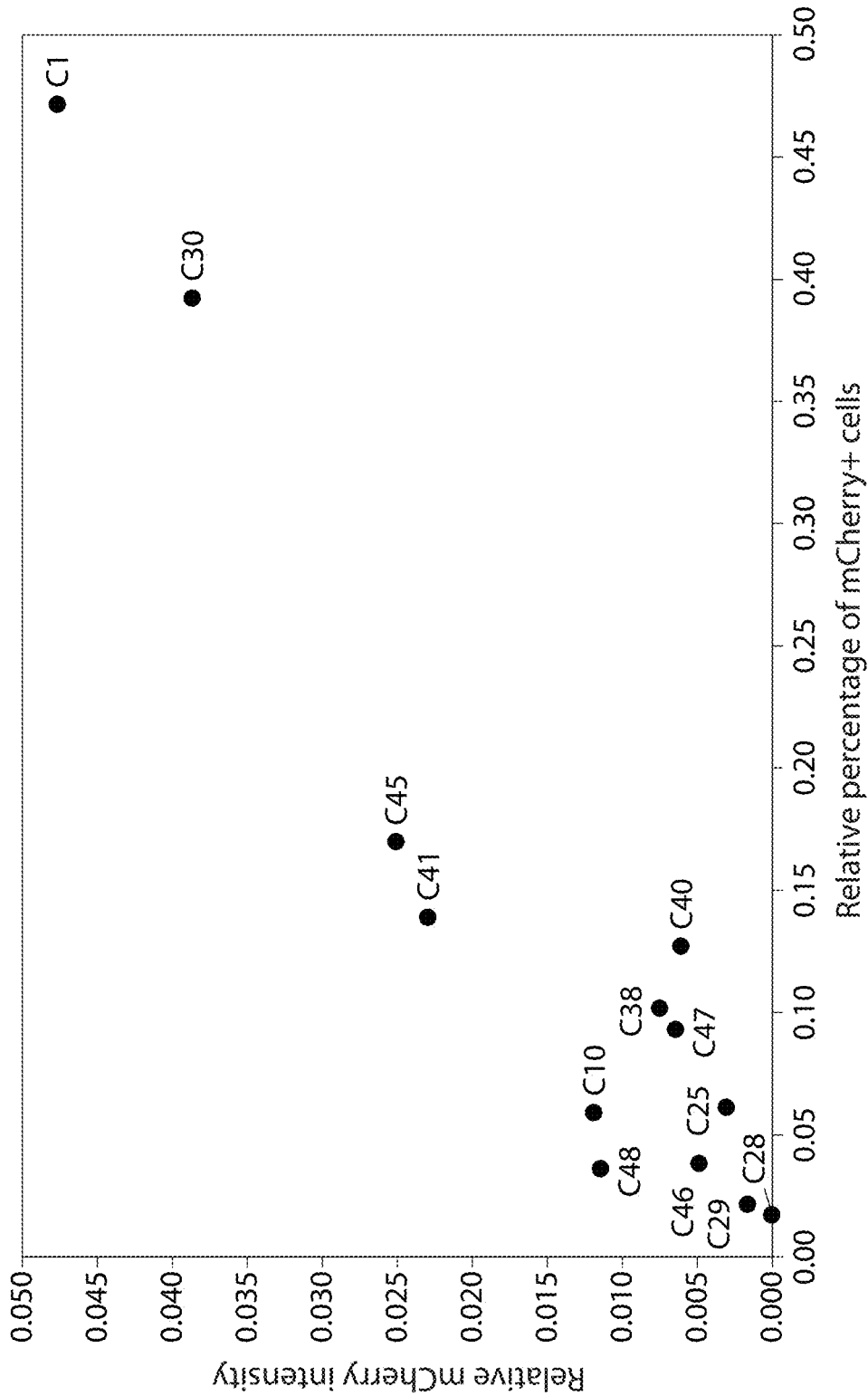

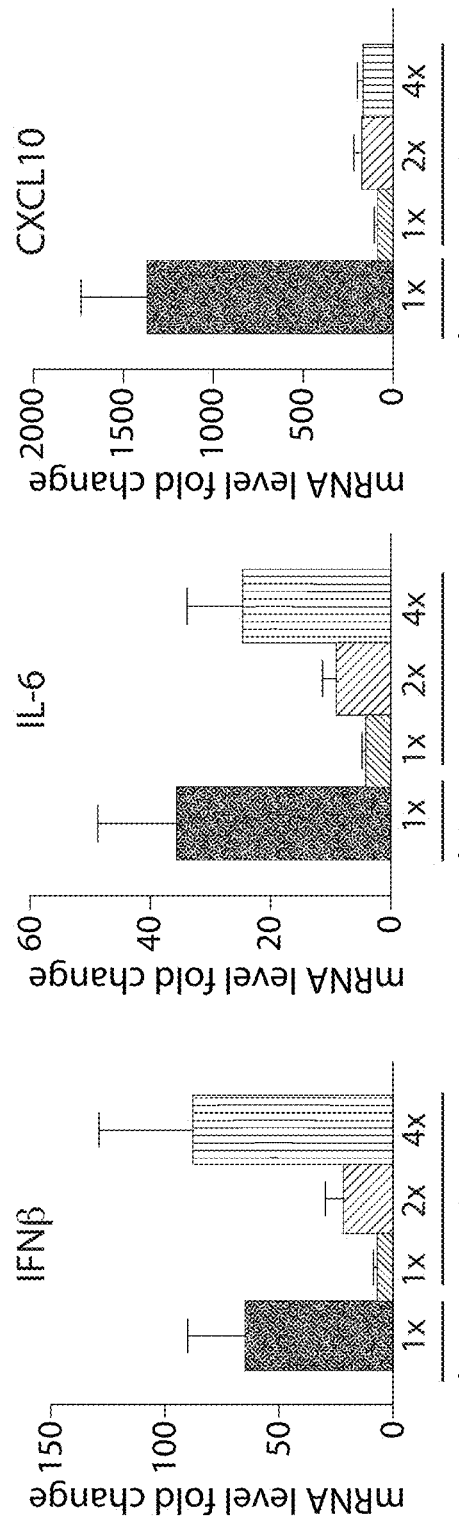
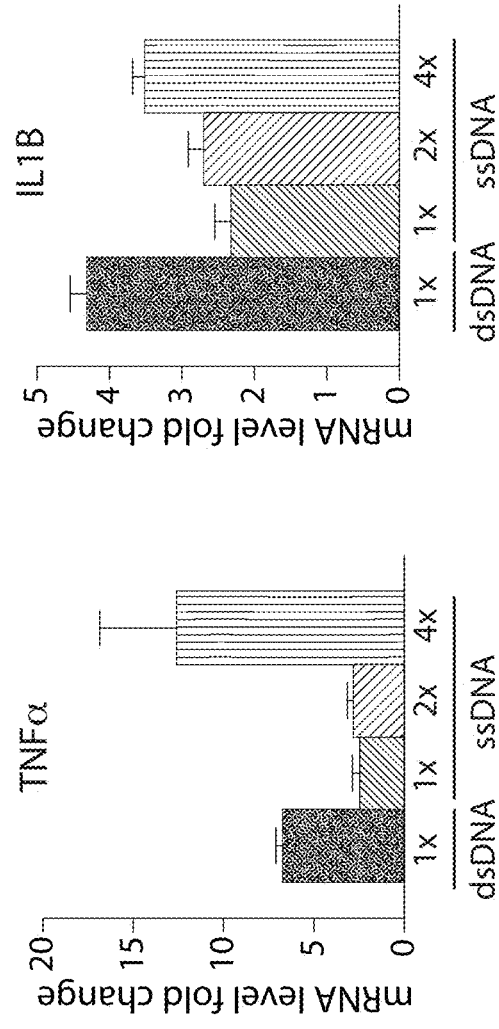
FIG. 14A  FIG. 14B  FIG. 14C  FIG. 14D  FIG. 14E

DNA COMPOSITIONS AND RELATED METHODS

CROSS-REFERENCE TO RELATED APPLICATIONS

This application is a Continuation of International Patent Application No. PCT/US2022/078301, filed Oct. 18, 2022, which claims priority to U.S. Provisional Patent Application Ser. No. 63/262,690, filed Oct. 18, 2021, U.S. Provisional Patent Application Ser. No. 63/304,913, filed Jan. 31, 2022, U.S. Provisional Patent Application Ser. No. 63/373,293, filed Aug. 23, 2022, and U.S. Provisional Patent Application Ser. No. 63/402,772, filed Aug. 31, 2022, the entire contents of each of which is incorporated herein by reference.

SEQUENCE LISTING

The instant application contains a Sequence Listing which has been submitted electronically in XML format and is hereby incorporated by reference in its entirety. Said XML copy, created on Mar. 28, 2023, is named F2128-700020FT_VL87001-US_SL.xml and is 65,197 bytes in size.

BACKGROUND

There is a need for novel therapeutic modalities to address unmet medical need.

SUMMARY OF THE INVENTION

Described herein are pharmaceutical DNA compositions, constructs, preparations, methods of using such compositions, constructs and preparations, and methods of making the same.

In some aspects, the present disclosure provides a pharmaceutical formulation comprising: an LNP comprising a single stranded DNA (ssDNA), wherein the ssDNA: (a) encodes a therapeutic protein, (b) is covalently closed, (c) does not form a double stranded structure longer than 100 base pairs, (d) is more than 200 nucleotides in length, and (e) does not comprise a protelomerase target sequence; wherein the pharmaceutical formulation is substantially free of linear DNA and protein. In some embodiments, the ssDNA does not form a double stranded structure longer than 40 base pairs.

In some embodiments, the ssDNA comprises a promoter sequence operably linked to a sequence encoding the therapeutic polypeptide. In some embodiments, the therapeutic protein is selected from the group consisting of: a transcription factor, a chromatin remodeling factor, an antigen, a peptide, a hormone, an enzyme, an antibody, a receptor ligand, a receptor, a clotting factor, and a membrane protein. In some embodiments, the ssDNA has a GC content of 30-40%, 40-50%, 50-60%, or 60-70%.

In some embodiments, the ssDNA lacks one or both of a bacteriophage packaging site and a bacteriophage origin of replication, or wherein the ssDNA does not encode a bacteriophage capsid gene. In some embodiments, the ssDNA was not produced by rolling circle amplification. In some embodiments, the ssDNA was not produced by strand displacement amplification.

In some embodiments, the ssDNA further comprises a nuclear targeting sequence (NTS). In some embodiments, the ssDNA further comprises a maintenance sequence. In some embodiments, the ssDNA further comprises a second strand motif (SSM).

In some embodiments, the ssDNA comprises between 200-3,000 nucleotides. In some embodiments, the ssDNA comprises between 500 and 2,000 nucleotides. In some embodiments, the ssDNA is a sense ssDNA strand. In some embodiments, the ssDNA is an antisense ssDNA strand.

In some embodiments, the ssDNA comprises at least one nucleotide modification. In some embodiments, the nucleotide modification is 5-formylcytosine.

In some embodiments, the pharmaceutical formulation is formulated for parenteral administration. In some embodiments, the pharmaceutical formulation is formulated for topical administration. In some embodiments, the pharmaceutical formulation is substantially free of one or more of: endotoxin, mononucleotides, modified mononucleotides, double stranded DNA.

In some aspects, the present disclosure provides a method of delivering a therapeutic protein to a subject, comprising administering to the subject a pharmaceutical formulation described herein. In some embodiments, the method does not result in substantial integration of the ssDNA into the genome of the subject.

In one aspect the invention features a composition, e.g., a pharmaceutical composition, that includes a single stranded DNA (ssDNA) comprising an effector sequence, the single stranded DNA having one, two or three of the following characteristics: the ssDNA is covalently closed; the ssDNA does not form a double stranded structure longer than 100 base pairs; the ssDNA comprises at least one covalent modification.

In an embodiment, the ssDNA has an effector sequence and one, two or three of: a nuclear targeting sequence (NTS), a maintenance sequence, and a second strand motif (SSM). In one embodiment the ssDNA has a DNA effector sequence. In one embodiment, the ssDNA has a DNA effector sequence and an NTS. In one embodiment, the ssDNA has a DNA effector sequence, an NTS, and a SSM. In one embodiment, the ssDNA has a DNA effector sequence, an NTS, a SSM and a maintenance sequence. In one embodiment, the ssDNA has a DNA effector sequence, an NTS, and a maintenance sequence. In one embodiment, the ssDNA has a DNA effector sequence, an SSM and a maintenance sequence. In one embodiment, the ssDNA has a promoter operably linked to a sequence encoding an RNA or protein (peptide or polypeptide) effector. In one embodiment, the ssDNA has a promoter operably linked to a sequence encoding an RNA or protein (peptide or polypeptide) effector, and an NTS. In one embodiment, the ssDNA has a promoter operably linked to a sequence encoding an RNA or protein (peptide or polypeptide) effector, an NTS, and a SSM. In one embodiment, the ssDNA has a promoter operably linked to a sequence encoding an RNA or protein (peptide or polypeptide) effector, an NTS, a SSM and a maintenance sequence. In one embodiment, the ssDNA has a promoter operably linked to a sequence encoding an RNA or protein (peptide or polypeptide) effector, an NTS, and a maintenance sequence. In one embodiment, the ssDNA has a promoter operably linked to a sequence encoding an RNA or protein (peptide or polypeptide) effector, an SSM and a maintenance sequence. In some embodiments, a ssDNA described herein comprises an enhancer, e.g., an SV40 enhancer. In some embodiments, a ssDNA comprises two enhancers. In some embodiments, one or both of the enhancers is an SV40 enhancer. In some embodiments, a ssDNA described herein comprises a NTS, e.g., an NTS that binds a transcription factor, e.g., an NTS that binds NF-κB, e.g., a 3NF sequence. In some embodiments, a ssDNA comprises two, three, or four NTSs. In some embodiments, 1, 2, 3, or 4 of the NTSs is a 3NF sequence. In some embodiments, a ssDNA described herein comprises a SMM (e.g., an Anellovirus hairpin). In some embodiments, a ssDNA described herein comprises a polyA signal, e.g., a bGH polyA signal. In some embodiments, a ssDNA described herein comprises a promoter, e.g., an EF1a promoter.

In some embodiments, the enhancer is situated upstream of the promoter. The NTS may be situated, for example, upstream of the promoter or downstream of the polyA signal. In some embodiments, the SMM (e.g., Anellovirus hairpin) is situated upstream of the promoter.

In some embodiments, the promoter is situated between the enhancer and the effector sequence. In some embodiments, the NTS is situated between the SMM (e.g., anellovirus hairpin) and the promoter. In some embodiments, the SMM (e.g., anellovirus hairpin) is situated between the enhancer and the promoter. In some embodiments, the polyA signal is situated between the effector sequence and the NTS. In some embodiments, the polyA signal is situated between the effector sequence and the enhancer. In some embodiments, the polyA signal is situated between the SMM (e.g., anellovirus hairpin) and the effector sequence. In some embodiments, the NTS is situated between the SMM (e.g., anellovirus hairpin) and the polyA signal. In some embodiments, a first NTS sequence is immediately adjacent to a second NTS sequence. In some embodiments, a ssDNA described herein comprises a series of components arranged as shown in Table 5 herein.

In an embodiment, the ssDNA has at least 15 nucleotides, at least 30 nucleotides, at least 50 nucleotides, at least 75 nucleotides, 100 nucleotides, at least 200 nucleotides, at least 300 nucleotides, at least 500 nucleotides, at least 750 nucleotides, at least 1,000 nucleotides, at least 2,000 nucleotides, at least 3,000 nucleotides, at least 4,000 nucleotides, at least 5,000 nucleotides, at least 10,000 nucleotides, at least 15,000 nucleotides, at least 20,000 nucleotides, at least 25,000 nucleotides, at least 30,000 nucleotides, at least 35,000 nucleotides, at least 40,000 nucleotides at least 45,000 nucleotides, at least 50,000 nucleotides, at least 60,000 nucleotides, or more.

In an embodiment, the ssDNA has between 20 and 1000 nucleotides, between 20 and 50 nucleotides, between 100 and 500 nucleotides, between 500 and 50,000 nucleotides, between 1,000 and 50,000 nucleotides, between 2,000 and 40,000 nucleotides, between 5,000 and 50,000 nucleotides, between 500 and 50,000 nucleotides, between 500 and 25,000 nucleotides, between 1,000 and 20,000 nucleotides, between 1,000 and 10,000 nucleotides, between 10,000 and 60,000 nucleotides, between 1,000 and 20,000 nucleotides, between 1,000 and 40,000 nucleotides, between 200 and 1,000 nucleotides, between 200 and 2,000 nucleotides, between 200 and 3,000 nucleotides, between 500 and 1,000 nucleotides, between 500 and 2,000 nucleotides, between 500 and 3,000 nucleotides, between 1,000 and 2,000 nucleotides, between 1,000 and 3,000 nucleotides, or between 2,000 and 3,000 nucleotides. In some embodiments, the ssDNA comprises between 20-20,000 nucleotides. In some embodiments the ssDNA comprises between 50-50,000 nucleotides.

In an embodiment, the ssDNA is a sense ssDNA strand. In an embodiment, the ssDNA is an antisense ssDNA strand.

In an embodiment, the ssDNA comprises at least one nucleotide modification, e.g., a covalent nucleotide modification, e.g., selected from: N6-Methyladenosine (m6A, 6 mA); 5-Formylcytosine (5fC, f5C); 5-carboxylcytosine (ca5C, 5caC); 5-hydroxymethylcytosine (5hmC, hm5C); 5-methyldeoxycytosine (m5dC); 5-methylcytosine (5mC, m5C); 5'-methylcytosine; 3-methylcytosine (m3C); 5-methyl pyrimidine; 8-oxoguanine (8-oxoG); phosphorothioate; S and R phsophorothioate linkages; methylthymine; N3'-P5' Phosphoroamidate (NP); cyclohexane nucleic acid (CeNA); and tricyclo-DNA (tcDNA). In some embodiments, the ssDNA comprises $N^6$-methyladenosine. In some embodiments, the majority of A positions in the ssDNA are $N^6$-methyladenosine. In some embodiments, the nucleotide modification is a covalent modification selected from phosphothioate; borano-phosphate; 1,5-disubstituted triazole; 2'-fluoro-2'deoxynucleoside 5'-triphosphate; and 7-mehtylguanine; 5-glucosylmethylcytosine.

In some embodiments, the nucleotide modification is a base modification. In some embodiments, the nucleotide modification is a backbone modification. In some embodiments, the nucleotide modification is a sugar modification. In some embodiments, the nucleotide modification comprises a peptide conjugate. In some embodiments, the nucleotide modification comprises a protein conjugate.

In an embodiment, the effector sequence is a therapeutically functional sequence, e.g., a functional, structural DNA sequence such as a DNA aptamer, DNAzyme or allele-specific oligonucleotide (ASO).

In an embodiment, the effector sequence is a DNA sequence encoding a therapeutic (e.g., regulatory) RNA, operably linked to a promoter. In an embodiment, the RNA can be, e.g., a tRNA, lncRNA, miRNA, rRNA, snRNA, microRNA, siRNA, piRNA, snoRNA, exRNA, scaRNA, Y RNA, or hnRNA.

In some embodiments, the therapeutically functional sequence comprises a promoter sequence operably linked to a sequence encoding a therapeutic RNA or polypeptide. In an embodiment, the effector sequence is a DNA sequence encoding a therapeutic peptide or polypeptide, operably linked to a promoter. The therapeutic peptide or polypeptide may be, e.g., a DNA binding protein; an RNA binding protein; a transporter; a transcription factor; a translation factor; a ribosomal protein; a chromatin remodeling factor; an epigenetic modifying factor; an antigen; a hormone; an enzyme (such as a nuclease, e.g., an endonuclease, e.g., a nuclease element of a CRISPR system, e.g., a Cas9, dCas9, aCas9-nickase, Cpf/Cas12a); a Crispr-linked enzyme, e.g., a base editor or prime editor; a mobile genetic element protein (e.g., a transposase, a retrotransposase, a recombinase, an integrase); a gene writer; a polymerase; a methylase; a demethylase; an acetylase; a deacetylase; a kinase; a phosphatase; a ligase; a deubiquitinase; a protease; an integrase; a recombinase; a topoisomerase; a gyrase; a helicase; a lysosomal acid hydrolase; an antibody (e.g., an intact antibody, a fragment thereof, or a nanobody); a signaling peptide; a receptor ligand; a receptor; a clotting factor; a coagulation factor; a structural protein; a caspase; a membrane protein; a mitochondrial protein; a nuclear protein; a protein scaffold binder such as a centyrin, darpin, or adnectin.

In embodiments, the ssDNA can include a plurality of effector sequences. The plurality may be the same or different types, e.g., a ssDNA can include an effector sequence that is a structural DNA and a second effector sequence that is a DNA sequence encoding a functional RNA or polypeptide. In some embodiments, the ssDNA comprises a second effector sequence which is the same as or different than the first effector sequence. A ssDNA can include an effector sequence that is a DNA sequence encoding a functional RNA and a second effector sequence that is a DNA sequence encoding a functional polypeptide. The plurality of effector sequences may be the same or different sequences of the same type.

In some embodiments, when the ssDNA is introduced to a cell, the cell exhibits a lower cytokine mRNA level increase (e.g., normalized to GAPDH mRNA levels) compared to a control cell of the same type that was contacted with a dsDNA having the same sequence as the ssDNA at the same molar amount as the ssDNA. In some embodiments, the cytokine comprises cytokine IFN-b, IL-6, IL-1b, TNF-α, or CXCL10. In some embodiments, the cytokine increase in the control cells is less than 50%, 40%, 30%, 20%, or 10% of the cytokine increase in the control cells.

In some embodiments, a ssDNA described herein has an A260/A280 ratio of 1.6-1.7, 1.7-1.8. or 1.63-1.76. In some embodiments, a ssDNA described herein has an A230/A260 ratio of 0.3-1, 1-1.5, 1.5-1.8, or 0.34-1.79.

In embodiments, the ssDNA is not disposed in a carrier, e.g., it is formulated for naked administration.

In embodiments, the ssDNA is formulated with a carrier, e.g., a lipid-based carrier, e.g., an lipid nanoparticle (LNP). In embodiments, the pharmaceutical composition further comprises a carrier, e.g., a lipid-based carrier, e.g., an LNP.

In some embodiments, the composition comprising ssDNA is substantially free of (e.g., is free of) an LNP. In some embodiments, the composition comprising ssDNA is substantially free of (e.g., is free of) a lipid-based carrier. In some embodiments, the composition comprising ssDNA is substantially free of (e.g., is free of) a lipid.

In embodiments, the ssDNA is formulated with a pharmaceutical excipient.

In embodiments, the ssDNA is formulated for parenteral administration.

In embodiments, the pharmaceutical composition is formulated for topical administration.

In embodiments, the pharmaceutical composition is substantially free of impurities or process byproducts, e.g., selected from the group consisting of: endotoxin, mononucleotides, modified mononucleotides, double-stranded DNA, DNA fragments or truncations, and proteins (e.g., enzymes, e.g., ligases, restriction enzymes). In the case of circular, e.g., covalently closed, ssDNA, the pharmaceutical composition is substantially free of linear DNA.

In any embodiment described herein, the ssDNA may be covalently closed, e.g., the ssDNA is circularized.

In another aspect, the invention includes a method of delivering an effector to a subject, e.g., a subject in need thereof. The method incudes administering to the subject a composition described herein, e.g., described in any embodiment above. In an embodiment, the subject has or has been diagnosed with a condition that can be treated with the effector.

In another aspect, the invention includes a method of modulating (e.g., increasing or decreasing) a biological parameter in a cell, tissue or subject. The method incudes administering to the subject a composition described herein, e.g., described in any embodiment above. In embodiments, the biological parameter is an increase or decrease in gene expression of a subject gene in a target cell, tissue or subject, which increase or decrease is effected by an effector sequence described herein. In an embodiment, the subject has or has been diagnosed with a condition that can be treated with the effector.

In another aspect, the invention includes a method of treating a cell, tissue or subject. The method includes administering to a cell, tissue or subject in need thereof an ssDNA or construct described herein, e.g., described in any embodiment above. In an embodiment, the subject has or has been diagnosed with a condition that can be treated with the effector.

In another aspect, the invention features a method of making a pharmaceutical composition that includes a ssDNA comprising an effector sequence. The method comprises: (a) providing or generating a plasmid comprising an effector sequence and, optionally, one or more of (e.g., 2, 3, or 4 of) a promoter operably linked to the effector sequence, an NTS, a SSM and a maintenance sequence, (b) providing or generating a ssDNA comprising the effector sequence and, optionally, one or more of (e.g., 2, 3, or 4 of) a promoter operably linked to the effector sequence, an NTS, a SSM and a maintenance sequence, using the plasmid as a template, and (c) optionally, circularizing the ssDNA.

In one embodiment, the method comprises circularizing (e.g., ligating the ends of) the ssDNA.

In embodiments the ssDNA is any ssDNA described herein, e.g., described in any embodiment above.

In an embodiment, step (a) comprises performing golden gate assembly of the recited sequence elements.

In an embodiment, the method further comprises (d) enriching or purifying the ssDNA made in step (b) or the circularized, e.g., covalently closed, ssDNA made in step (c).

In an embodiment, step (d) includes substantially removing from the ssDNA one or more impurity selected from: endotoxin, mononucleotides, modified mononucleotides, double stranded DNA, DNA fragments or truncations, and proteins (e.g., enzymes, e.g., ligases, restriction enzymes). In the case of circular, e.g., covalently closed, ssDNA, linear DNA is removed.

In an embodiment, the method further comprises formulating the enriched or purified ssDNA or circularized ssDNA of step (d) for pharmaceutical use, e.g., formulating the enriched or purified ssDNA or circularized, e.g., covalently closed, ssDNA with a pharmaceutically acceptable excipient and/or with a carrier, e.g., an LNP.

In another aspect, the invention features a plasmid comprising an effector sequence described herein and 1, 2, 3, or 4 of the following elements: a promoter, a NTS, a SSM, and a maintenance sequence.

In some aspects, the disclosure provides a composition (e.g., a pharmaceutical composition) comprising: a covalently closed, single stranded DNA (ssDNA) comprising an effector sequence, wherein one or more of: a) at least 70%, 80%, 85%, 90%, 95%, 96%, 97%, or 98%, or 99% by mass of total DNA in the composition is the covalently closed ssDNA; b) at least 70%, 80%, 85%, 90%, 95%, 96%, 97%, 98%, or 99% by mass of total DNA in the composition is full length; c) less than 10%, 5%, 4%, 3%, 2%, or 1% by mass of DNA in the composition is double stranded DNA (dsDNA); d) less than 10%, 5%, 4%, 3%, 2%, or 1% by mass of DNA in the composition is linear DNA; or e) less than 10%, 5%, 4%, 3%, 2%, or 1% by mass of DNA in the composition is linear ssDNA.

In some aspects, the disclosure provides a composition (e.g., a pharmaceutical composition) comprising: a covalently closed, single stranded DNA (ssDNA) comprising an effector sequence, wherein one or more of: a) the composition is substantially free of, e.g., is free of, chloroform; b) the composition is substantially free of, e.g., is free of, phenol; c) the composition is substantially free of, e.g., is free of, phenol and chloroform; d) the composition is substantially free of, e.g., is free of, organic solvents; or e) the composition is substantially free of, e.g., is free of, aromatic organic solvents.

In some aspects, the disclosure provides a composition (e.g., a pharmaceutical composition) comprising: a covalently closed, single stranded DNA (ssDNA) comprising an effector sequence, wherein the ssDNA was produced by a method that does not comprise a phenol-chloroform extraction step.

In some aspects, the disclosure provides a composition (e.g., a pharmaceutical composition) comprising: a covalently closed, single stranded DNA (ssDNA) comprising an effector sequence, wherein one or more of: a) the composition is substantially free of (e.g., is free of) Exonuclease III; b) the composition is substantially free of (e.g., is free of) T7 Exonuclease; or c) the composition is substantially free of (e.g., is free of) T5 Exonuclease.

In some aspects, the disclosure provides a composition (e.g., a pharmaceutical composition) comprising at least 1, 2, 3, 4, 5, 6, 7, 8, 9, or 10 mg of a covalently closed, single stranded DNA (ssDNA) comprising an effector sequence.

In some aspects, the disclosure provides a composition (e.g., a pharmaceutical composition or a manufacturing intermediate) comprising: a circular double stranded DNA comprising an effector sequence and comprising at least one modified nucleotide, and Nb.BsrDI or Nt.BspQI.

In some embodiments, the ssDNA is not disposed in a carrier. In some embodiments, the composition further comprises a carrier. In some embodiments, the carrier is a lipid-based carrier. In some embodiments, the lipid-based carrier is a lipid nanoparticle (LNP). In some embodiments, the composition is formulated for naked administration. In some embodiments, the composition is formulated for parenteral administration. In some embodiments, the composition is formulated for topical administration. In some embodiments, the composition is substantially free of impurities or byproducts selected from the group consisting of: endotoxin, mononucleotides, modified mononucleotides, double stranded DNA, DNA fragments or truncations, proteins (e.g., enzymes, e.g., ligases, restriction enzymes).

In some aspects, the disclosure provides a method of making a circular, ssDNA, the method comprising: a) providing (e.g., producing or obtaining) a circular dsDNA, wherein the circular dsDNA: i) lacks a plasmid backbone; ii) lacks a bacterial origin of replication; iii) lacks a selectable marker, e.g., an antibiotic resistance marker; and/or iv) comprises a chemical modification, e.g., a chemical modification to a sugar, a chemical modification to a base, or a chemical modification to a nucleic acid backbone; b) introducing a discontinuity into one strand of the circular dsDNA (e.g., contacting the circular dsDNA with a nicking endonuclease (e.g., Nb.BsrDI or Nb.Bpu10I or Nt.BspQI) that recognizes a nicking recognition site in the dsDNA under conditions that allow the nicking endonuclease to nick the site in the dsDNA) thereby producing a dsDNA having a discontinuity; c) contacting the dsDNA having the discontinuity with an exonuclease (e.g., T7 exonuclease or Exonuclease III) under conditions that allow for degradation (e.g., complete degradation) of the nicked strand, thereby making the circular, ssDNA.

In some aspects, the disclosure provides a method of making a circular, ssDNA, the method comprising: a) providing (e.g., producing or obtaining) a circular dsDNA; b) contacting the circular dsDNA with a nicking endonuclease chosen from Nb.BsrDI or Nt.BspQI that recognizes a nicking recognition site in the dsDNA under conditions that allow the nicking endonuclease to nick the site in the dsDNA, thereby producing a nicked dsDNA; c) contacting the nicked dsDNA with an exonuclease (e.g., T7 exonuclease or Exonuclease III) under conditions that allow for degradation (e.g., complete degradation) of the nicked strand, thereby making the circular, ssDNA.

In some aspects, the disclosure provides a method of making a circular, ssDNA, the method comprising: a) providing (e.g., producing or obtaining) a circular dsDNA; b) introducing a discontinuity into one strand of the circular dsDNA (e.g., contacting the circular dsDNA with a nicking endonuclease (e.g., Nb.BsrDI or Nb.Bpu10I or Nt.BspQI) that recognizes a nicking recognition site in the dsDNA under conditions that allow the nicking endonuclease to nick the site in the dsDNA), thereby producing a nicked dsDNA having a discontinuity; c) contacting the nicked dsDNA with a T7 exonuclease under conditions that allow for degradation (e.g., complete degradation) of the nicked strand, thereby making the circular, ssDNA.

In some aspects, the disclosure provides a method of making a circular, ssDNA, the method comprising: a) providing (e.g., producing or obtaining) a circular dsDNA; b) introducing a discontinuity into one strand of the circular dsDNA (e.g., contacting the circular dsDNA with a nicking endonuclease (e.g., Nb.BsrDI or Nb.Bpu10I or Nt.BspQI) that recognizes a nicking recognition site in the dsDNA under conditions that allow the nicking endonuclease to nick the site in the dsDNA), thereby producing a nicked dsDNA having a discontinuity; c) contacting the nicked dsDNA with an exonuclease (e.g., T7 exonuclease or Exonuclease III) under conditions that allow for degradation (e.g., complete degradation) of the nicked strand, thereby making a circular, ssDNA, and d) performing gel purification on the circular, ssDNA.

In some embodiments, the circular dsDNA: i) lacks a plasmid backbone; ii) lacks a bacterial origin of replication; iii) lacks a selectable marker, e.g., an antibiotic resistance marker; and/or iv) comprises a chemical modification, e.g., a chemical modification to a sugar, a chemical modification to a base, or a chemical modification to a nucleic acid backbone.

In some embodiments, the method comprises contacting the circular dsDNA with a nicking endonuclease chosen from Nb.BsrDI or Nt.BspQI that recognizes a nicking recognition site in the dsDNA under conditions that allow the nicking endonuclease to nick the site in the dsDNA, thereby producing a nicked dsDNA. In some embodiments, the method comprises contacting the nicked dsDNA with a T7 exonuclease under conditions that allow for degradation (e.g., complete degradation) of the nicked strand. In some embodiments, the method comprises performing gel purification on the circular, ssDNA.

In some embodiments, the method comprises producing circular dsDNA, wherein producing the circular dsDNA comprises one or more of (e.g., 2, 3, 4, or all of): (i) providing a nucleic acid (e.g., a plasmid) comprising an effector sequence; (ii) performing PCR to amplify a region of the nucleic acid (e.g., plasmid) that comprises the effector sequence, wherein performing PCR comprises contacting the plasmid with a first primer comprising a first endonuclease recognition site and a second primer comprising a second endonuclease recognition site and a nicking recognition site, wherein the first primer and the second primer are positioned at locations on the plasmid suitable to amplify the effector sequence (and optionally, not amplify backbone of the plasmid), and contacting the plasmid with a DNA-dependent DNA polymerase (e.g., a high fidelity polymerase, e.g., Q5), and applying thermal cycling conditions sufficient to amplify the region of the nucleic acid that comprises the effector sequence, thereby producing a linear dsDNA; (iii) digesting the linear dsDNA with an endonuclease (e.g., BsaI, KpnI, or NheI) that cleaves the endonuclease recognition sites, thereby producing a digested linear DNA, (iv) circularizing the digested linear dsDNA (e.g., by contacting the linear digested dsDNA with a ligase, e.g., T4 ligase); and (v) digesting residual linear DNA by contacting a composition comprising the digested linear dsDNA with an exonuclease (e.g., T5 exonuclease).

In some embodiments, the method comprises one or more purification steps, e.g., gel purification or use of a DNA purification column. In some embodiments, the purification step is performed on: the linear dsDNA; the digested linear dsDNA; the circular dsDNA; or the circular ssDNA. In some embodiments, the method does not comprise an organic extraction step (e.g., a phenol-chloroform extraction step).

In some embodiments, the method comprises contacting the nicked dsDNA with the exonuclease (e.g., the T7 exonuclease) for 15-120 minutes, e.g., 20-60 minutes, e.g., about 30 min. In some embodiments, introducing a discontinuity into one strand of the circular dsDNA comprises introducing a nick between two adjacent nucleotides. In some embodiments, introducing a discontinuity into one strand of the circular dsDNA comprises removing a nucleotide, e.g., wherein the nucleotide is a uracil.

In some aspects, the disclosure provides a method of evaluating a sample of a composition comprising ssDNA, the method comprising determining whether a condition is satisfied, wherein the condition is chosen from: a) at least 70%, 80%, 85%, 90%, 95%, 97%, or 98%, or 99% by mass of total DNA in the composition is the covalently closed ssDNA; b) at least 70%, 80%, 85%, 90%, 95%, 96%, 97%, 98%, or 99% by mass of total DNA in the composition is full length; c) less than 10%, 5%, 4%, 3%, 2%, or 1% by mass of DNA in the composition is double stranded DNA (dsDNA); d) less than 10%, 5%, 4%, 3%, 2%, or 1% by mass of DNA in the composition is linear DNA; e) less than 10%, 5%, 4%, 3%, 2%, or 1% by mass of DNA in the composition is linear ssDNA; f) the composition is substantially free of, e.g., is free of, chloroform; g) the composition is substantially free of, e.g., is free of, phenol; h) the composition is substantially free of, e.g., is free of, phenol and chloroform; i) the composition is substantially free of, e.g., is free of, organic solvents; j) the composition is substantially free of, e.g., is free of, aromatic organic solvents; k) the composition is substantially free of (e.g., is free of) Exonuclease III; l) the composition is substantially free of (e.g., is free of) T7 Exonuclease; and/or m) the composition is substantially free of (e.g., is free of) T5 Exonuclease. In some embodiments, if the condition is satisfied, the method comprises performing a downstream processing step on the composition, wherein optionally the downstream processing step is chosen from: dividing the composition into portions, packaging the composition, labeling the composition, shipping the composition, distributing the composition, storing the composition, or releasing the composition into commerce. In some embodiments, the method comprises evaluating a sample of a composition disclosed herein. In some embodiments, the method comprises evaluating a sample of a composition made by a method disclosed herein.

In some embodiments, the ssDNA comprises a chemical modification, e.g., a chemical modification to a sugar, a chemical modification to a base, or a chemical modification to a nucleic acid backbone. In some embodiments, the ssDNA is not a bacteriophage genome. In some embodiments, the ssDNA lacks a bacteriophage packaging site. In some embodiments, the ssDNA lacks a bacteriophage origin of replication. In some embodiments, the ssDNA does not encode a bacteriophage capsid gene. In some embodiments, the ssDNA was not produced by rolling circle amplification. In some embodiments, the ssDNA was not produced by strand displacement amplification. In some embodiments, the ssDNA does not comprise a protelomerase target sequence. In some embodiments, the ssDNA does not comprise a hairpin structure. In some embodiments, the ssDNA does not comprise a first sequence that hybridizes with a second sequence, wherein the first sequence and the second sequence are at least 5 nt long, and wherein the first sequence and the second sequence are positioned less than 6 nucleotides apart from each other. In some embodiments, the ssDNA does not comprise a double strand origin (DSO).

In some embodiments, the chemical modification is a covalent modification selected from 5-formylcytosine; phosphorothioate; 7-methylguanine; and 5-glucosylmethylcytosine.

Definitions

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab').sub.2, Fd, Fvs, single-chain Fvs (scFv), rIgG, single-chain antibodies, disulfide-linked Fvs (sdFv), fragments including either a VL or VH domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and F(ab')2 fragments) that are capable of specifically binding to a target protein. Fab and F(ab')2 fragments lack the Fc fragment of an intact antibody.

As used herein, the term "bacteriophage packaging site" refers to a nucleic acid sequence in a bacteriophage genome that is sufficient to direct packaging into a virion. The bacteriophage packaging site may be, e.g., from bacteriophage P1, T4, T7, or λ.

As used herein, the term "carrier" means a compound, composition, reagent, or molecule that facilitates or promotes the transport or delivery of a composition (e.g., a ssDNA described herein) into a cell. For example, a carrier may be a partially or completely encapsulating agent.

As used herein the term "circular" in reference to a ssDNA described herein, means a ssDNA that lacks a free end. A circular ssDNA may be covalently closed or may form a closed structure without free DNA ends through non-covalent interactions, e.g., the ssDNA may be closed through a splint, e.g., a nucleic acid (e.g., DNA or RNA) splint, through a moiety such as a protein that binds and brings together both ends of a linear ssDNA, or through binding of a plurality of proteins, each of two of the plurality binding to a different ssDNA end, and then binding to each other or a third moiety to close the DNA structure. The term circular does not imply a circular physical configuration or an ssDNA structure lacking any intramolecular structure; a circular ssDNA may have regions of intramolecular double stranded regions or other structures.

As used herein, the term "covalently closed" in reference to a ssDNA means the ssDNA is a continuous strand lacking a free 5' or 3' end.

As used herein, the term "Exonuclease III" refers to the protein Exonuclease III encoded by the *E. coli* genome, or a fragment or variant thereof, that catalyzes removal of nucleotides from a 3' end of DNA, e.g., at a terminus or a nick in the DNA. In some embodiments, the Exonuclease III has an amino acid sequence according to NCBI Reference Sequence NP_416263.1 (which is herein incorporated by reference in its entirety), or a sequence with at least 75%, 80%, 85%, 90%, 95% or 98% identity thereto.

As used herein, the term "T5 exonuclease" refers to the protein encoded by the D15 gene of T5 bacteriophage, or a fragment or variant thereof, that catalyzes removal of nucleotides from a 5' end of DNA, e.g., at a terminus or a nick in the DNA. In some embodiments, the T5 exonuclease has an amino acid sequence according to NCBI Reference Sequence YP_006958.1, or a sequence with at least 75%, 80%, 85%, 90%, 95% or 98% identity thereto.

As used herein, the term "T7 exonuclease" refers to the protein encoded by Gene 6 of T7 bacteriophage, or a fragment or variant thereof, that catalyzes removal of nucleotides from a 5' end of DNA, e.g., at a terminus or a nick in the DNA. In some embodiments, the T7 exonuclease has an amino acid sequence according to NCBI Reference Sequence NP_041988.1, or a sequence with at least 75%, 80%, 85%, 90%, 95% or 98% identity thereto.

As used herein, the term "heterologous", when used to describe a first element in reference to a second element means that the first element and second element do not exist in nature disposed as described. For example, a heterologous polypeptide, nucleic acid molecule, construct or sequence refers to (a) a polypeptide, nucleic acid molecule or portion of a polypeptide or nucleic acid molecule sequence that is not native to a cell in which it is expressed, (b) a polypeptide or nucleic acid molecule or portion of a polypeptide or nucleic acid molecule that has been altered or mutated relative to its native state, or (c) a polypeptide or nucleic acid molecule with an altered expression as compared to the native expression levels under similar conditions. For example, a heterologous regulatory sequence (e.g., promoter, enhancer) may be used to regulate expression of a gene or a nucleic acid molecule in a way that is different than the gene or a nucleic acid molecule is normally expressed in nature. In another example, a heterologous domain of a polypeptide or nucleic acid sequence (e.g., a DNA binding domain of a polypeptide or nucleic acid encoding a DNA binding domain of a polypeptide) may be disposed relative to other domains or may be a different sequence or from a different source, relative to other domains or portions of a polypeptide or its encoding nucleic acid. In certain embodiments, a heterologous nucleic acid molecule may exist in a native host cell genome, but may have an altered expression level or have a different sequence or both. In other embodiments, heterologous nucleic acid molecules may not be endogenous to a host cell or host genome but instead may have been introduced into a host cell by transformation (e.g., transfection, electroporation), wherein the added molecule may integrate into the host genome or can exist as extra-chromosomal genetic material either transiently (e.g., mRNA) or semi-stably for more than one generation (e.g., episomal viral vector, plasmid or other self-replicating vector).

As used herein, the terms "increasing" and "decreasing" refer to modulating resulting in, respectively, greater or lesser amounts, of function, expression, or activity of a metric relative to a reference. For example, subsequent to administration of a ssDNA in a method described herein, the amount of metric described herein (e.g., the level of gene expression, or a marker of innate immunity) may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration, or relative to administration of a control ssDNA, such as a modified ssDNA compared to an unmodified sDNA. Generally, the metric is measured subsequent to administration at a time that the administration has had the recited effect, e.g., at least one day, one week, one month, 3 months, or 6 months, after a treatment regimen has begun.

As used herein, the term "intramolecular complementarity" refers to the ability of two regions within a single DNA strand to hybridize though complementary base pairs and/or form a double stranded structure. Depending on how close together the parts of the sequence are that are self-complementary, a ssDNA may form, e.g., hairpin loops, junctions, bulges or internal loops.

As used herein, the term "linear", when used to describe DNA, means a DNA that comprises two free ends. The linear DNA may be single stranded or double stranded.

As used herein, the term "maintenance sequence" is a DNA sequence or motif that enables or facilitates retention of a DNA molecule in the nucleus through cell division. A maintenance sequence typically enables replication and/or transcription of DNA in the nucleus by interacting with proteins that facilitate chromatin looping. An example of a maintenance sequence is a scaffold/matrix attached region (S/MAR element).

As used herein, a "nuclear targeting sequence" is a DNA sequence that enables or facilitates DNA entry into a target cell nucleus.

As used herein, a "nicking recognition site" refers to a DNA sequence that is specifically recognized and nicked by a nicking endonuclease.

As used herein, a "pharmaceutical composition" or "pharmaceutical preparation" is a composition or preparation which is indicated for human pharmaceutical use, for example, human prophylactic, diagnostic or therapeutic use. A pharmaceutical preparation comprises an active agent having a biological effect on a cell or tissue of a subject, e.g., having pharmacological activity or an effect in the mitigation, treatment, or prevention of disease, in combination with a pharmaceutically acceptable excipient or diluent. A pharmaceutical composition also means a finished dosage form or formulation of a prophylactic, diagnostic or therapeutic composition.

As used herein, the term "second strand motif" or SSM is a sequence or structural motif in a ssDNA that promotes or enables second strand synthesis. An SSM may comprise a binding site(s) for proteins that initiate DNA synthesis of a second strand, and/or places the DNA in the correct orientation for DNA polymerase binding.

As used herein, a ssDNA sequence which is a "sense strand" is a ssDNA which has the same sequence as an mRNA which encodes for a functional protein, and does not serve as a template for transcription. A ssDNA sequence which is an "antisense strand" has a sequence complementary to an mRNA which encodes for a functional protein and/or can serve as a template for transcription.

As used herein, the term "single stranded DNA" or ssDNA means a DNA molecule consisting of a single chain of deoxyribonucleotides. A ssDNA may have paired regions of self-complementarity that form intramolecular/intrastrand double stranded motifs in a folded configuration. Depending on how close together the parts of the sequence are that are self-complementary, the ssDNA may form, e.g., hairpin loops, junctions, bulges or internal loops.

As used herein, "treatment" and "treating" refer to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

BRIEF DESCRIPTION OF THE DRAWINGS

FIG. 1A shows a ssDNA construct comprising a plurality of effector DNA sequence types, in this case an miRNA and a model protein (mCherry), operably linked to an EF1a promoter. FIG. 1C shows a ssDNA construct comprising a nuclear targeting sequence, a promoter, and a sequence encoding an RNA effector. FIG. 1D shows a ssDNA construct comprising a promoter, a sequence encoding a polypeptide, and a second strand motif. FIG. 1E shows a ssDNA construct comprising a nuclear targeting sequence, a promoter operably linked to a sequence encoding a polypeptide, a maintenance sequence, and a second strand motif.

FIG. 10A is an image of a DNA gel with DNA ladder (lane 1) and the nicked DNA (lane 2). The size of the nicked DNA construct is denoted with an arrow. FIG. 10B is an image of a DNA gel with DNA ladder (lane 1) and nicked DNA incubated with T7 exonuclease at 25° C. for 16 hours (lane 2), 1 hour (lane 3), and 30 minutes (lane 4). The size of the ssDNA construct is denoted with an arrow.

FIGS. 12A-12D are a series of graphs depicting the expression of circular ssDNA constructs in HEK293 (FIG. 12A), HepG2 (FIG. 12B), U2OS (FIG. 12C), and HEKa cells (FIG. 12D). Details of the circular ssDNA constructs can be found in Table 5. The x-axis shows the proportion of reporter (mCherry)-positive cells, and the y-axis shows the fluorescent intensity the cells, normalized to the expression of CONSTRUCT001 plasmid. "C1" corresponds to CONSTRUCT001, "C2" corresponds to CONSTRUCT002, etc.

FIG. 13A depicts the percentage of HEKa cells expressing mCherry at day 3 following lipofection, and FIG. 13B depicts the average percentage of mCherry+cells at 6 hours, 1 day, and 3 days post-transfection.

FIGS. 14A-14E are a series of graphs depicting the mRNA levels of IFNβ (FIG. 14A), IL-6 (FIG. 14B), CXCL10 (FIG. 14C), TNFα (FIG. 14D), and IL1B (FIG. 14E) in HEKa cells following lipofection with CONSTRUCT001. CONSTRUCT001 was produced as circular ssDNA and circular dsDNA, and relative molarities of ssDNA or dsDNA are shown (e.g., 1×, 2×, or 4×). mRNA levels were normalized to lipofectamine-only control, and the mRNA levels relative to GAPDH are shown.

FIGS. 16A-16D depicts the secondary structure prediction of circular single-stranded DNA form of CONSTRUCT001. CONSTRUCT001 has a sequence of:

(SEQ ID NO: 55)
ccttcgagaccggctccggtgcccgtcagtgggcagagcgcacatcgcccacagtccccgagaagttggggggaggggtcggcaattg aaccggtgcctagagaaggtggcgcggggtaaactgggaaagtgatgtcgtgtactggctccgccttttttcccgagggtgggggagaacc -continued

Figure 16A:
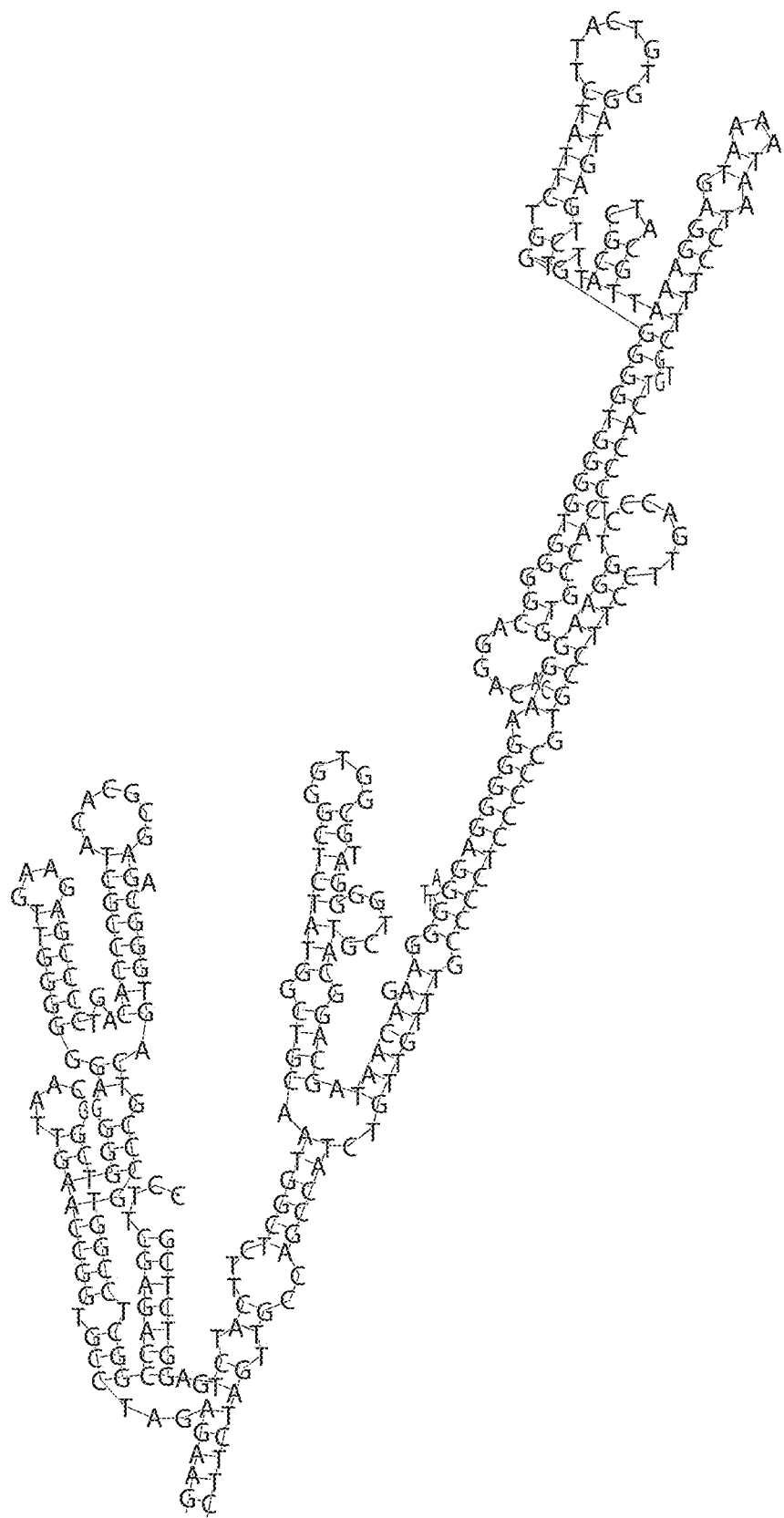
Figure 16B:
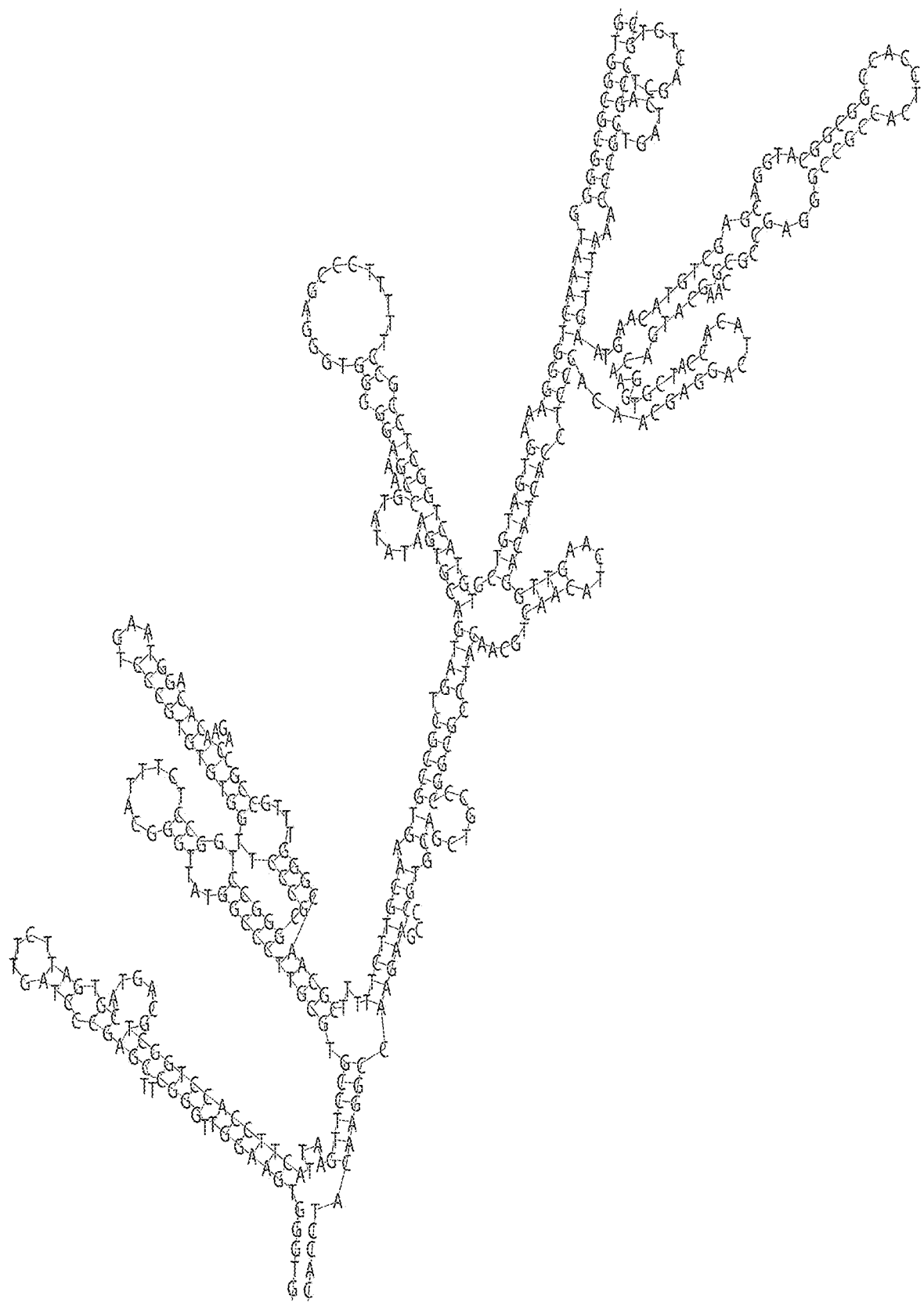
Figure 16C:
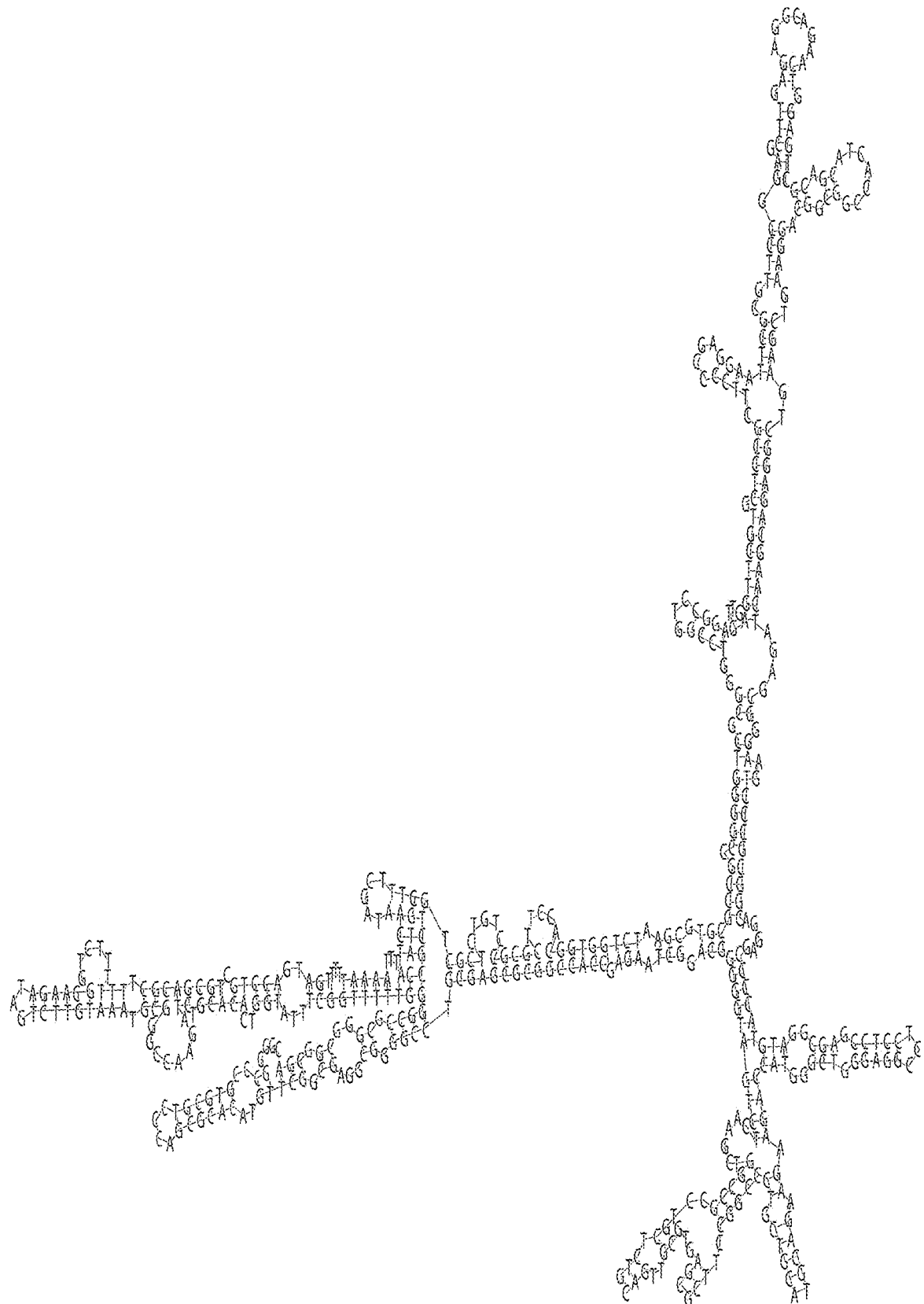
Figure 16D:
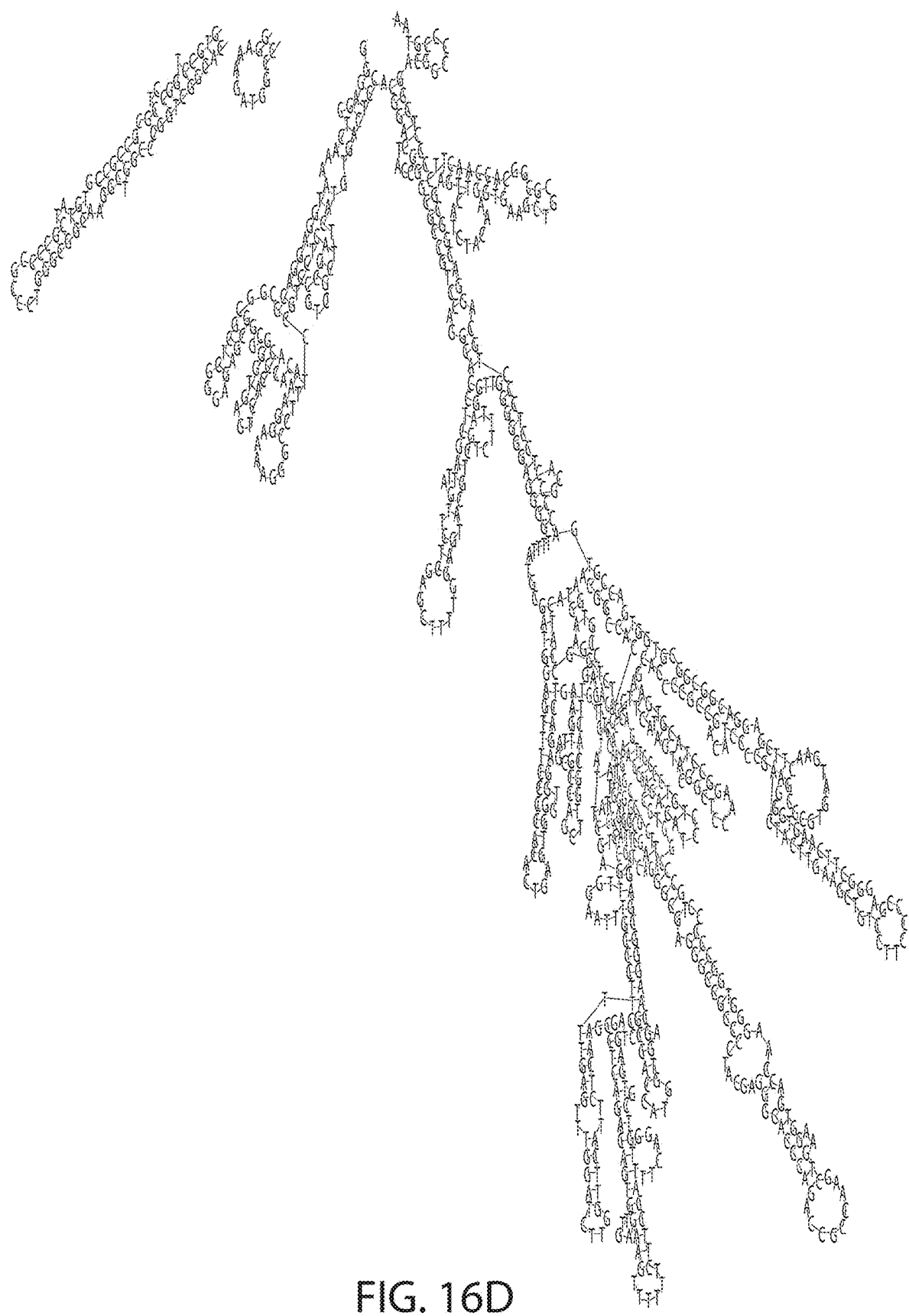

```
gtatataagtgcagtagtcgccgtgaacgttcttttcgcaacgggtttgccgccagaacacaggtaagtgccgtgtgtggttcccgcgggcc tggcctctttacgggttatggcccttgcgtgccttgaattacttccacctggctgcagtacgtgattcttgatcccgagcttcgggttggaagtg ggtgggagagttcgaggccttgcgcttaaggagcccttcgcctcgtgcttgagttgaggcctggcctgggcgctggggccgccgcgtgc gaatctggtggcaccttcgcgcctgtctcgctgctttcgataagtctctagccatttaaaattttgatgacctgctgcgacgctttttttctgg caagatagtcttgtaaatgcgggccaagatctgcacactggtatttcggtttttggggccgcgggcggcgacggggcccgtgcgtcccagcgca catgttcggcgaggcgggcctgcgagcgcggccaccgagaatcggacgggggtagtctcaagctggccggcctgctctggtgcctgg cctcgcgccgccgtgtatcgccccgccctgggcggcaaggctggcccggtcggcaccagttgcgtgagcggaaagatggccgcttccc ggccctgctgcagggagctcaaaatggaggacgcggcgctcgggagagcgggggtgagtcacccacacaaaggaaaagggccttt ccgtcctcagccgtcgcttcatgtgactccacggagtaccgggcgccgtccaggcacctcgattagttctcgagcttttggagtacgtcgtctt taggttgggggagggttttatgcgatggagtttccccacactgagtgggtggagactgaagttaggccagcttggcacttgatgtaattct ccttggaatttgccttttttgagtttggatcttggttcattctcaagcctcagacagtggttcaaagtttttttcttccatttcaggtgtcgtga ggatccgccaccatggtgagcaagggcgaggaggataacatggccatcatcaaggagttcatgcgcttcaaggtgcacatggagggctccgtga acggccacgagttcgagatcgagggcgagggcgagggccgcccctacgagggcacccagaccgccaagctgaaggtgaccaagggt ggcccctgcccttcgcctgggacatcctgtcccctcagttcatgtacggctccaaggcctacgtgaagcacccccgccgacatccccgact acttgaagctgtccttccccgagggcttcaagtgggagcgcgtgatgaacttcgaggacggcggcgtggtgaccgtgacccaggactcct ccctgcaggacggcgagttcatctacaaggtgaagctgcgcggcaccaacttcccctccgacggccccgtaatgcagaagaagaccatg ggctgggaggcctcctccgagcggatgtaccccgaggacggcgccctgaagggcgagatcaagcagaggctgaagctgaaggacgg cggccactacgacgctgaggtcaagaccacctacaaggccaagaagcccgtgcagctgcccggcgcctacaacgtcaacatcaagttgg acatcacctcccacaacgaggactacaccatcgtggaacagtacgaacgcgccgagggccgccactccaccggcggcatggacgagct gtacaagtaagtttaaaccgctgatcagcctcgactgtgccttctagttgccagccatctgttgtttgccctccccgtgccttccttgaccc tggaaggtgccactcccactgtcctttcctaataaaatgaggaaattgcatcgcattgtctgagtaggtgtcattctattctggggggtggggtg gggcaggacagcaaggggggaggattgggaagacaatagcaggcatgctgggatgcggtgggctctatggctgcaatggctcttcatct gaggtctcg. FIG. 16A discloses SEQ ID NOS 57 and 67. FIG. 16B discloses SEQ ID NOS 58 and 66. FIG. 16C discloses SEQ ID NOS 68, 61, 69, and 65. FIG. 16D discloses SEQ ID NOS 60, 62, and 64.
```

DETAILED DESCRIPTION

This disclosure relates to compositions and methods for providing an effector, e.g., a therapeutic effector, to a cell, tissue or subject, e.g., in vivo or in vitro. The effector may be a DNA sequence, a polypeptide, e.g., a therapeutic protein; or an RNA, e.g., a regulatory RNA or an mRNA.
Elements of DNA Constructs The ssDNA constructs described herein contain elements sufficient to deliver an effector sequence to a target cell, tissue or subject. In some embodiments, the effector sequence is a DNA sequence. In some embodiments, the ssDNA drives expression of an effector, e.g., comprises a promoter and a sequence encoding an RNA or a polypeptide, e.g., a therapeutic RNA or polypeptide. In some embodiments, the DNA constructs described herein further contain one or more of: a nuclear targeting sequence, a maintenance sequence, and a second strand motif.
Promoter The ssDNA constructs described herein may contain a promoter (a DNA sequence at which RNA polymerase and transcription factors bind to, directly or indirectly, to initiate transcription) operably linked to an effector sequence. A promoter may be found in nature operably linked to the effector sequence, or may be heterologous to the effector sequence. A promoter described herein may be native to the target cell or tissue, or heterologous to the target cell or tissue. A promoter may be constitutive, inducible and/or tissue-specific.

Examples of constitutive promoters include the retroviral Rous sarcoma virus (RSV) LTR promoter (optionally with the RSV enhancer), the cytomegalovirus (CMV) promoter (optionally with the CMV enhancer) (see, e.g., Boshart et al, *Cell,* 41:521-530 (1985), the SV40 promoter, the dihydrofolate reductase promoter, the beta-actin promoter, the phosphoglycerol kinase (PGK) promoter, and the EF1 alpha promoter.

Inducible promoters allow regulation of expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of sources. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., *Proc. Natl. Acad. Sci. USA,* 93:3346-3351 (1996)), the tetracycline-repressible system (Gossen et al., *Proc. Natl. Acad. Sci. USA,* 89:5547-5551 (1992)), the tetracycline-inducible system (Gossen et al., *Science,* 268:1766-1769 (1995), see also Harvey et al, *Curr. Opin. Chem. Biol.,* 2:512-518 (1998)), the RU486-inducible system (Wang et al., *Nat. Biotech.,* 15:239-243 (1997) and Wang et al., *Gene Ther.,* 4:432-441 (1997)) and the rapamycin-inducible system (Magari et al., *J. Clin. Invest.,* 100:2865-2872 (1997)).

In some embodiments, the native promoter for the sequence encoding the effector can be used. Other native expression control elements, such as enhancer elements, polyadenylation sites or Kozak consensus sequences may also be used.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a alpha-myosin heavy chain (a-MHC) promoter, or a cardiac Troponin T (cTnT) promoter. Other exemplary promoters include Beta-actin promoter, hepatitis B virus core promoter, Sandig et al., *Gene Ther.,* 3:1002-9 (1996); alpha-fetoprotein (AFP) promoter, Arbuthnot et al., *Hum. Gene Ther.,* 7:1503-14 (1996)), bone osteocalcin promoter (Stein et al., *Mol. Biol. Rep.,* 24:185-96 (1997)); bone sialoprotein promoter (Chen et al., *J. Bone Miner. Res.,* 11:654-64 (1996)), CD2 promoter (Hansal et al., *J. Immunol.,* 161:1063-8 (1998); immunoglobulin heavy chain promoter; T cell receptoralpha.-chain promoter, neuronal such as neuron-specific enolase (NSE) promoter (Andersen et al., *Cell. Mol. Neurobiol.,* 13:503-15 (1993)), neurofilament light-chain gene promoter (Piccioli et al., *Proc. Natl. Acad. Sci. USA,* 88:5611-5 (1991)), and the neuron-specific vgf gene promoter (Piccioli et al., *Neuron,* 15:373-84 (1995)), among others which will be known to the skilled artisan.

Examples of tissue/cell specific promoters are listed in Table 1:

TABLE 1

| Tissue or cell specific promoters | | |
|---|---|---|
| Tissue/Cell | Promoter | Accession Number; Human Genome Coordinate (hg38) |
| Skeletal muscle | ACTA1 | NM_001100; chr1: 229, 439, 090-229, 432, 090 |
| Melanoma | TYR | NM_000372; chr11: 89, 300, 750-89, 293, 750 |
| Hepatoma | a-fetoprotein | NM_001354717; chr4: 73, 461, 175-73, 454, 175 |
| Mammary carcinoma | Mucin 1 | NM_001371720; chr1: 155, 197, 900-155, 190, 900 |
| Prostate Cancer | KLK3 | NM_001648; chr19: 50, 865, 760-50, 858, 760 |
| Neuronal cells | ENO2 | NM_001975; chr12: 6, 928, 700-6, 921, 700 |
| Response to Hypoxia | HIF-1alpha | NM_001530; chr14: 61, 753, 200-61, 746, 200 |
| Retinoblastoma | E2F1 | NM_005225; chr20: 33, 691, 380-33, 684, 380 |
| Ionizing radiation | EGR-1 | NM_001964; chr5: 138, 474, 303-138, 467, 303 |
| Oncogene | ErbB2 | NM_004448; chr17: 39, 735, 530-39, 728, 530 |

TABLE 1-continued

| Tissue or cell specific promoters | | |
|---|---|---|
| Tissue/Cell | Promoter | Accession Number; Human Genome Coordinate (hg38) |
| Endothelial cells | vWF | NM_000552; chr12: 6, 129, 670-6, 122, 670 |
| Endothelial cells | FLT-1 | NM_002019; chr13: 28, 500, 100-28, 493, 100 |
| Endothelial cells | ICAM-2 | NM_001099786; chr17: 64, 025, 630-64, 018, 630 |
| Retinal pigment epithelium | VMD2 | NM_004183; chr11: 61, 972, 630-61, 965, 630 |
| Rod cells | RHO | NM_000539; chr3: 129, 540, 350-129, 533, 350 |
| Cone cells | Red/green opsin (OPN1LW) | NM_020061; chrX: 154, 164, 030-154, 157, 030 |
| Ganglion cells | Thymocyte antigen (Thy1) | NM_006288; chr11: 119, 428, 150-119, 421, 150 |
| T cells | TIM3 | NM_032782; chr5: 157, 114, 050-157, 107, 050 |
| T cells | FOXP3 | NM_014009; chrX: 49, 269, 700-49, 262, 700 |
| PBMCs | Vβ6.7 | ENST00000390373.2; chr7: 142, 493, 295-142, 486, 295 |
| Cell cycle | Cdk1 | NM_001786; chr10: 60, 799, 850-60, 792, 850 |

Effector Sequence

The effector sequence of a ssDNA construct described herein may be, e.g., a functional DNA sequence, e.g., a therapeutically functional DNA sequence; a DNA sequence encoding a therapeutic peptide, polypeptide or protein; a DNA sequence encoding a therapeutic RNA (e.g., a non-coding RNA); or a DNA template for genome engineering, e.g., used in combination with a gene editor, a base editor, a prime editor, a gene writer, a mobile genetic element protein.

DNA Effectors:

A therapeutically functional DNA sequence may be a DNA sequence that forms a functional structure, e.g., a DNA sequence comprising a DNA aptamer, DNAzyme or allele-specific oligonucleotide (a DNA ASO). A therapeutically functional DNA sequence may not have a promoter operably linked. In embodiments, a ssDNA construct or sequence described herein may include one or a plurality of functional DNA sequence, e.g., 2, 3, 4, 5, 6, or more sequences, which may be the same or different.

Polypeptide Effectors:

A DNA sequence encoding a therapeutic polypeptide may be a DNA sequence encoding one or more effector which is a peptide, protein, or combinations thereof. For example, the DNA sequence encodes an mRNA. The peptide or protein may be: a transcription factor; a chromatin remodeling factor; an antigen; a hormone; an enzyme (such as a nuclease, e.g., an endonuclease, e.g., a nuclease element of a CRISPR system, e.g., a Cas9, dCas9, aCas9-nickase, Cpf/Cas12a); a Crispr-linked enzyme, e.g. a base editor or prime editor; a mobile genetic element protein (e.g., a transposase, a retrotransposase, a recombinase, an integrase); a gene writer; a polymerase; a methylase; a demethylase; an acetylase; a deacetylase; a kinase; a phosphatase; a ligase; a deubiquitinase; an integrase; a recombinase; a topoisomerase; a gyrase; a helicase; a lysosomal acid hydrolase); an antibody; a receptor ligand; a receptor; a clotting factor; a membrane protein; a mitochondrial protein; a nuclear protein; an antibody or other protein scaffold binder such as a centyrin, a darpin, or adnectin. See, e.g., Gebauer & Skerra. 2020. *Annual Review of Pharmacology and Toxicology* 60:1, 391-415.

In embodiments, a ssDNA construct or sequence described herein may include one or a plurality of sequences encoding a polypeptide, e.g., 2, 3, 4, 5, 6, or more sequences encoding a polypeptide. Each of the plurality may encode the same or different protein. For example, a ssDNA construct or sequence described herein may include multiple sequences encoding multiple proteins, e.g., a plurality of proteins in a biological pathway.

In some embodiments, a ssDNA construct or sequence described herein may include a plurality of sequences encoding a polypeptide, e.g., 2, 3, 4, 5, 6, or more sequences encoding a polypeptide, separated by a self-cleaving peptide, e.g., P2A, T2A, E2A or F2A. Self-cleaving peptides are 18-22 amino acids long, and can induce ribosomal skipping during protein translation so that two polypeptides can be encoded in the same transcript. Each of the polypeptides may encode the same or different protein. In one embodiment, a ssDNA construct or sequence described herein may include a promoter followed by a sequence encoding a first polypeptide of interest, a sequence encoding a 2A self-cleaving peptide, a sequence encoding a second polypeptide of interest, and a polyA tail. In another embodiment, a ssDNA construct or sequence described herein may include a promoter followed by a sequence encoding the first polypeptide of interest, a sequence encoding a first 2A self-cleaving peptide, a sequence encoding a second polypeptide of interest, a sequence encoding a second 2A self-cleaving peptide, a sequence encoding a third polypeptide of interest and a polyA tail.

RNA Effectors:

An effector sequence may be a DNA sequence encoding a non-coding RNA, e.g., one or more of a short interfering RNA (siRNA), a microRNA (miRNA), long non-coding RNA, a piwi-interacting RNA (piRNA), a small nucleolar RNA (snoRNA), a small Cajal body-specific RNA (scaRNA), a transfer RNA (tRNA), a ribosomal RNA (rRNA), an RNA aptamer, and a small nuclear RNA (snRNA).

In some embodiments, the ssDNA construct or sequence disclosed herein comprises one or more expression sequences that encode a regulatory RNA, e.g., an RNA that modifies expression of an endogenous gene and/or an exogenous gene. In some embodiments, the ssDNA construct or sequence disclosed herein can comprise a sequence that is antisense to a regulatory nucleic acid like a non-coding RNA, such as, but not limited to, tRNA, lncRNA, miRNA, rRNA, snRNA, microRNA, siRNA, piRNA, snoRNA, snRNA, exRNA, scaRNA, Y RNA, and hnRNA. In one embodiment, the regulatory nucleic acid targets a host gene. A regulatory nucleic acid may include, but is not limited to, a nucleic acid that hybridizes to an endogenous gene, e.g., an antisense RNA, a guide RNA, a nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, and nucleic acid that modulates a DNA or RNA binding factor. In one embodiment, the sequence is an miRNA. In some embodiments, the regulatory nucleic acid targets a sense strand of a host gene. In some embodiments, the regulatory nucleic acid targets an antisense strand of a host gene In some embodiments, the ssDNA construct or sequence disclosed herein encodes a guide RNA. Guide RNA sequences are generally designed to have a length of between 15-30 nucleotides (e.g., 17, 19, 20, 21, 24 nucleotides) and complementary to the targeted nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991. The gRNA may recognize specific DNA sequences (e.g., sequences adjacent to or within a promoter, enhancer, silencer, or repressor of a gene). In one embodiment, the gRNA is used as part of a CRISPR system for gene editing. For the purposes of gene editing, the ssDNA construct or sequence disclosed herein may be designed to include one or multiple sequences encoding guide RNA sequences corresponding to a desired target DNA sequence; see, for example, Cong et al. (2013) Science, 339:819-823; Ran et al. (2013) Nature Protocols, 8:2281-2308.

A ssDNA construct or sequence disclosed may encode certain regulatory nucleic acids that can inhibit gene expression through the biological process of RNA interference (RNAi). RNAi molecules comprise RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. Such RNAi molecules include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599 8,349,809 and 8,513,207), RNA antisense oligonucleotides (RNA ASOs).

In one embodiment, the ssDNA construct or sequence disclosed herein comprises a sequence comprising a sense strand of a lncRNA. In one embodiment, the ssDNA construct or sequence disclosed herein comprises a sequence encoding an antisense strand of a lncRNA.

The ssDNA construct or sequence disclosed herein may encode a regulatory nucleic acid substantially complementary, or fully complementary, to a fragment of an endogenous gene or gene product (e.g., mRNA). The regulatory nucleic acids may complement sequences at the boundary between introns and exons, in between exons, or adjacent to exon, to prevent the maturation of newly-generated nuclear RNA transcripts of specific genes into mRNA for transcription. The regulatory nucleic acids that are complementary to specific genes can hybridize with the mRNA for that gene and prevent its translation. The antisense regulatory nucleic acid can be DNA, RNA, or a derivative or hybrid thereof. In some embodiments, the regulatory nucleic acid comprises a protein-binding site that can bind to a protein that participates in regulation of expression of an endogenous gene or an exogenous gene.

The length of a ssDNA construct or sequence disclosed herein that may encode a regulatory nucleic acid that hybridizes to a transcript of interest may be between about 5 to 30 nucleotides, between about 10 to 30 nucleotides, or about 11, 12, 13, 14, 15, 16, 17, 18, 19, 20, 21, 22, 23, 24, 25, 26, 27, 28, 29, 30 or more nucleotides. The degree of identity of the regulatory nucleic acid to the targeted transcript should be at least 75%, at least 80%, at least 85%, at least 90%, or at least 95%.

A ssDNA construct or sequence disclosed herein may encode a micro-RNA (miRNA) molecule identical to about 5 to about 30 contiguous nucleotides of a target gene. In some embodiments, the miRNA sequence targets a mRNA and commences with the dinucleotide AA, comprises a GC-content of about 30-70% (about 30-60%, about 40-60%, or about 45%-55%), and does not have a high percentage identity to any nucleotide sequence other than the target in the genome of the mammal in which it is to be introduced, for example as determined by standard BLAST search. In some embodiments, the ssDNA construct or sequence disclosed herein encodes at least one miRNA, e.g., 2, 3, 4, 5, 6, or more. In some embodiments, the ssDNA construct or sequence disclosed herein comprises a sequence that encodes an miRNA having at least about 75%, 80%, 85%, 90% 95%, 96%, 97%, 98%, 99% or 100% nucleotide sequence identity to any one of the nucleotide sequences or a sequence that is complementary to a target sequence. Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed by technologies known in the art. In addition, there are computational tools that increase the chance of finding effective and specific sequence motifs (see, e.g., Lagana et al., *Methods Mol. Bio.*, 2015, 1269: 393-412).

The ssDNA construct or sequence disclosed herein may modulate expression of RNA encoded by a gene. Because multiple genes can share some degree of sequence homology with each other, in some embodiments, the ssDNA construct or sequence disclosed herein can be designed to target a class of genes with sufficient sequence homology. In some embodiments, the ssDNA construct or sequence disclosed herein can contain a sequence that has complementarity to sequences that are shared amongst different gene targets or are unique for a specific gene target. In some embodiments, the ssDNA construct or sequence disclosed herein can be designed to target conserved regions of an RNA sequence having homology between several genes thereby targeting several genes in a gene family (e.g., different gene isoforms, splice variants, mutant genes, etc.). In some embodiments, the ssDNA construct or sequence disclosed herein can be designed to target a sequence that is unique to a specific RNA sequence of a single gene.

In embodiments, the effector sequence encoding a regulatory RNA has a length less than 5000 bps (e.g., less than about 5000 bps, 4000 bps, 3000 bps, 2000 bps, 1000 bps, 900 bps, 800 bps, 700 bps, 600 bps, 500 bps, 400 bps, 300 bps, 200 bps, 100 bps, 50 bps, 40 bps, 30 bps, 20 bps, 10 bps, or less). In some embodiments, the effector sequence has, independently or in addition to, a length greater than 10 bps (e.g., at least about 10 bps, 20 bps, 30 bps, 40 bps, 50 bps, 60 bps, 70 bps, 80 bps, 90 bps, 100 bps, 200 bps, 300 bps, 400 bps, 500 bps, 600 bps, 700 bps, 800 bps, 900 bps, 1000 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4 kb, 4.1 kb, 4.2 kb, 4.3 kb, 4.4 kb, 4.5 kb, 4.6 kb, 4.7 kb, 4.8 kb, 4.9 kb, 5 kb or greater).

In some embodiments, a ssDNA construct or sequence disclosed herein comprises one or more of the features described hereinabove, e.g., one or more structural DNA sequence, a sequence encoding one or more peptides or proteins, a sequence encoding one or more regulatory element, a sequence encoding one or more regulatory nucleic acids, e.g., one or more non-coding RNAs, other expression sequences, and any combination of the aforementioned. A construct described herein may have one or a plurality of effector sequences, e.g., 2, 3, 4, 5 or more effector sequences. In the case of a plurality of effector sequences in a single construct, the effector sequences may be the same or different.

In one embodiment, the ssDNA includes a therapeutically functional, structural DNA sequence. In one embodiment, the ssDNA includes a promoter and a sequence encoding a therapeutic peptide, polypeptide, or protein described herein. In one embodiment, the ssDNA includes a promoter and a sequence encoding a regulatory RNA described herein.

In some embodiment, the effector sequence that encodes a polypeptide or protein is codon optimized, e.g., codon optimized for expression in a mammal, e.g., a human. In general, codon optimization involves modifying a nucleic acid sequence for enhanced expression in the host cells of interest by replacing at least one codon (e.g., one or more, e.g., 1, 2, 3, 4, 5, 10, 15, 20, 25, 50, or more codons; e.g., at least 1%, 5%, 10%, 20%, 25%, 50%, 60%, 70%, 80%, 90% or 100%) of the native sequence with codons that are more frequently or most frequently used in the genes of that host cell while maintaining the native amino acid sequence. Codon usage tables are available, for example, at the "Codon Usage Database" available at http://www.kazusa.or.jp/codon/. These tables can be adapted in a number of ways, see, e.g., Nakamura et al., 2000, *Nucl. Acids Res.* 28:292. Computer algorithms for codon optimizing a particular sequence for expression in a particular host cell are also available, such as Gene Forge.

DNA Templates:

A DNA sequence may be a template for a genome engineering enzyme, (such as a nuclease, e.g., an endonuclease, e.g., a nuclease element of a CRISPR system, e.g., a Cas9, dCas9, aCas9-nickase, Cpf/Cas12a) a Crispr-linked enzyme, e.g. a base editor or prime editor; a mobile genetic element protein (e.g., a transposase, a retrotransposase, a recombinase, an integrase); a gene writer; a polymerase.) The DNA template may comprise one or multiple sequences that are bound by the genome engineering enzyme, such as a DNA binding domain sequence, a sequence targeted by a guide RNA, an inverted repeat, an inverted terminal repeat, a long terminal repeat, a left-terminal sequence (LTS), a right terminal sequence (LTR), an untranslated region, an attachment site (such as an attP, attB, attL, attR), a lox site (such as a LoxP, loxB). The DNA template may comprise a sequence that is homologous to a sequence in the genome, non-homologous to a sequence in the genome, or a combination thereof. The template may be a substrate for DNA repair, e.g. non-homologous end joining, homologous recombination, or microhomology mediated end-joining. The DNA template may comprise machinery to express a gene or RNA, such as an enhancer, promoter, protein coding region, RNA coding region. In some embodiments, the sequences bound by the genome engineering enzyme are placed on either side of a functional DNA sequence that is inserted into the genome or used as a template for genome repair. In some embodiments, one or both of the sequences bound by the genome engineering enzyme are inserted into the genome and in some embodiments they are not. In embodiments, a ssDNA construct or sequence described herein may include one or a plurality of functional templates sequence, e.g., 2, 3, 4, 5, 6, or more sequences, which may be the same or different.

Nuclear Targeting Sequence (NTS)

A DNA construct or sequence disclosed herein may include a nuclear targeting sequence (NTS) that facilitates transport of DNA from the cytoplasm into the nucleus of a cell. An NTS includes binding sites to proteins (e.g., transcription factors, chaperones, etc.) which bind to importin which transports cargo into the nucleus via the nuclear pore complex. In embodiments, an NTS may function generally (e.g. SV40 enhancer NTS). In other embodiments, NTS's may be cell or tissue specific, e.g., containing binding sites for transcription factors expressed in unique cell types may target a ssDNA sequence or construct described herein to the nucleus in a cell-specific manner (e.g., SRF, Nkx3). An NTS can be functional in multiple locations in an ssDNA or construct described herein, e.g., before the promoter and/or after the effector sequence.

An NTS may be viral or non-viral derived. NTSs are described, e.g., in Le Guen et al. 2021. *Nucleic Acids* Vol. 24: 477-486. Examples of NTS's are disclosed in Table 2:

TABLE 2 exemplary nuclear targeting sequences

| Viral/Non-viral | Name | Sequence |
|---|---|---|
| Viral | SV40 | 5'-cccaagaagaagaggaaagtc-3' (SEQ ID NO: 1) |
| Non-viral | 3NF | 5'-ctggggactttccagcctggggactttccagctgggactttccagg-3' (SEQ ID NO: 2) |

Nuclear Import Proteins

In some embodiments, a ssDNA (e.g., as described herein) is capable of being imported into the nucleus, e.g., by a nuclear import protein (e.g., a nuclear import protein as listed in Table 2B). In some embodiments, a ssDNA (e.g., as described herein) can be bound by a nuclear import protein (e.g., a nuclear import protein as listed in Table 2B). In some embodiments, a ssDNA (e.g., as described herein) comprises a recognition sequence for a nuclear import protein (e.g., as listed in any single row of Table 2B). In some embodiments, a ssDNA (e.g., as described herein) comprises a recognition sequence as listed in Table 2B, or a nucleic acid sequence having at least 75%, 80%, 90%, 95%, 96%, 97%, 98%, or 99% identity thereto.

Exemplary import proteins include, e.g., basic helix-loop-helix (bHLH) proteins, heterogeneous nuclear ribonucleoprotein (hnRNP) isoforms, nuclear factor I (NFI) proteins, e.g., those listed in Table 2B. In some embodiments, the bHLH protein comprises an acetylcholine receptor subunit, e.g., an alpha subunit, e.g., CHRNA1, CHRNA2, CHRNA3, CHRNA4, CHRNA5, or CHRNA7. In some embodiments, the acetylcholine receptor subunit comprises a gamma or epsilon subunit. In some embodiments, the import protein comprises a desmin. In some embodiments, the import protein comprises an hnRNP, e.g., an hnRNP A1, an hnRNP C, an hnRNP K, an hnRNP U. In some embodiments, the import protein comprises an importin. In some embodiments, the import protein comprises a myosin light chain. In some embodiments, the import protein comprises an NFI. In some embodiments, the import protein comprises an NFKB. In some embodiments, the import protein comprises a nucleoside diphosphate kinase, e.g., an NM23-H2. In some embodiments, the import protein comprises an Oct1. In some embodiments, the import protein comprises an Oct2.

In some embodiments, the import protein comprises a SRF. In some embodiments, the import protein comprises a TEF-1. In some embodiments, the import protein comprises an AP2. In some embodiments, the import protein comprises a troponin, e.g., a troponin I, e.g., a troponin I2. In some embodiments, the import protein comprises a TTF-1. In some embodiments, the import protein comprises a Ran binding protein, e.g., a RanBP3 or a RanBP1. In some embodiments, the import protein comprises a homeobox transcription factor, e.g., Chx10.

In some embodiments, the import factor specifically binds an E-box, a DTS (e.g., a SV40 DTS or a SMGA DTS), a promoter (e.g., a SP-C promoter or an htk promoter), a telomere, an ATTT motif, a cell cycle regulatory unit (CCRU), a CT3 sequence, an S/MAR, a topoisomerase II consensus sequence, an ARS consensus sequence, a 3NF, a viral on (e.g., EBV oriP site).

TABLE 2B

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| cardiac alpha-actin | 70 | NP_005150.1 | E-boxes | 5'-CANNTG-3' | |
| CHRNA1 isoform b | 1134 | NP_000070.1 | E-boxes | 5'-CANNTG-3' | |
| CHRNA1 isoform a | 1134 | NP_001034612.1 | E-boxes | 5'-CANNTG-3' | |
| CHRNA2 isoform 1 | 1135 | NP_000733.2 | E-boxes | 5'-CANNTG-3' | |
| CHRNA2 isoform 2 | 1135 | NP_001269384.1 | E-boxes | 5'-CANNTG-3' | |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| CHRNA2 isoform 3 | 1135 | NP_001334634.1 | E-boxes | 5'-CANNTG-3' | |
| CHRNA2 isoform 3 | 1135 | NP_001334635.1 | E-boxes | 5'-CANNTG-3' | |
| CHRNA2 isoform 4 | 1135 | NP_001334636.1 | E-boxes | 5'-CANNTG-3' | |
| CHRNA2 isoform 4 | 1135 | NP_001334637.1 | E-boxes | 5'-CANNTG-3' | |
| CHRNA3 isoform 1 | 1136 | NP_000734.2 | E-boxes | 5'-CANNTG-3' | |
| CHRNA3 isoform 2 | 1136 | NP_001160166.1 | E-boxes | 5'-CANNTG-3' | |
| CHRNA4 isoform 1 | 1137 | NP_000735.1 | E-boxes | 5'-CANNTG-3' | |
| CHRNA4 isoform 2 | 1137 | NP_001243502.1 | E-boxes | 5'-CANNTG-3' | |
| CHRNA5 isoform 1 | 1138 | NP_000736.2 | E-boxes | 5'-CANNTG-3' | |
| CHRNA5 isoform 2 | 1138 | NP_001294874.1 | E-boxes | 5'-CANNTG-3' | |
| CHRNA5 isoform 3 | 1138 | NP_001382100.1 | E-boxes | 5'-CANNTG-3' | |
| CHRNA5 isoform 4 | 1138 | NP_001382101.1 | E-boxes | 5'-CANNTG-3' | |
| CHRNA5 isoform 5 | 1138 | NP_001382102.1 | E-boxes | 5'-CANNTG-3' | |
| CHRNA5 isoform 6 | 1138 | NP_001382103.1 | E-boxes | 5'-CANNTG-3' | |
| CHRNA5 isoform 7 | 1138 | NP_001382104.1 | E-boxes | 5'-CANNTG-3' | |
| CHRNA7 isoform 1 | 1139 | NP_000737.1 | E-boxes | 5'-CANNTG-3' | |
| CHRNA7 isoform 2 | 1139 | NP_001177384.1 | E-boxes | 5'-CANNTG-3' | |
| CHRNE | 1145 | NP_000071.1 | E-boxes | 5'-CANNTG-3' | |
| CHRNG | 1146 | NP_005190.4 | E-boxes | 5'-CANNTG-3' | |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| M-creatine kinase (MCK) | 1158 | NP_001815.2 | E-boxes | 5'-CANNTG-3' | |
| desmin isoform 2 | 1674 | NP_001369637.1 | E-boxes | 5'-CANNTG-3' | |
| desmin isoform 3 | 1674 | NP_001369638.1 | E-boxes | 5'-CANNTG-3' | |
| desmin isoform 4 | 1674 | NP_001369639.1 | E-boxes | 5'-CANNTG-3' | |
| desmin isoform 5 | 1674 | NP_001369640.1 | E-boxes | 5'-CANNTG-3' | |
| desmin isoform 6 | 1674 | NP_001369641.1 | E-boxes | 5'-CANNTG-3' | |
| desmin isoform 7 | 1674 | NP_001369642.1 | E-boxes | 5'-CANNTG-3' | |
| desmin isoform 1 | 1674 | NP_001918.3 | E-boxes | 5'-CANNTG-3' | |
| AP1 (Fos) | 2353 | NP_005243.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| GATA-6 | 2627 | NP_005248.2 | SP-C promoter | 5'-CAGGGCAGCAGGGGCAGGTGCCAGCAAGGAAGGCAGGCACGCCAGGAAGACACCCATGGTGAGAAGTGCAGATGGCCCGAGGGCAAGTTTGCTCAACTCACCCAGGTTTGCTCTTGCTGGGGCCAAGAGGACTCATGTGCCAGGGCCAAGGGCCCTTGGGGGCTCTCACAGGGGGCTTATCTGGGCTTCGGTTCTGGAGGGCCAGGAACAAACAGGCTTCAAAGCCAAGGGCTTGGCTGGCACACAGGGGGCTTGGTCCTTCACCTCTGTCCCCTCTCCCTACGGACACATATAAGACCCTGGTCACACCTGGGAGAGGAGGAGAGGAGAGCATAG-3' | 5 |
| hnRNP A1 isoform a | 3178 | NP_002127.1 | dsDNA sequence from human chromosome band 11q13 (accession number AC000353) | 5'-GGCTGGTCTTGAACTCCTG(A/G)GCTCA(A/G)GTGATCCTCC(A/G)-3' | 6 |
| hnRNP A1 isoform b | 3178 | NP_112420.1 | dsDNA sequence from human chromosome band 11q13 (accession number AC000353) | 5'-GGCTGGTCTTGAACTCCTG(A/G)GCTCA(A/G)GTGATCCTCC-3' | 6 |
| hnRNP A1 | 3178 | NP_002127.1 | Telomere (binds to | 5'-(TTAGGG)n-3' | |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| isoform a | | | telomeric repeats | | |
| hnRNP A1 isoform b | 3178 | NP_112420.1 | Telomere (binds to telomeric repeats) | 5'-(TTAGGG)n-3' | |
| hnRNP A1 isoform a | 3178 | NP_002127.1 | human thymidine kinase (htk) promoter, ATTT sequence motif contained within the cell cycle regulatory unit (CCRU) | 5'-TGCGGCCAAATCTCCCGCCAGGTCAGC-3' | 8 |
| hnRNP A1 isoform b | 3178 | NP_112420.1 | human thymidine kinase (htk) promoter, ATTT sequence motif contained within the cell cycle regulatory unit (CCRU) | 5'-TGCGGCCAAATCTCCCGCCAGGTCAGC-3' | 8 |
| hnRNP A1 isoform a | 3178 | NP_002127.1 | human thymidine kinase (htk) promoter, ATTT sequence motif contained within the cell cycle regulatory unit (CCRU) | 3'-ACGCCGGTTTAGAGGGCGGTCCAGTCG-5' | 9 |
| hnRNP A1 isoform b | 3178 | NP_112420.1 | human thymidine kinase (htk) promoter, ATTT sequence motif contained within the cell cycle regulatory unit (CCRU) | 3'-ACGCCGGTTTAGAGGGCGGTCCAGTCG-5' | 9 |
| hnRNP C isoform a | 3183 | NP_001070910.1 | human thymidine kinase (htk) promoter, ATTT sequence motif contained within the cell cycle regulatory unit (CCRU) | 5'-TGCGGCCAAATCTCCCGCCAGGTCAGC-3' | 8 |
| hnRNP C isoform b | 3183 | NP_001070911.1 | human thymidine kinase (htk) promoter, ATTT sequence motif contained within the cell cycle | 5'-TGCGGCCAAATCTCCCGCCAGGTCAGC-3' | 8 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| | | | regulatory unit (CCRU) | | |
| hnRNP C isoform b | 3183 | NP_004491.2 | human thymidine kinase (htk) promoter, ATTT sequence motif contained within the cell cycle regulatory unit (CCRU) | 5'-TGCGGCCAAATCTCCCGCCAGGTCAGC-3' | 8 |
| hnRNP C isoform a | 3183 | NP_112604.2 | human thymidine kinase (htk) promoter, ATTT sequence motif contained within the cell cycle regulatory unit (CCRU) | 5'-TGCGGCCAAATCTCCCGCCAGGTCAGC-3' | 8 |
| hnRNP C isoform a | 3183 | NP_001070910.1 | human thymidine kinase (htk) promoter, ATTT sequence motif contained within the cell cycle regulatory unit (CCRU) | 3'-ACGCCGGTTTAGAGGGCGGTCCAGTCG-5' | 9 |
| hnRNP C isoform b | 3183 | NP_001070911.1 | human thymidine kinase (htk) promoter, ATTT sequence motif contained within the cell cycle regulatory unit (CCRU) | 3'-ACGCCGGTTTAGAGGGCGGTCCAGTCG-5' | 9 |
| hnRNP C isoform b | 3183 | NP_004491.2 | human thymidine kinase (htk) promoter, ATTT sequence motif contained within the cell cycle regulatory unit (CCRU) | 3'-ACGCCGGTTTAGAGGGCGGTCCAGTCG-5' | 9 |
| hnRNP C isoform a | 3183 | NP_112604.2 | human thymidine kinase (htk) promoter, ATTT sequence motif contained within the cell cycle regulatory unit (CCRU) | 3'-ACGCCGGTTTAGAGGGCGGTCCAGTCG-5' | 9 |
| hnRNP K isoform c | 3190 | NP_001305115.1 | CT3 | 5'-AATTCTCCTCCCCACCTTCCCCACCCTCCCCA-3' | 10 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| hnRNP K isoform d | 3190 | NP_001305116.1 | CT3 | 5'-AATTCTCCTCCCCACCTTCCCCACCCTCCCCA-3' | 10 |
| hnRNP K isoform b | 3190 | NP_001305117.1 | CT3 | 5'-AATTCTCCTCCCCACCTTCCCCACCCTCCCCA-3' | 10 |
| hnRNP K isoform a | 3190 | NP_002131.2 | CT3 | 5'-AATTCTCCTCCCCACCTTCCCCACCCTCCCCA-3' | 10 |
| hnRNP K isoform b | 3190 | NP_112552.1 | CT3 | 5'-AATTCTCCTCCCCACCTTCCCCACCCTCCCCA-3' | 10 |
| hnRNP K isoform a | 3190 | NP_112553.1 | CT3 | 5'-AATTCTCCTCCCCACCTTCCCCACCCTCCCCA-3' | 10 |
| hnRNP U (aka SAF-A) isoform b | 3192 | NP_004492.2 | S/MAR | 5'-TATATTT-3' | |
| hnRNP U (aka SAF-A) isoform a | 3192 | NP_114032.2 | S/MAR | 5'-TATATTT-3' | |
| hnRNP U (aka SAF-A) isoform b | 3192 | NP_004492.2 | S/MAR | 5'-(A/G)N(T/C)NNCNNG(T/C)NG(G/T)TN(T/C)N(T/C)-3' | 12 |
| hnRNP U (aka SAF-A) isoform a | 3192 | NP_114032.2 | S/MAR | 5'-(A/G)N(T/C)NNCNNG(T/C)NG(G/T)TN(T/C)N(T/C)-3' | 12 |
| hnRNP U (aka SAF-A) isoform | 3192 | NP_004492.2 | S/MAR | 5'-(A/T)TTTAT(A/G)TTT(A/T)-3' | 13 |
| hnRNP U (aka SAF-A) isoform a | 3192 | NP_114032.2 | S/MAR | 5'-(A/T)TTTAT(A/G)TTT(A/T)-3' | 13 |
| AP1 (Jun) | 3725 | NP_002219.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Importin β1 | 3837 | XP_548162.2 | SMGA DTS | 5'-AGGCAGACCCAGGGGCCGCATGCAGCAGGGCCTGAGGAGGGAGGTGTGGACGGAGGAGGCCCGCTGCCATTCTTGGTATGGTTCTCACTCCAGGAGCACAGCTGCATCTGGTCTCACTCTGGGCAGCTTATAAGGCCTGGTGTGAGTTTTGTTTATGCAAGTGCAGCATAAAAGGAACAAATCTACCAGCACCGGGGCTGTTGCCACTGAGTCCTTTTGCATACATTTTTCAAATGATAACTCACTCTACCCACCCCCCTTCCCTACCCCCAAGGCGATTTATTGAAAAACCACCTTATATGGTAATATTGCTAACACACC | 14 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| | | | | GTCAGCTGGCCTTTTTAGGGACTTTGTTTAAAG AAGATCCGCCTCTGGGGTTTTATATTGCTCTGG TATTCATGCCAAAGAC-3' | |
| myosin light chain (MLC) 1/3 isoform 1f | 4632 | NP_524144.1 | E-boxes | 5'-CANNTG-3' | |
| myosin light chain (MLC) 1/3 isoform 3f | 4632 | NP_524146.1 | E-boxes | 5'-CANNTG-3' | |
| NFI isoform 1 | 4782 | NP_001231931.1 | SP-C promoter | 5'-CAGGGCAGCAGGGGCAGGTGCCAGCAAGGAA GGCAGGCACGCCAGGAAGACACCCATGGTGA GAAGTGCAGATGGCCCGAGGGCAAGTTTGCTC AACTCACCCAGGTTTGCTCTTGCTGGGGCCAA GAGGACTCATGTGCCAGGGCCAAGGGCCCTTG GGGGCTCTCACAGGGGGCTTATCTGGGCTTCG GTTCTGGAGGGCCAGGAACAAACAGGCTTCAA AGCCAAGGGCTTGGCTGGCACACAGGGGGCTT GGTCCTTCACCTCTGTCCCCTCTCCCTACGGAC ACATATAAGACCCTGGTCACACCTGGGAGAGG AGGAGAGGAGAGCATAG-3' | 16 |
| NFI isoform 3 | 4782 | NP_001231933.1 | SP-C promoter | 5'-CAGGGCAGCAGGGGCAGGTGCCAGCAAGGAA GGCAGGCACGCCAGGAAGACACCCATGGTGA GAAGTGCAGATGGCCCGAGGGCAAGTTTGCTC AACTCACCCAGGTTTGCTCTTGCTGGGGCCAA GAGGACTCATGTGCCAGGGCCAAGGGCCCTTG GGGGCTCTCACAGGGGGCTTATCTGGGCTTCG GTTCTGGAGGGCCAGGAACAAACAGGCTTCAA AGCCAAGGGCTTGGCTGGCACACAGGGGGCTT GGTCCTTCACCTCTGTCCCCTCTCCCTACGGAC ACATATAAGACCCTGGTCACACCTGGGAGAGG AGGAGAGGAGAGCATAG-3' | 16 |
| NFI isoform 4 | 4782 | NP_001231934.1 | SP-C promoter | 5'-CAGGGCAGCAGGGGCAGGTGCCAGCAAGGAA GGCAGGCACGCCAGGAAGACACCCATGGTGA GAAGTGCAGATGGCCCGAGGGCAAGTTTGCTC AACTCACCCAGGTTTGCTCTTGCTGGGGCCAA GAGGACTCATGTGCCAGGGCCAAGGGCCCTTG GGGGCTCTCACAGGGGGCTTATCTGGGCTTCG GTTCTGGAGGGCCAGGAACAAACAGGCTTCAA AGCCAAGGGCTTGGCTGGCACACAGGGGGCTT GGTCCTTCACCTCTGTCCCCTCTCCCTACGGAC ACATATAAGACCCTGGTCACACCTGGGAGAGG AGGAGAGGAGAGCATAG-3' | 16 |
| NFI isoform 5 | 4782 | NP_005588.2 | SP-C promoter | 5'-CAGGGCAGCAGGGGCAGGTGCCAGCAAGGAA GGCAGGCACGCCAGGAAGACACCCATGGTGA GAAGTGCAGATGGCCCGAGGGCAAGTTTGCTC AACTCACCCAGGTTTGCTCTTGCTGGGGCCAA GAGGACTCATGTGCCAGGGCCAAGGGCCCTTG GGGGCTCTCACAGGGGGCTTATCTGGGCTTCG GTTCTGGAGGGCCAGGAACAAACAGGCTTCAA AGCCAAGGGCTTGGCTGGCACACAGGGGGCTT GGTCCTTCACCTCTGTCCCCTCTCCCTACGGAC ACATATAAGACCCTGGTCACACCTGGGAGAGG AGGAGAGGAGAGCATAG-3' | 16 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| NFI isoform 2 | 4782 | NP_995315.1 | SP-C promoter | 5'-CAGGGCAGCAGGGGCAGGTGCCAGCAAGGAAGGCAGGCACGCCAGGAAGACACCCATGGTGAGAAGTGCAGATGGCCCGAGGGCAAGTTTGCTCAACTCACCCAGGTTTGCTCTTGCTGGGGCCAAGAGGACTCATGTGCCAGGGCAAGGGCCCTTGGGGGCTCTCACAGGGGGCTTATCTGGGCTTCGGTTCTGGAGGGCCAGGAACAAACAGGCTTCAAAGCCAAGGGCTTGGCTGGCACACAGGGGGCTTGGTCCTTCACCTCTGTCCCCTCTCCCTACGGACACATATAAGACCCTGGTCACACCTGGGAGAGGAGGAGAGGAGAGCATAG-3' | 16 |
| NFKB isoform 2 | 4790 | NP_001158884.1 | 3NF | 5'-CTGGGGACTTTCCAGCCTGGGGACTTTCCAGCTGGGACTTTCCAGG-3' | 2 |
| NFKB isoform 2 | 4790 | NP_001306155.1 | 3NF | 5'-CTGGGGACTTTCCAGCCTGGGGACTTTCCAGCTGGGACTTTCCAGG-3' | 2 |
| NFKB isoform 1 | 4790 | NP_001369554.1 | 3NF | 5'-CTGGGGACTTTCCAGCCTGGGGACTTTCCAGCTGGGACTTTCCAGG-3' | 2 |
| NFKB isoform 1 | 4790 | NP_001369555.1 | 3NF | 5'-CTGGGGACTTTCCAGCCTGGGGACTTTCCAGCTGGGACTTTCCAGG-3' | 2 |
| NFKB isoform 2 | 4790 | NP_001369556.1 | 3NF | 5'-CTGGGGACTTTCCAGCCTGGGGACTTTCCAGCTGGGACTTTCCAGG-3' | 2 |
| NFKB isoform 3 | 4790 | NP_001369557.1 | 3NF | 5'-CTGGGGACTTTCCAGCCTGGGGACTTTCCAGCTGGGACTTTCCAGG-3' | 2 |
| NFKB isoform 1 | 4790 | NP_003989.2 | 3NF | 5'-CTGGGGACTTTCCAGCCTGGGGACTTTCCAGCTGGGACTTTCCAGG-3' | 2 |
| NFKB isoform 2 | 4790 | NP_001158884.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NFKB isoform 2 | 4790 | NP_001306155.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NFKB isoform 1 | 4790 | NP_001369554.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NFKB isoform 1 | 4790 | NP_001369555.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NFKB isoform 2 | 4790 | NP_001369556.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NFKB isoform 3 | 4790 | NP_001369557.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| NFKB isoform 1 | 4790 | NP_003989.2 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NFKB isoform 2 | 4790 | NP_001158884.1 | A fragment consisting of five tandem repeats of the Igκ κB motif 5'-GGGGACTTTCC-3' (SEQ ID NO: 56) | 5'-GGGGACTTTCCGGGGACTTTCCGGGGACTTTCGGGGACTTTCCGGGGACTTTCC-3' | 17 |
| NFKB isoform 2 | 4790 | NP_001306155.1 | A fragment consisting of five tandem repeats of the Igκ κB motif 5'-GGGGACTTTCC-3' (SEQ ID NO: 56) | 5'-GGGGACTTTCCGGGGACTTTCCGGGGACTTTCGGGGACTTTCCGGGGACTTTCC-3' | 17 |
| NFKB isoform 1 | 4790 | NP_001369554.1 | A fragment consisting of five tandem repeats of the Igκ κB motif 5'-GGGGACTTTCC-3' (SEQ ID NO: 56) | 5'-GGGGACTTTCCGGGGACTTTCCGGGGACTTTCGGGGACTTTCCGGGGACTTTCC-3' | 17 |
| NFKB isoform 1 | 4790 | NP_001369555.1 | A fragment consisting of five tandem repeats of the Igκ κB motif 5'-GGGGACTTTCC-3' (SEQ ID NO: 56) | 5'-GGGGACTTTCCGGGGACTTTCCGGGGACTTTCGGGGACTTTCCGGGGACTTTCC-3' | 17 |
| NFKB isoform 2 | 4790 | NP_001369556.1 | A fragment consisting of five tandem repeats of the Igκ κB motif 5'-GGGGACTTTCC-3' (SEQ ID NO: 56) | 5'-GGGGACTTTCCGGGGACTTTCCGGGGACTTTCGGGGACTTTCCGGGGACTTTCC-3' | 17 |
| NFKB isoform 3 | 4790 | NP_001369557.1 | A fragment consisting of five tandem repeats of the Igκ κB motif 5'-GGGGACTTTCC-3' (SEQ ID NO: 56) | 5'-GGGGACTTTCCGGGGACTTTCCGGGGACTTTCGGGGACTTTCCGGGGACTTTCC-3' | 17 |
| NFKB isoform 1 | 4790 | NP_003989.2 | A fragment consisting of five tandem repeats of the Igκ κB motif 5'- | 5'-GGGGACTTTCCGGGGACTTTCCGGGGACTTTCGGGGACTTTCCGGGGACTTTCC-3' | 17 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| | | | GGGGACTTTCC-3' (SEQ ID NO: 56) | | |
| NM23-H2 isoform a | 4831 | NP_001018147.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NM23-H2 isoform a | 4831 | NP_001018148.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NM23-H2 isoform a | 4831 | NP_001018149.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NM23-H2 isoform b | 4831 | NP_001185611.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| NM23-H2 isoform a | 4831 | NP_002503.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 1 | 5452 | NP_001193954.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 3 | 5452 | NP_001193955.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 4 | 5452 | NP_001234923.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 5 | 5452 | NP_001380863.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 6 | 5452 | NP_001380864.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 7 | 5452 | NP_001380865.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 8 | 5452 | NP_001381305.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2) isoform 9 | 5452 | NP_001381306.1 | SV40 DTS | 5'-GGTGTGGAAAGTCCCCAGGCTCCCCAGCAGGCAGAAGTATGCAAAGCATGCATCTCAATTAGTCAGCAACCA-3' | 4 |
| Oct2 (POU2F2 | 5452 | NP_001381307.1 | SV40 DTS | 5'-GGTGTGGAAAGTCCCCAGGCTCCCCAGCAGGC | 4 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| isoform 10 | | | | AGAAGTATGCAAAGCATGCATCTCAATTAGTC AGCAACCA-3' | |
| Oct2 (POU2F2) isoform 2 | 5452 | NP_002689.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| RanBP1 | 5902 | XP_514990.2 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 18 |
| Oct1 (POU2F1) isoform 2 | 5451 | NP_001185712.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| Oct1 (POU2F1) isoform 3 | 5451 | NP_001185715.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| Oct1 (POU2F1) isoform 4 | 5451 | NP_001352777.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| Oct1 (POU2F1) isoform 4 | 5451 | NP_001352778.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| Oct1 (POU2F1) isoform 1 | 5451 | NP_002688.3 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| SRF isoform 2 | 6722 | NP_001278930.1 | SMGA DTS | 5'-TTCAAATGATAACTCACTCTACCCACCCCCTT CCCTACCCCCAAGGCGATTTATTGAAAAACC ACCTTATATGGTAATATTGCTAACACACCGTC AGCTGGCCTTTTTAGGGACTTTGTTTAAAGAA GATCCGCCTCTGGGGTTTTATATTGCTCTGGTA TTCATGCCAAAGAC-3' | 19 |
| SRF isoform 1 | 6722 | NP_003122.1 | SMGA DTS | 5'-TTCAAATGATAACTCACTCTACCCACCCCCTT CCCTACCCCCAAGGCGATTTATTGAAAAACC ACCTTATATGGTAATATTGCTAACACACCGTC AGCTGGCCTTTTTAGGGACTTTGTTTAAAGAA GATCCGCCTCTGGGGTTTTATATTGCTCTGGTA TTCATGCCAAAGAC-3' | 19 |
| TEF-1 isoform 2 | 7008 | NP_001138870.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| TEF-1 isoform | 7008 | NP_003207.1 | SV40 DTS | 5'-GGTGTGGAAAGTCCCCAGGCTCCCCAGCAGGC | 4 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| 1 | | | | AGAAGTATGCAAAGCATGCATCTCAATTAGTC AGCAACCA-3' | |
| AP2 (TFAP2A) isoform b | 7020 | NP_ 001027451.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| AP2 (TFAP2A) isoform c | 7020 | NP_ 001035890.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| AP2 (TFAP2A) isoform a | 7020 | NP_ 001358995.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| AP2 (TFAP2B) | 7021 | NP_003212.2 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| AP2 (TFAP2C) | 7022 | NP_003213.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| troponin I 1 | 7135 | NP_003272.3 | E-boxes | 5'-CANNTG-3' | |
| troponin I 2-isoform 1 | 7136 | NP_ 001139301.1 | E-boxes | 5'-CANNTG-3' | |
| troponin I 2-isoform 2 | 7136 | NP_ 001139313.1 | E-boxes | 5'-CANNTG-3' | |
| troponin I 2-isoform 1 | 7136 | NP_003273.1 | E-boxes | 5'-CANNTG-3' | |
| troponin I 3 | 7137 | NP_000354.4 | E-boxes | 5'-CANNTG-3' | |
| TTF-1 isoform 2 | 7270 | NP_ 001192225.1 | SP-C promoter | 5'-CAGGGCAGCAGGGGCAGGTGCCAGCAAGGAA GGCAGGCACGCCAGGAAGACACCCATGGTGA GAAGTGCAGATGGCCCGAGGGCAAGTTTGCTC AACTCACCCAGGTTTGCTCTTGCTGGGGCCAA GAGGACTCATGTGCCAGGGCCAAGGGCCCTTG GGGGCTCTCACAGGGGGCTTATCTGGGCTTCG GTTCTGGAGGGCCAGGAACAAACAGGCTTCAA AGCCAAGGGCTTGGCTGGCACACAGGGGGCTT GGTCCTTCACCTCTGTCCCCTCTCCCTACGGAC ACATATAAGACCCTGGTCACACCTGGGAGAGG AGGAGAGGAGAGCATAG-3' | 21 |
| TTF-1 isoform 1 | 7270 | NP_031370.2 | SP-C promoter | 5'-CAGGGCAGCAGGGGCAGGTGCCAGCAAGGAA GGCAGGCACGCCAGGAAGACACCCATGGTGA GAAGTGCAGATGGCCCGAGGGCAAGTTTGCTC AACTCACCCAGGTTTGCTCTTGCTGGGGCCAA GAGGACTCATGTGCCAGGGCCAAGGGCCCTTG GGGGCTCTCACAGGGGGCTTATCTGGGCTTCG GTTCTGGAGGGCCAGGAACAAACAGGCTTCAA AGCCAAGGGCTTGGCTGGCACACAGGGGGCTT GGTCCTTCACCTCTGTCCCCTCTCCCTACGGAC | 21 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| | | | | ACATATAAGACCCTGGTCACACCTGGGAGAGG AGGAGAGGAGAGCATAG-3' | |
| H2B | 8349 | NP_003519.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| RanBP3 isoform 4 | 8498 | NP_001287794.1 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform a | 8498 | NP_003615.2 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform b | 8498 | NP_015559.2 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform d | 8498 | NP_015561.1 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform X1 | 8498 | XP_006722991.1 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA | 22 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| | | | | GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | |
| RanBP3 isoform X1 | 8498 | XP_ 006722992.1 | SMGA DTS | 5'- AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform X1 | 8498 | XP_ 011526695.1 | SMGA DTS | 5'- AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform X1 | 8498 | XP_ 011526694.1 | SMGA DTS | 5'- AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| RanBP3 isoform X1 | 8498 | XP_ 011526696.1 | SMGA DTS | 5'- AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| RanBP3 isoform X1 | 8498 | XP_024307517.1 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| importin 7 | 10527 | NP_006382.1 | SMGA DTS | 5'-AGGCAGACCCAGGGGCCGCATGCAGCAGGGC CTGAGGAGGGAGGTGTGGACGGAGGAGGCCC GCTGCCATTCTTGGTATGGTTCTCACTCCAGGA GCACAGCTGCATCTGGTCTCACTCTGGGCAGC TTATAAGGCCTGGTGTGAGTTTTGTTTATGCAA GTGCAGCATAAAAGGAACAAATCTACCAGCAC CGGGGCTGTTGCCACTGAGTCCTTTTGCATACA TTTTTCAAATGATAACTCACTCTACCCACCCCC CTTCCCTACCCCCAAGGCGATTTATTGAAAAA ACCACCTTATATGGTAATATTGCTAACACACC GTCAGCTGGCCTTTTTAGGGACTTTGTTTAAAG AAGATCCGCCTCTGGGGTTTTATATTGCTCTGG TATTCATGCCAAAGAC-3' | 22 |
| Chx10 | 338917 | NP_878314.1 | SV40 DTS | 5'-GGTGTGGAAAGTCCCCAGGCTCCCCAGCAGGC AGAAGTATGCAAAGCATGCATCTCAATTAGTC AGCAACCA-3' | 4 |
| EBNA-1 | 3783774 | YP_401677.1 | EBV oriP site | 5'-CATGCAGGAAAAGGACAAGCAGCGAAAATTC ACGCCCCTTGGGAGGTGGCGGCATATGCAAA GGATAGCACTCCCACTCTACTACTGGGTATCA TATGCTGACTGTATATGCATGAGGATAGCATA TGCTACCCGGATACAGATTAGGATAGCATATA CTACCCAGATATAGATTAGGATAGCATATGCT ACCCAGATATAGATTAGGATAGCCTATGCTAC CCAGATATAAATTAGGATAGCATATACTACCC AGATATAGATTAGGATAGCATATGCTACCCAG ATATAGATTAGGATAGCCTATGCTACCCAGAT ATAGATTAGGATAGCATATGCTACCCAGATAT AGATTAGGATAGCATATGCTATCCAGATATTT GGGTAGTATATGCTACCCAGATATAAATTAGG ATAGCATATACTACCCTAATCTCTATTAGGATA GCATATGCTACCCGGATACAGATTAGGATAGC ATATACTACCCAGATATAGATTAGGATAGCAT ATGCTACCCAGATATAGATTAGGATAGCCTAT GCTACCCAGATATAAATTAGGATAGCATATAC TACCCAGATATAGATTAGGATAGCATATGCTA CCCAGATATAGATTAGGATAGCCTATGCTACC CAGATATAGATTAGGATAGCATATGCTATCCA GATATTTGGGTAGTATATGCTACCCATGGCAA CATTAGCCCACCGTGCTCTCAGCGACCTCGTG AATATGAGGACCAACAACCCTGTGCTTGGCGC TCAGGCGCAAGTGTGTGTAATTTGTCCTCCAG ATCGCAGCAATCGCGCCCCTATCTTGGCCCGC CCACCTACTTATGCAGGTATTCCCCGGGGTGC CATTAGTGGTTTTGTGGGCAAGTGGTTTGACC GCAGTGGTTAGCGGGGTTACAATCAGCCAAGT TATTACACCCTTATTTTACAGTCCAAAACCGCA GGGCGGCGTGTGGGGGCTGACGCGTGCCCCCA CTCCACAATTTCAAAAAAAGAGTGGCCACTT GTCTTTGTTTATGGGCCCCATTGGCGTGGAGCC CCGTTTAATTTTCGGGGGTGTTAGAGACAACC AGTGGAGTCCGCTGCTGTCGGCGTCCACTCTCT | 23 |

TABLE 2B-continued

Exemplary nuclear import proteins and their corresponding recognition sequences

| Proteins that facilitate nuclear entry | Protein Gene ID | GenBank Accession # for Protein | Name of sequence recognized by protein | Corresponding DNA recognition sequence | SEQ ID NO of Corresponding DNA recognition sequence |
|---|---|---|---|---|---|
| | | | | TTCCCCTTGTTACAAATAGAGTGTAACAACAT<br>GGTTCACCTGTCTTGGTCCCTGCCTGGGACACA<br>TCTTAATAACCCCAGTATCATATTGCACTAGG<br>ATTATGTGTTGCCCATAGCCATAAATTCGTGTG<br>AGATGGACATCCAGTCTTTACGGCTTGTCCCC<br>ACCCCATGGATTTCTATTGTTAAAGATATTCAG<br>AATGTTTCATTCCTACACTAGTATTTATTGCCC<br>AAGGGGTTTGTGAGGGTTATATTGGTGTCATA<br>GCACAATGCCACCACTGAACCCCCCGTCCAAA<br>TTTTATTCTGGGGGCGTCACCTGAAACCTTGTT<br>TTCGAGCACCTCACATACACCTTACTGTTCACA<br>ACTCAGCAGTTATTCTATTAGCTAAACGAAGG<br>AGAATGAAGAAGCAGGCGAAGATTCAGGAGA<br>GTTCACTGCCCGCTCCTTGATCTTCAGCCACTG<br>CCCTTGTGACTAAAATGGTTCACTACCCTCGTG<br>GAATCCTGACCCCATGTAAATAAAACCGTGAC<br>AGCTCATGGGGTGGGAGATATCGCTGTTCCTT<br>AGGACCCTTTTACTAACCCTAATTCGATAGCAT<br>ATGCTTCCCGTTGGGTAACATATGCTATTGAAT<br>TAGGGTTAGTCTGGATAGTATATACTACTACC<br>CGGGAAGCATATGCTACCCGTTTAGGGTTAAC<br>AAGGGGGCCTTATAAACACTATTGCTAATGCC<br>CTCTTGAGGGTCCGCTTATCGGTAGCTACACA<br>GGCCCCTCTGATTGACGTTGGTGTAGCCTCCCG<br>TAGTCTTCCTGGGCCCCTGGGAGGTACATGTC<br>CCCCAGCATTGGTGTAAGAGCTTCAGCCAAGA<br>GTTACACATAAAGGCAATGTTGTGTTGCAGTC<br>CACAGACTGCAAAGTCTGCTCCAGGATGAAAG<br>CCACTCAGTGTTGGCAAATGTGCACATCCATTT<br>ATAAGGATGTCAACTACAGTCAGAGAACCCCT<br>TTGTGTTTGGTCCCCCCCCGTGTCACATGTGGA<br>ACAGGGCCCAGTTGGCAAGTTGTACCAACCAA<br>CTGAAGGGATTACATGCACTGCCCCGC-3' | |
| NKX3-1/3-2 isoform 2 | 4824 | NP_001243268.1 | SMGA DTS | 5'-<br>TTCAAATGATAACTCACTCTACCCACCCCCCTT<br>CCCTACCCCCAAGGCGATTTATTGAAAAAACC<br>ACCTTATATGGTAATATTGCTAACACACCGTC<br>AGCTGGCCTTTTTAGGGACTTTGTTTAAAGAA<br>GATCCGCCTCTGGGGTTTTATATTGCTCTGGTA<br>TTCATGCCAAAGAC-3' | 24 |
| NKX3-1/3-2 isoform 1 | 4824 | NP_006158.2 | SMGA DTS | 5'-<br>TTCAAATGATAACTCACTCTACCCACCCCCCTT<br>CCCTACCCCCAAGGCGATTTATTGAAAAAACC<br>ACCTTATATGGTAATATTGCTAACACACCGTC<br>AGCTGGCCTTTTTAGGGACTTTGTTTAAAGAA<br>GATCCGCCTCTGGGGTTTTATATTGCTCTGGTA<br>TTCATGCCAAAGAC-3' | 19 |

Maintenance Sequence

A DNA construct or sequence disclosed herein may include a maintenance sequence that supports or enables sustained gene expression through successive rounds of cell division and/or progenitor differentiation in host cell for a ssDNA or construct of the invention. In embodiments, a maintenance sequence is a nuclear scaffold/matrix attachment region (S/MAR). S/MAR elements are diverse, AT-rich sequences ranging from 60-500 bp that are conserved across species, thought to anchor chromatin to nuclear matrix proteins during interphase (Bode et al. 2003. *Chromosome Res* 11, 435-445. An S/MARs can be incorporated into an ssDNA or construct described herein to facilitate long-term transgene expression and extra-chromosomal maintenance. In one embodiment, the maintenance sequence is human interferon-beta MAR (5'tataattcactggaattttttgtgtgtatggtatga-catatgggttccettttatttttacatataaatatatttccetgttttttetaaaaaagaaaa agatcatcatttccattgtaaaatgccatatttttttcataggtcacttacata-3' (SEQ ID NO: 39)). In embodiments, S/MARs useful in the constructs described herein can be found by searching the MARome at http://bioinfo.net.in/MARome, described also by Narwade et al. 2019. *Nucleic Acids Research*. Volume 47, Issue 14: 7247-7261.

In embodiments, a ssDNA or construct described herein is capable of replicating in a mammalian cell, e.g., human cell. In some embodiments, a ssDNA or construct described herein is maintained in a host cell, tissue or subject through at least one cell division. For example, a ssDNA or construct described herein is maintained in a host cell, tissue or subject through at least 2, 3, 4, 5, 6, 7, 8, 10, 15, 20, 40, 50 or more cell divisions. In vitro, cell division may be tracked by flow cytometry or microscopy. In vivo, cell division may be tracked by intravital microscopy.

Second Strand Motif

A DNA construct or ssDNA sequence disclosed herein may also include a second strand motif. An example of a SSM is derived from a virus or mobile genetic element. In some embodiments the SSM is an inverted repeat or hairpin sequence, e.g., an inverted terminal repeat (ITR) from a virus, e.g., from an AAV, or a conserved 8-nucleotide hairpin in the anellovirus origin of replication Examples of SSM's are listed below in Table 3:

TABLE 3

Exemplary second strand motifs

| SSM Name | Sequence |
|---|---|
| AAV2 WT ITR-Left | 5'cctgcaggcagctgcgcgctcgctcgctcactgag gccgcccgggcaaagcccgggcgtcgggcgacctttg gtcgcccggcctcagtgagcgagcgagcgcgcagaga gggagtggccaactccatcactaggggttcct-3' (SEQ ID NO: 25) |
| AAV2 WT ITR-Right | 5'aggaaccctagtgatggagttggccactccctct ctgcgcgctcgctcgctcactgaggccgggcgaccaa aggtcgcccgacgcccgggctttgcccgggcggctc agtgagcgagcgagcgcgcagctgcctgcagg-3' (SEQ ID NO: 26) |
| AAV2 Modified ITR-Left | 5'cctgcaggcagctgcgcgctcgctcgctcactgag gccgcccgggcaaagcccgggcgtcgggcgacctttg gtcgcccggcctcagtgagcgagcgagcgcgcagaga gggagtggccaa-3' (SEQ ID NO: 27) |
| AAV2 Modified ITR-Right | 5'ttggccactccctctctgcgcgctcgctcgctcac tgaggccgggcgaccaaaggtcgcccgacgcccgggc tttgcccggggcggcctcagtgagcgagcgagcgcgca gctgcctgcagg-3' (SEQ ID NO: 28) |
| Anellovirus Hairpin-Long | 5'cccgagggcgggtgccgaaggtgagtttacacacc gaagtcaaggggcaattcgggctcgggactggccggg ctatgggc-3' (SEQ ID NO: 29) |
| Anellovirus Hairpin-Short | 5'-agtttaca-3' |

In some embodiments, an SSM is a short sequence of RNA or DNA that is complimentary to a region of the ssDNA, e.g., an RNA primer or a DNA primer. In some embodiments, the primer is a splint sequence connecting ends of a ssDNA described herein. In some embodiments the RNA or DNA primer is less than 100, 75, 50, 40, 30, 25, 20, 15, 10, or 5 nucleotides. In some embodiments the RNA or DNA primer is between 5-100 nucleotides, between 10-100 nucleotides, between 20-80 nucleotides, between 20-60 nucleotides.

Other Elements

A ssDNA construct or sequence disclosed herein may also include other control elements operably linked to the effector sequence, e.g., the sequence encoding an effector, in a manner which permits its transport, localization, transcription, translation and/or expression in a target cell, or which promotes its degradation or repression of expression in a non-target cell. As used herein, "operably linked" sequences include both expression control sequences that are contiguous with the sequence encoding the effector and expression control sequences that act in trans or at a distance to control the sequence encoding the effector. The precise nature of regulatory sequences needed for gene expression in host cells may vary between species, tissues or cell types, but in general may include, as necessary, 5' non-transcribed and 5' non-translated sequences involved with the initiation of transcription and translation. Respectively, such as a TATA box, capping sequence, CAAT sequence, enhancer elements and the like. Regulatory sequences may also include enhancer sequences or upstream activator sequences as desired. The constructs described herein may optionally include 5' leader or signal sequences.

Modified Nucleotides

The DNA constructs and compositions described herein, whether linear or circular, e.g., covalently closed, may have chemical modifications of the nucleobases, sugars, and/or the phosphate backbone. While not wishing to be bound by theory, such modifications can be useful for protecting a DNA from degradation (e.g., from exonucleases) or from the immune system of a host tissue or subject. In general, a modified nucleotide has the same base-pairing specificity as the unmodified nucleotide, i.e., a modified adenine "A" can base-pair with thymine "T". One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage.

In some embodiments, the ssDNA comprises at least one covalent modification. Suitable modifications are described by Sood et al. 2019. DNAmod: the DNA modification database. J Cheminform 11, 30. DNAmod is an open-source database (https://dnamod.hoffmanlab.org) that catalogues DNA modifications and provides a single source to learn about their properties. DNAmod provides a web interface to easily browse and search through these modifications. The database annotates the chemical properties and structures of all curated modified DNA bases, and a much larger list of candidate chemical entities. DNAmod includes manual annotations of available sequencing methods, descriptions of their occurrence in nature, and provides existing and suggested nomenclature. Examples of DNA modifications useful in the methods described herein include, e.g., N6-Methyladenosine (m6A, 6 mA); 5-Formylcytosine (5fC, f5C); 5-carboxylcytosine (ca5C, 5caC); 5-hydroxymethyl-cyotsine (5hmC, hm5C); 5-methyldeoxycytosine (m5dC); 5-methylcytosine (5mC, m5C); 5'-methylcytosine; 3-methylcytosine (m3C); 5-methyl pyrimidine; 8-oxoguanine (8-oxoG); phosphorothioate; S and R phsophorothioate linkages; methylthymine; N3'-P5' Phosphoroamidate (NP); cyclohexane nucleic acid (CeNA); tricyclo-DNA (tcDNA). See, e.g., Pu et al. 2020. An in-vitro DNA phosphorothioate modification reaction. *Mol Microbiol.* 113: 452-463; Zheng & Sheng. 2021. Synthesis of N4-methylcytidine (m4C) and N4,N4-dimethylcytidine (m42C) modified RNA. *Current Protocols,* 1, e248; Ohkubo et al. 2021. Chemical synthesis of modified oligonucleotides containing 5'-amino-5'-deoxy-5'-hydroxymethylthymidine residues. *Current Protocols,* 1, e70; Bao & Xu. 2021. Observation of Z-DNA structure via the synthesis of oligonucleotide DNA containing 8-trifluoromethyl-2-deoxyguanosine. *Current Protocols,* 1, e28; Skakuj et al. 2020. Automated synthesis and purification of guanidine-backbone oligonucleotides. *Current Protocols in Nucleic Acid Chemistry,* 81, e110.

In some embodiments, the ssDNA compositions described herein may include one or both of S phosphorothioate modified nucleotide linkages and R phosphorothioate modified nucleotide linkages. In one embodiment the phosphorothioate linkages are made according to Iwamoto et al, 2017, *Nature Biotechnology,* Volume 35:845-851. Briefly, monomers of nucleoside 3'-oxazaphospholidine derivates undergo stereocontrolled oligonucleotide synthesis with iterative capping and sulfurization to create stereocontrolled phosphorothioate linkages. The final sample may be analyzed by reverse-phase high-performance liquid chromatography (RP-HPLC) and Ultraperformance liquid chromatography mass spectrometry (UPLC/MS) to determine stereochemistry of the modification. Nucleic acids containing phosphorothioate linkages are also commercially available.

In some embodiments, the ssDNA compositions described herein may include one or more boranophosphate modified nucleotides, e.g., following the methods in Sergueev and Shaw, 1998, *J Am Chem Soc*, Volume 120, Issue 37:9417-9427. Briefly, in some embodiments, H-phosphonate chain elongation is followed by boronation to substitute a borano group for a nonbridging oxygen in the phosphate backbone. The final sample may be purified and analyzed by RP-HPLC to determine stereochemistry of the modification. Boranophosphate modified nucleotides are also commercially available.

In some embodiments, the ssDNA compositions described herein may include one or more 5-methylcytosine modified nucleotides, e.g., made following the methods in Lin et al, 2002, *Mol Cell Biol*, Volume 22, Issue 3:704-723. Briefly, in some embodiments, cytosine or the sequence containing cytosine is incubated with glutathione S-transferase fusion of wild-type Dnmt3a (GST-3a) protein using unlabeled S-adenosylmethionine (AdoMet). The nucleotides may be purified and analyzed by HPLC to determine that the nucleotides are methylated at the correct position. 5-methylcytosine modified nucleotides are also available commercially.

In some embodiments, the ssDNA compositions described herein may include one or more 7-methylguanine modified nucleotides. In some embodiments, 7-methylguanine modified nucleotides are made following the methods in Jones and Robins, 1963, Purine nucleosides. III. Methylation studies of certain naturally occurring purine nucleosides, *J Am Chem Soc*, Volume 85:193. Briefly, in some embodiments, 2'-deoxyguanosine in dimethyl sulfoxide is treated with methyl iodide. The nucleotides may be purified and analyzed by HPLC to determine that the nucleotides are methylated at the correct position. In another embodiment, 7-methylguanine modified nucleotides are made according to the methods described in Hendler et al, 1970, Volume 9, Issue 21:4141:4153, and Kore and Parmar, 2006, *Biochemistry*, Volume 25, Issue 3:337-340. Briefly, in some embodiments, instead of guanosine 5'-diphosphate, guanine 5'-diphosphate in water is added to dimethyl sulfate to yield 7-methyl GDP. The nucleotides are purified and analyzed by HPLC to determine that the nucleotides are methylated at the correct position. 7-methylguanine modified nucleotides are also available commercially.

In embodiments, the ssDNA constructs and compositions described herein comprise between 1-100% modified nucleotides, between 1%-90% modified nucleotides, between 1%-80% modified nucleotides, between 1%-70% modified nucleotides, between 1%-60% modified nucleotides, between 1%-50% modified nucleotides, between 1%-40% modified nucleotides, between 1%-30% modified nucleotides, between 1%-20% modified nucleotides, between 1%-15% modified nucleotides, between 1%-10% modified nucleotides, between 20%-90% modified nucleotides, between 20%-80% modified nucleotides. In embodiments, the ssDNA constructs and compositions described herein comprise at least 1% modified nucleotides, at least 5% modified nucleotides; at least 10% modified nucleotides; at least 15% modified nucleotides; at least 20% modified nucleotides; at least 25% modified nucleotides; at least 30% modified nucleotides; at least 40% modified nucleotides; at least 50% modified nucleotides; at least 60% modified nucleotides; at least 70% modified nucleotides; at least 80% modified nucleotides; at least 85% modified nucleotides; at least 90% modified nucleotides; at least 92% modified nucleotides; at least 95% modified nucleotides; at least 97% modified nucleotides. In embodiments, the ssDNA constructs and compositions described herein comprise modified nucleotides at between 0%-100% of each distinct nucleotide, e.g., 0%-100% modified T nucleotides, 0%-100% modified A nucleotides, 0%-100% modified C nucleotides, and 0%-100% modified G nucleotides for each construct. In embodiments, the ssDNA constructs and compositions described herein comprise modified nucleotides at between 0-100%, 10%-100%, 20%-100%, 30%-100%, 40%-100%, 50%-100%, 60%-100%, 10%-50% of each distinct nucleotide, e.g., between 0-100%, 10%-100%, 20%-100%, 30%-100%, 40%-100%, 50%-100%, 60%-100%, 10%-50% of modified T nucleotides; between 0-100%, 10%-100%, 20%-100%, 30%-100%, 40%-100%, 50%-100%, 60%-100%, 10%-50% of modified A nucleotides; between 0-100%, 10%-100%, 20%-100%, 30%-100%, 40%-100%, 50%-100%, 60%-100%, 10%-50% of modified C nucleotides; or between 0-100%, 10%-100%, 20%-100%, 30%-100%, 40%-100%, 50%-100%, 60%-100%, 10%-50% of modified G nucleotides. For example, a ssDNA construct could contain 100% modified T nucleotides, 50% modified A nucleotides, 0% modified C nucleotides, and 25% modified G nucleotides In embodiments, DNA modification, e.g., modifications described herein, can be introduced in the ssDNA compositions described herein throughout the entire sequence; within an element of a sequence, e.g., an element described herein; at the 5'- or 3'- ends; and/or between the last 10, 8, 6, 5, 4, 3, or 2 nucleotides at the 5'- or 3'- end.

In embodiments, a ssDNA described herein has one or more modification that disrupts the ability of the ssDNA to form a double stranded structure, e.g., a ssDNA described herein has one or more modification on a nucleotide present in a region having intramolecular complementarity. In embodiments, a ssDNA described herein has one or more modification that disrupts base pairing of regions of intramolecular complementarity relative to the unmodified sequence of the ssDNA. In some embodiments the modified nucleotides used herein have a reduced propensity to base-pair with modified nucleotides compared to the propensity of unmodified nucleotides to base pair with unmodified nucleotides. In some embodiments the modified nucleotides used herein have an increased propensity to base-pair with unmodified nucleotides compared to modified nucleotides.

Other modifications are also contemplated. For example, ends of a linear DNA described herein can be modified, e.g., to protect them from exonucleases. For example, one or more dideoxynucleotide residues can be added to the 3' terminus of a linear molecule and/or self-complementary oligonucleotides are ligated to one or both ends. See, for example, Chang, et al. (1987) *Proc. Natl. Acad. Sci. USA* 84:4959-4963; Nehls, et at (1996) *Science* 272:886-889.

In some embodiments, the ssDNA is substantially free of (e.g., free of) biotin.

In some embodiments, a modified ssDNA described herein exhibits decreased recognition by DNA sensors in a host tissue or subject compared to an unmodified ssDNA of the same sequence, e.g., at least 10%, 20%, 30%, 40%, 50%, 60%, 70%, 80%, 90%, 95% or more decreased recognition by DNA sensors in a host tissue or subject compared to an unmodified ssDNA of the same sequence. In some embodiments, a modified ssDNA described herein exhibits decreased degradation by DNA nucleases compared to an unmodified ssDNA of the same sequence, e.g., at least 10%, 20%, 30%, 40%, 50%, 60%, 70%, 80%, 90%, 95% or more decreased degradation by DNA nucleases in a host tissue or subject compared to an unmodified ssDNA. In some embodiments, a modified ssDNA described herein shows decreased activation of the innate immune system in a target/host tissue or subject compared to an unmodified ssDNA of the same sequence, e.g., at least 10%, 20%, 30%, 40%, 50%, 60%, 70%, 80%, 90%, 95% or more decreased activation of the innate immune system in a target/host tissue or subject compared to an unmodified ssDNA of the same sequence. In some embodiments, a modified ssDNA described herein exhibits any of the following properties in a target/host tissue or subject compared to an unmodified ssDNA of the same sequence: increased integration of exogenous construct in genome of target cell; increased retention in a target cell through replication; reduced secondary or tertiary structure formation; reduced interaction with innate immune sensors; reduced interaction with nucleases; enhanced stability; enhanced longevity; reduced toxicity; enhanced delivery; increased expression; increased second strand synthesis; increased transport across membranes; or increased binding to DNA binding moieties such as nuclear DNA binding proteins, transcription factors, chaperones, DNA polymerases. In embodiments, any of the above listed properties is modulated at least 10%, 20%, 30%, 40%, 50%, 60%, 70%, 80%, 90%, 95% or more in a target/host tissue or subject compared to an unmodified ssDNA of the same sequence.

Structure of DNA Constructs

In some embodiments, the ssDNA construct or sequence disclosed herein is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 500 nucleotides, at least about 1000 nucleotides, at least about 2000 nucleotides, at least about 3000 nucleotides, at least about 4000 nucleotides, at least about 5000 nucleotides, at least about 6000 nucleotides, at least about 7000 nucleotides, at least about 8000 nucleotides, at least about 9000 nucleotides, at least about 10,000 nucleotides, at least about 20,000 nucleotides, at least about 30,000 nucleotides, at least about 40,000 nucleotides, at least about 50,000 nucleotides. In some embodiments, the size of a ssDNA construct or sequence disclosed herein is a length sufficient to encode useful polypeptides or RNAs.

A ssDNA construct described herein may be circular, e.g., covalently closed.

A ssDNA construct described herein may have less than a threshold level of intramolecular complementarity or double stranded structures. In one embodiment, the ssDNA does not comprise more than 50, 40, 30, 20, 18, 16, 14, 12, 10, 8, 7, 5, 4, 3, 2, or 1 double stranded region longer than 100, 80, 70, 60, 50, 40, 30, 20 or 10 base pairs, i.e., does not comprise regions of intramolecular complementarity longer than 100, 80, 70, 60, 50, 40, 30, 20 or 10 base pairs. In some embodiments, the ssDNA comprises 1, 2, 3, 4, 5, 7, 8, 10, 21, 14, 15, 18, or 20 double stranded regions, e.g., wherein the double stranded regions are no more than 100, 80, 70, 60, 50, 40, 30, 20 or 10 base pairs. In one embodiment, the ssDNA does not comprise any regions of intramolecular complementarity longer than 100, 80, 70, 60, 50, 40, 30, or 20 base pairs. For example, the ssDNA is not a doggybone structure, i.e., it is not a primarily double stranded, closed ended construct.

In some embodiments, the ssDNA does not form a double stranded structure longer than 100 base pairs. In some embodiments, the ssDNA does not form a double stranded structure longer than 80 base pairs. In some embodiments, the ssDNA does not form a double stranded structure longer than 60 base pairs. In some embodiments, the ssDNA does not form a double stranded structure longer than 50 base pairs. In some embodiments, the ssDNA does not form a double stranded structure longer than 45 base pairs. In some embodiments, the ssDNA does not form a double stranded structure longer than 40 base pairs. In some embodiments, the ssDNA does not form a double stranded structure longer than 35 base pairs. In some embodiments, the ssDNA does not form a double stranded structure longer than 30 base pairs. In some embodiments, the ssDNA does not form a double stranded structure longer than 25 base pairs. In some embodiments, the ssDNA does not form a double stranded structure longer than 20 base pairs. In some embodiments, the ssDNA does not comprise a length of double strandedness that is recognized by Cyclic GMP-AMP synthase (cGAS) in a cell. Without wishing to be bound by theory, cGAS is thought to mediate innate immunity to foreign double stranded DNA.

In some embodiments, the ssDNA does not comprise a first sequence that hybridizes with a second sequence, wherein the first sequence and the second sequence are at least 5, 10, 15, 20, or 25 nt long, and wherein the first sequence and the second sequence are positioned less than 6, 5, 4, 3, 2, or 1 nucleotides apart from each other In one embodiment, double stranded regions formed by a ssDNA described herein is determined as described by Xayaphoummine et al. 2005. Kinefold web serverfor RNA/DNA folding path and structure prediction including pseudoknots and knots. *Nucleic Acids Research*, Volume 33:W605-610. In one embodiment, the Kinefold website (http://kinefold.curie.fr/cgi-bin/form.p1) is used to predict double stranded regions of a construct described herein, using the following parameters:

Sequence to fold: enter and select "DNA sequence"
Stochastic Simulation: Co-transcriptional fold, 3 milliseconds
Simulated molecular time: default
Pseudoknots: not allowed
Entanglements: non crossing
Random seed: 11453

In one embodiment, double stranded regions formed by a ssDNA described herein is determined as described by Lorenz et al. 2011. ViennaRNA Package 2.0. *Algorithms for Molecular Biology*, Volume 6, Article 26. In one embodiment, the RNAFold web server (http://rna.tbi.univie.ac.at//cgi-bin/RNAWebSuite/RNAfold.cgi) is used to predict double stranded regions of a construct described herein, using the following parameters:

Fold algorithms and basic options:
  Minimum free energy (MFE) and partition function (default)
  Avoid isolated base pairs (default)
Advanced folding options:
  Dangling energies on both sides of a helix in any case (default)
  DNA parameters (Matthews model, 2004)
  After conversion of SHAPE reactivities, apply pseudo energies to: Stacked pairs (Deigan et al., 2009) (default)

Slope (m)=1.9; intercept (b)=−0; rescale energy parameters to given temperature=3 (default)

Assume RNA molecule to be circular

Output options

Interactive RNA secondary structure plot (default)

RNA secondary structure plots with reliability annotation (partition function folding only) (default)

Mountain plot (default)

A computational folding of an exemplary single stranded, covalently closed DNA is shown in FIGS. 16A-16D. As can be appreciated, a ssDNA may be predicted to have a significant number of double stranded regions such as hairpins. However, the ssDNA of FIGS. 16A-16D lacks long, uninterrupted stretches of double stranded DNA. More particularly, the longest uninterrupted dsDNA region in FIGS. 16A-16D is no more than 16 nucleotides in length. This construct is not predicted to form a double stranded structure longer than 100 base pairs; rather, bulges, interior loops, and other structures are disposed between shorter double stranded regions.

Production

Figure 1B:
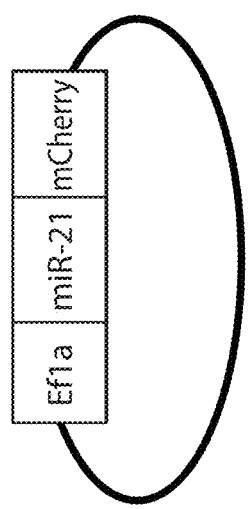
FIG. 1B shows a ssDNA construct comprising a promoter and a sequence encoding a polypeptide effector (in this case, model protein mCherry).
Figure 1A:
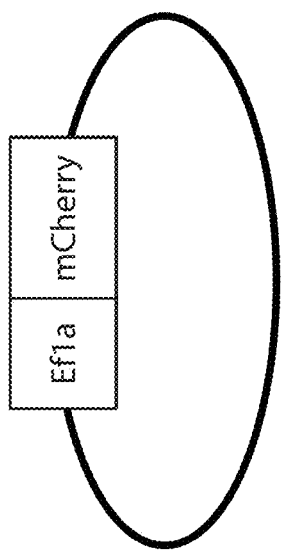
FIGS. 1A-IE are a set of diagrams showing the design of exemplary ssDNAs described herein.
Figure 2:
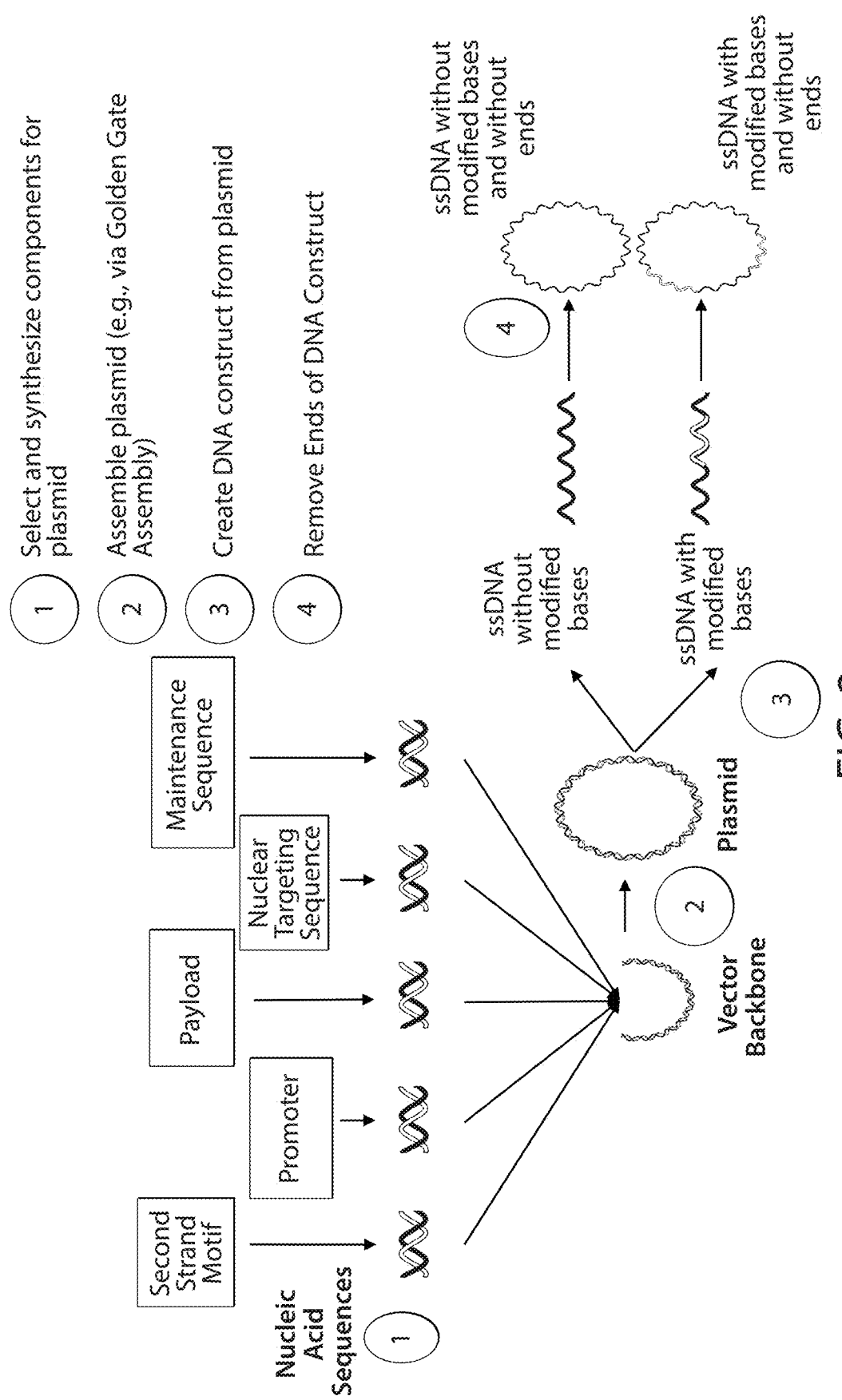
FIG. 2 is a schematic diagram of an exemplary production process of circular ssDNAs described herein.

In general, the ssDNA constructs of the invention are produced from a plasmid assembled to contain the desired elements described herein. The plasmid template can be assembled using Golden Gate cloning for assembly of multiple DNA fragments in a defined linear order in a recipient vector using a one-pot assembly procedure. Golden Gate cloning is described in Marillonnet & Grützner, 2020, Synthetic DNA assembly using golden gate cloning and the hierarchical modular cloning pipeline, *Current Protocols in Molecular Biology*, 130:e115. The template is then used to make a single stranded DNA using Methanol Responsive (MeRPy) PCR, e.g., as described in Minev et al., 2019, *Rapid in vitro production of single-stranded DNA*, *Nucleic Acids Research*, Volume 47, Issue 22:11956-11962. For embodiments in which the ssDNA is circular, the resulting ssDNA can be circularized, e.g., using a DNA ligase. A schematic diagram of an exemplary production process is shown in FIG. 2.

In some embodiments, a method or composition described herein involves a nicking endonuclease. In some embodiments, the endonuclease is naturally occurring. In some embodiments, the endonuclease is mutated or engineered, e.g., derived from an enzyme that causes double-stranded breaks.

In some embodiments, a method described herein comprises the use of, or a composition described herein comprises, Nb.BsrDI. In some embodiments, the Nb.BsrDI comprises the large subunit of the BsrDI restriction gene from *Bacillus stearothermophilus* D70, or an amino acid sequence with at least 80%, 85%, 90%, 95%, 98%, or 99% identity thereto. In some embodiments, the Nb.BsrDI comprises an amino acid sequence according to Genbank accession number ABD15132.1 (herein incorporated by reference in its entirety), or an amino acid sequence with at least 80%, 85%, 90%, 95%, 98%, or 99% identity thereto. In some embodiments, the Nb.BsrDI cleaves at the site indicated in the following sequence:

```
5' . . . G C A A T G N N . . . 3'

3' . . . C G T T A C▲N N . . . 5'.
```

In some embodiments, a digestion reaction utilizing Nb.BsrDI is performed in rCutSmart™ Buffer (NEB). In some embodiments, the digestion reaction is performed in a buffer comprising one or more of (e.g., all of) Potassium Acetate (e.g., at 50 mM), Tris-acetate (e.g., 20 mM), Magnesium Acetate (e.g., 10 mM), or Recombinant Albumin (e.g., 100 μg/ml), wherein optionally, the buffer has a pH of 7.9 when measured at 25° C. In some embodiments, the digestion reaction is performed at 30° C. to 70° C. (e.g., about 37° C. or about 65° C.). In some embodiments, the digestion reaction is performed for 10 minutes to 3 hours (e.g., about 30 minutes or about 1 hour).

In some embodiments, a method described herein comprises the use of, or a composition described herein comprises, Nb.Bpu10I. In some embodiments, the Nb.Bpu10I comprises an amino acid sequence encoded by wild type bpu10IRα or a mutagenized bpu10IRβ gene from *Bacillus pumilus* RFL10, or an amino acid sequence with at least 80%, 85%, 90%, 95%, 98%, or 99% identity thereto. In some embodiments, the Nb.Bpu10I cleaves at the site indicated in the following sequence:

```
5' C C T N A G C 3'

3' G G A N T↑C G 5'
```

In some embodiments, a digestion reaction utilizing Nb.Bpu10I is performed in R Buffer (ThermoFisher Scientific). In some embodiments, the digestion reaction is performed in a buffer comprising one or more of (e.g., all of) Tris-HCl (e.g., 10 mM), MgCl₂ (e.g., 10 mM), KCl (e.g., 100 mM), and BSA (e.g., 0.1 mg/mL). In some embodiments, the digestion reaction is performed at 30° C. to 50° C. (e.g., about 37° C.). In some embodiments, the digestion reaction is performed for 30 minutes to 3 hours (e.g., about 1 hour).

In some embodiments, a method described herein comprises the use of, or a composition described herein comprises, Nt.BspQI. In some embodiments, the Nt.BspQI comprises an engineered BspQI variant from BspQI restriction enzyme, or an amino acid sequence with at least 80%, 85%, 90%, 95%, 98%, or 99% identity thereto. In some embodiments, the Nt.BspQI cleaves at the site indicated in the following sequence:

```
5' . . . G C T C T T C N▼ . . . 3'

3' . . . C G A G A A G N . . . 5'
```

In some embodiments, a digestion reaction utilizing Nt.BspQI is performed in NEBuffer™ r3.1 (NEB). In some embodiments, the digestion reaction is performed in a buffer comprising one or more of (e.g., all of) NaCl (e.g., 100 mM), Tris-HCl (e.g., 50 mM), MgCl₂ (e.g., 10 mM), Recombinant Albumin (e.g., 100 μg/mL), wherein optionally, the buffer has a pH of 7.9 when measured at 25° C. In some embodiments, the digestion reaction is performed at 40° C. to 60° C. (e.g., about 50° C.). In some embodiments, the digestion reaction is performed for 30 minutes to 3 hours (e.g., about 1 hour).

In some embodiments, a method described herein comprises the use of, or a composition described herein comprises, T7 exonuclease. In some embodiments, a digestion reaction utilizing T7 exonuclease is performed in NEBuffer™ 4 (NEB). In some embodiments, the digestion reaction is performed in a buffer comprising one or more of (e.g., all of) Potassium Acetate (e.g., at 50 mM), Tris-acetate (e.g., 20 mM), Magnesium Acetate (e.g., 10 mM), or DTT (e.g., 1 mM), wherein optionally, the buffer has a pH of 7.9 when measured at 25° C. In some embodiments, the digestion reaction is performed at 20° C. to 50° C. (e.g., about 25° C.

or about 37° C.). In some embodiments, the digestion reaction is performed for 15-120 minutes, e.g., 20-60 minutes, e.g., about 30 min.

In some embodiments, a method described herein comprises the use of, or a composition described herein comprises, T5 exonuclease. In some embodiments, a digestion reaction utilizing T5 exonuclease is performed in NEBuffer™ 4 (NEB). In some embodiments, the digestion reaction is performed in a buffer comprising one or more of (e.g., all of) Potassium Acetate (e.g., at 50 mM), Tris-acetate (e.g., 20 mM), Magnesium Acetate (e.g., 10 mM), or DTT (e.g., 1 mM), wherein optionally, the buffer has a pH of 7.9 when measured at 25° C. In some embodiments, the digestion reaction is performed at 30° C. to 50° C. (e.g., about 37° C.). In some embodiments, the digestion reaction is performed for 10 minutes to 3 hours (e.g., about 30 minutes).

In some embodiments, a method described herein comprises the use of, or a composition described herein comprises, Exonuclease III. In some embodiments, a digestion reaction utilizing Exonuclease III is performed in NEBuffer™ 1 (NEB). In some embodiments, the digestion reaction is performed in a buffer comprising one or more of (e.g., all of), Bis-Tris-Propane-HCl (e.g., 10 mM), $MgCl_2$ (e.g., 10 mM), or DTT (e.g., 1 mM), wherein optionally, the buffer has a pH of 7 when measured at 25° C. In some embodiments, the digestion reaction is performed at 30° C. to 50° C. (e.g., about 37° C.). In some embodiments, the digestion reaction is performed for 10 minutes to 3 hours (e.g., about 30 minutes).

In some embodiments, a method described herein comprises the use of, or a composition described herein comprises, a high-fidelity DNA polymerase, e.g., a Q5 High-Fidelity DNA Polymerase (M0491L, New England Biolabs). In some embodiments, a polymerase chain reaction is performed using a high-fidelity DNA polymerase. In some embodiments, the polymerase chain reaction utilizing the Q5 High-Fidelity DNA Polymerase is performed using Q5 Reaction Buffer (NEB).

In some embodiments, a method described herein comprises the use of, or a composition described herein comprises, Exonuclease I. In some embodiments, the Exonuclease I comprises the amino acid sequence of Exo I gene from *E. coli* NM554, or an amino acid sequence with at least 80%, 85%, 90%, 95%, 98%, or 99% identity thereto. In some embodiments, the Exonuclease I catalyzes the removal of nucleotides from linear single-stranded DNA (e.g., in the 3' to 5' direction). In some embodiments, a digestion reaction utilizing Exonuclease I is performed in Exonuclease I Reaction Buffer (NEB). In some embodiments, the digestion reaction is performed in a buffer comprising one or more of (e.g., all of) Glycine-KOH (e.g., at 67 mM), or $MgCl_2$ (e.g., at 6.7 mM), β-ME (e.g., at 10 mM), wherein optionally, the buffer has a pH of 9.5 when measured at 25° C. In some embodiments, the digestion reaction is performed at 30° C. to 50° C. (e.g., about 37° C.). In some embodiments, the digestion reaction is performed for 10 minutes to 3 hours (e.g., about 30 minutes). In some embodiments, the circular ssDNA is resistant to degradation by Exonuclease I.

In some embodiments, the circularization efficiency of the circularization methods provided herein is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or more.

The ssDNA or circular, e.g., covalently closed, ssDNA may be enriched or purified from impurities or byproducts selected from the group consisting of: endotoxin, mononucleotides, modified mononucleotides, double stranded DNA, linear DNA (for circular products), proteins (e.g., enzymes, e.g., ligases, restriction enzymes), DNA fragments or truncations. In some embodiments, the purified ssDNA is substantially free of process byproducts and impurities, e.g., process byproducts or impurities described herein.

The ssDNA or circular, e.g., covalently closed, ssDNA may be sequenced to confirm the desired, designed sequence. In embodiments, other structural analysis of the ssDNA (e.g., restriction enzyme analysis) may be performed to confirm or verify its sequence.

Purity

In some embodiments, a composition comprising ssDNA described herein has a certain purity. For instance, in some embodiments, at least 70%, 80%, 85%, 90%, 95%, or 99% by mass of total DNA in the composition may be the covalently closed ssDNA. As an example, the composition may also comprise linear DNA or circular dsDNA, e.g., as a contaminant.

In some embodiments, a composition described herein (e.g., a composition comprising circular ssDNA, e.g., a pharmaceutical composition comprising circular ssDNA or a manufacturing intermediate comprising circular ssDNA) is free of or is substantially free of one or more contaminant, e.g., as described in this section. In some embodiments, a method described herein (e.g., a method of making circular ssDNA) results in a composition that is free of or is substantially free of one or more contaminant, e.g., as described in this section. In some embodiments, a method described herein (e.g., a method of making circular ssDNA) comprises a step of assaying for one or more contaminant, e.g., as described in this section. In some embodiments, the method comprises approving or releasing a batch if the batch is free of or substantially free of the contaminant.

In some embodiments, the contaminant comprises a non-human animal serum (e.g., fetal bovine serum); an enzyme, e.g., a ligase, a polymerase, or a digestive enzyme (e.g., a trypsin, a collagenase, a DNase, a RNase, an exonuclease, or an endonuclease, e.g., a restriction endonuclease); a growth factor; a cytokine; an antibody (e.g., a monoclonal antibody); a bead (e.g., an antibody-coated bead); an antibiotic; a cell culture medium; a component of a cell culture medium; a detergent; a protein, e.g., a host cell protein; an extraneous nucleic acid sequence (e.g., a mononucleotide (e.g., a modified mononucleotide), or a DNA fragment or truncation; helper virus contaminant (e.g., infectious virus, viral DNA, or viral proteins); or a solvent; a cellular debris; a cell; a pyrogen; a fungus; or any combination thereof, or a portion of any of the foregoing. In some embodiments, the contaminant was a component introduced during a manufacturing process.

In some embodiments, the contaminant comprises an agent for transmissible spongiform encephalopathy (TSE). In some embodiments, a test for this contaminant is performed on a composition for which an bovine material, was used in manufacturing.

In some embodiments, the contaminant comprises a zoonotic virus, a porcine circovirus 1, a porcine circovirus 2, or a porcine parvovirus; or any combination thereof, or a portion of any of the foregoing. In some embodiments, a test for this contaminant is performed on a composition for which non-human animal material, e.g., a porcine material was used in manufacturing.

In some embodiments, the contaminant comprises a virus or portion thereof, e.g., a human virus; human immunodeficiency virus (HIV); HIV-1; HIV-2; hepatitis B virus (HBV); hepatitis C virus (HCV); human TSE, including Creutzfeldt-Jakob disease (CJD); variant CJD (vCJD); *Treponema pallidum* (syphilis); human T-lymphotropic virus (HTLV), HTLV-1, HTLV-2; or cytomegalovirus, human herpesvirus (e.g., - human herpesvirus -6, -7 or -8 (HHV-6, -7& -8)), JC virus, BK virus, Epstein-Barr virus (EBV), human parvovirus B19, human papillomavirus (HPV); an adenovirus, e.g., adenovirus E1; SV40 Large T antigen sequence; HPV E6 or E7 DNA; or any combination thereof, or a portion of any of the foregoing. In some embodiments, a test for this contaminant is performed on a composition for which human donor cells (e.g., leukocyte-rich cells) were used in manufacturing. In some embodiments, a test for this contaminant is performed on a cell bank.

In some embodiments, the contaminant comprises a microbe or a portion thereof, a bacterium (e.g., a Gram-negative bacterium); *mycoplasma*; spiroplasma (e.g., when insect cells are used); bacterial toxin (e.g., endotoxin); or an adventitious agent, e.g., an adventitious viral agent or a non-viral adventitious agent, or any combination thereof, or a portion of any of the foregoing. In some embodiments, the contaminant comprises a simian virus, e.g., simian polyomavirus SV40 or simian retrovirus, or any combination thereof, or a portion of any of the foregoing. In some embodiments, the contaminant comprises an arbovirus. In some embodiments, the contaminant comprises a bacteriophage. In some embodiments, a test for this contaminant is performed on a cell bank, e.g., a cell bank of bacterial cells.

In some embodiments, the contaminant comprises DNA from a host cell, e.g., wherein the host cell is a non-tumorigenic cell. In some embodiments, the DNA is present at a level of less than 10 ng/dose. In some embodiments, the DNA size is below about 200 nucleotides in length.

In some embodiments, the contaminant is an endotoxin. In some embodiments, a level of the endotoxin is less than 5 Endotoxin Unit (EU)/kg body weight/hour, e.g., wherein the composition is formulated for parenteral administration. In some embodiments, a level of the endotoxin is less than 0.2 EU/kg body weight/hour, e.g., wherein the composition is formulated for intrathecal administration. In some embodiments, a level of the endotoxin is not more than 2.0 EU/dose/eye, e.g., wherein the composition is formulated for injection or implantation into the eye, or not more than 0.5 EU/mL, e.g., wherein the composition is formulated for intraocular administration.

In some embodiments, the contaminant comprises an organic solvent, e.g., an aromatic organic solvent, e.g., phenol or chloroform.

In some embodiments, the contaminant is a contaminant described in Chemistry, Manufacturing, and Control (CMC) Information for Human Gene Therapy Investigational New Drug Applications (INDs)—Guidance for Industry (U.S. Department of Health and Human Services, Food and Drug Administration, Center for Biologics Evaluation and Research, January 2020), which is herein incorporated by reference in its entirety.

In some embodiments, the composition is substantially free of (e.g., is free of) a polymerase. In some embodiments, the composition is substantially free of (e.g., is free of) a polymerase that performs rolling circle amplification. In some embodiments, the composition is substantially free (e.g., is free of) LNPs. In some embodiments, the composition is substantially free (e.g., is free of) nanoparticles.

In some embodiments, the composition is substantially free of (e.g., is free of) agarose. In some embodiments, the composition is substantially free of (e.g., is free of) acrylamide.

In some embodiments, the composition is substantially free of (e.g., is free of) polypeptides.

In some embodiments, the ratio of the number of molecules of the covalently closed ssDNA to other DNA molecules in the composition is at least 10:1, 20:1, 50:1, 80:1, 90:1, 100:1, 200:1, 500:1, or 1000:1. In some embodiments, the composition is substantially free of DNA from a host cell, e.g., DNA is present at a level of less than 10 ng/dose. In some embodiments, the composition is substantially free of DNA having a size of below about 200 nucleotides in length. In some embodiments, the composition is substantially free of individual nucleotides. In some embodiments, the ratio of covalently closed ssDNA to dsDNA in the composition is at least 100:1, 200:1, 500:1, or 1000:1. In some embodiments, at least 70%, 80%, 85%, 90%, 95%, or 99% of DNA by mass (or by copy number) in the composition is full length.

Pharmaceutical Compositions

The present disclosure includes ssDNA and related compositions in combination with one or more pharmaceutically acceptable excipients and/or carriers.

Pharmaceutical compositions may optionally comprise one or more additional active substances, e.g., therapeutically and/or prophylactically active substances. Pharmaceutical compositions of the present invention are generally sterile and/or pyrogen-free.

A ssDNA or construct described herein may be formulated without a carrier, e.g., the ssDNA or construct described herein may be administered to a host cell, tissue or subject "naked". A naked formulation may include pharmaceutical excipients or diluents but lacks a carrier.

Pharmaceutically acceptable excipients or diluents may comprise an inactive substance that serves as a vehicle or medium for the compositions described herein, such as any one of the inactive ingredients approved by the United States Food and Drug Administration (FDA) and listed in the Inactive Ingredient Database, which is incorporated by reference herein. Non-limiting examples of pharmaceutically acceptable excipients or diluents include solvents, aqueous solvents, non-aqueous solvents, tonicity agents, dispersion media, cryoprotectants, diluents, suspension aids, surface active agents, isotonic agents, thickening agents, emulsifying agents, preservatives, hyaluronidases, dispersing agents, preservatives, lubricants, granulating agents, disintegrating agents, binding agents, antioxidants, buffering agents (e.g., phosphate buffered saline (PBS)), lubricating agents, oils, and mixtures thereof.

General considerations in the formulation and/or manufacture of pharmaceutical agents may be found, for example, in *Remington: The Science and Practice of Pharmacy* 21st ed., Lippincott Williams & Wilkins, 2005 (incorporated herein by reference).

Carriers

A ssDNA or construct described herein may also be formulated, or included, with a carrier. General considerations of carriers and delivery of pharmaceutical agents may be found, for example, in Delivery Technologies for Biopharmaceuticals: Peptides. Proteins. Nucleic Acids and Vaccines (Lene Jorgensen and Hanne Morck Nielson, Eds.) Wiley; 1st edition (Dec. 21, 2009); and Vargason et al. 2021. *Nat Biomed Eng* 5, 951-967.

Non-limiting examples of carriers include carbohydrate carriers (e.g., an anhydride-modified phytoglycogen or glycogen-type material, GalNAc), nanoparticles (e.g., a nanoparticle that encapsulates or is covalently linked to the ssDNA, gold nanoparticles, silica nanoparticles), lipid particles (e.g., liposomes, lipid nanoparticles), cationic carriers (e.g., a cationic lipopolymer or transfection reagent), fusosomes, non-nucleated cells (e.g., ex vivo differentiated reticulocytes), nucleated cells, exosomes, protein carriers (e.g., a protein covalently linked to the ssDNA), peptides (e.g., cell-penetrating peptides), materials (e.g., graphene oxide), single pure lipids (e.g., cholesterol), DNA origami (e.g., DNA tetrahedron).

In one embodiment, the ssDNA compositions, constructs and systems described herein can be formulated in liposomes or other similar vesicles. Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Vesicles can be made from several different types of lipids; however, phospholipids are most commonly used to generate liposomes as drug carriers. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

Exosomes can also be used as drug delivery vehicles for the compositions and systems described herein. For a review, see Ha et al. July 2016. Acta Pharmaceutica Sinica B. Volume 6, Issue 4, Pages 287-296; https://doi.org/10.1016/j.apsb.2016.02.001.

Ex vivo differentiated red blood cells can also be used as a carrier for an agent (e.g., an ssDNA) described herein. See, e.g., WO2015073587; WO2017123646; WO2017123644; WO2018102740; wO2016183482; WO2015153102; WO2018151829; WO2018009838; Shi et al. 2014. Proc Natl Acad Sci USA. 111(28): 10131-10136; U.S. Pat. No. 9,644,180; Huang et al. 2017. Nature Communications 8: 423; Shi et al. 2014. Proc Natl Acad Sci USA. 111(28): 10131-10136.

Fusosome compositions, e.g., as described in WO2018208728, can also be used as carriers to deliver the ssDNAs described herein.

Lipid Nanoparticles:

Lipid nanoparticles (LNPs) are carriers made of ionizable lipids. LNPs are taken up by cells via endocytosis, and their properties allow endosomal escape, which allows release of the cargo into the cytoplasm of a target cell. In addition to ionizable lipids, LNPs may contain a helper lipid to promote cell binding, cholesterol to fill the gaps between the lipids, and/or a polyethylene glycol (PEG) to reduce opsonization by serum proteins and reticuloendothelial clearance. Lipid nanoparticles, in some embodiments, comprise one or more ionic lipids, such as non-cationic lipids (e.g., neutral or anionic, or zwitterionic lipids); one or more conjugated lipids (such as PEG-conjugated lipids or lipids conjugated to polymers described in Table 5 of WO2019217941; incorporated herein by reference in its entirety); one or more sterols (e.g., cholesterol); and, optionally, one or more targeting molecules (e.g., conjugated receptors, receptor ligands, antibodies); or combinations of the foregoing.

Lipids that can be used in nanoparticle formations (e.g., lipid nanoparticles) include, for example those described in Table 4 of WO2019217941, which is incorporated by reference—e.g., a lipid-containing nanoparticle can comprise one or more of the lipids in Table 4 of WO2019217941. Lipid nanoparticles can include additional elements, such as polymers, such as the polymers described in Table 5 of WO2019217941, incorporated by reference.

In some embodiments, conjugated lipids, when present, can include one or more of PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy)propyl-1-0-(w-methoxy(polyethoxy)ethyl) butanedioate (PEG-S-DMG)), PEG dialkoxypropylcarbam, N-(carbonyl-methoxypoly ethylene glycol 2000)-1,2-distearoyl-sn-glycero-3-phosphoethanolamine sodium salt, and those described in Table 2 of WO2019051289 (incorporated by reference), and combinations of the foregoing.

In some embodiments, sterols that can be incorporated into lipid nanoparticles include one or more of cholesterol or cholesterol derivatives, such as those in WO2009/127060 or US2010/0130588, which are incorporated by reference. Additional exemplary sterols include phytosterols, including those described in Eygeris et al (2020), dx.doi.org/10.1021/acs.nanolett.Oc01386, incorporated herein by reference.

In some embodiments, the lipid particle comprises an ionizable lipid, a non-cationic lipid, a conjugated lipid that inhibits aggregation of particles, and a sterol. The amounts of these components can be varied independently and to achieve desired properties. For example, in some embodiments, the lipid nanoparticle comprises an ionizable lipid is in an amount from about 20 mol % to about 90 mol % of the total lipids (in other embodiments it may be 20-70% (mol), 30-60% (mol) or 40-50% (mol); about 50 mol % to about 90 mol % of the total lipid present in the lipid nanoparticle), a non-cationic lipid in an amount from about 5 mol % to about 30 mol % of the total lipids, a conjugated lipid in an amount from about 0.5 mol % to about 20 mol % of the total lipids, and a sterol in an amount from about 20 mol % to about 50 mol % of the total lipids. The ratio of total lipid to nucleic acid can be varied as desired. For example, the total lipid to nucleic acid (mass or weight) ratio can be from about 10:1 to about 30:1.

In some embodiments, the lipid to nucleic acid ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of lipids and nucleic acid can be adjusted to provide a desired N/P ratio, for example, N/P ratio of 3, 4, 5, 6, 7, 8, 9, 10 or higher. Generally, the lipid nanoparticle formulation's overall lipid content can range from about 5 mg/ml to about 30 mg/mL.

Some non-limiting example of lipid compounds that may be used (e.g., in combination with other lipid components) to form lipid nanoparticles for the delivery of compositions described herein, e.g., nucleic acid (e.g., RNA) described herein includes,

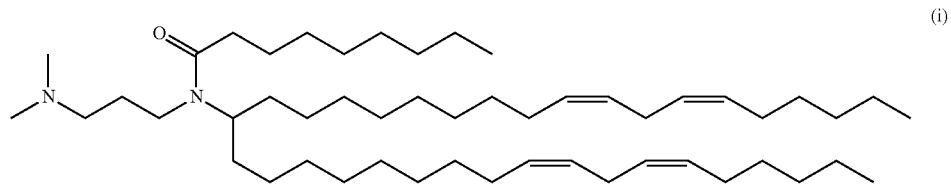 [SMILES: CCCCC/C=C\C/C=C\CCCCCCCCC(CCCCCCCC/C=C\C/C=C\CCCCC)N(CCCN(C)C)C(=O)CCCCCCCC]

(i)

In some embodiments an LNP comprising Formula (i) is used to deliver a DNA composition described herein to the liver and/or hepatocyte cells.

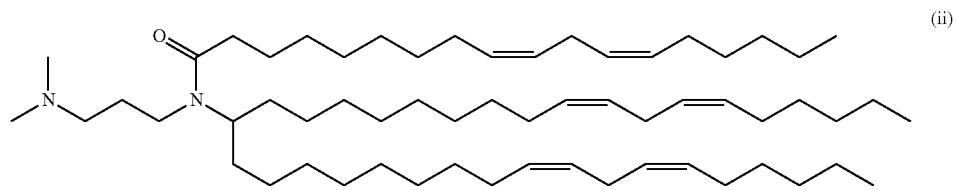 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC]

(ii)

In some embodiments an LNP comprising Formula (ii) is used to deliver a DNA composition described herein to the liver and/or hepatocyte cells.

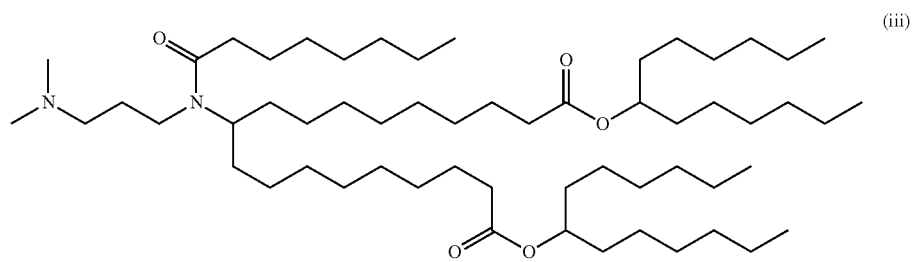 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

(iii)

In some embodiments an LNP comprising Formula (iii) is used to deliver a DNA composition described herein to the liver and/or hepatocyte cells.

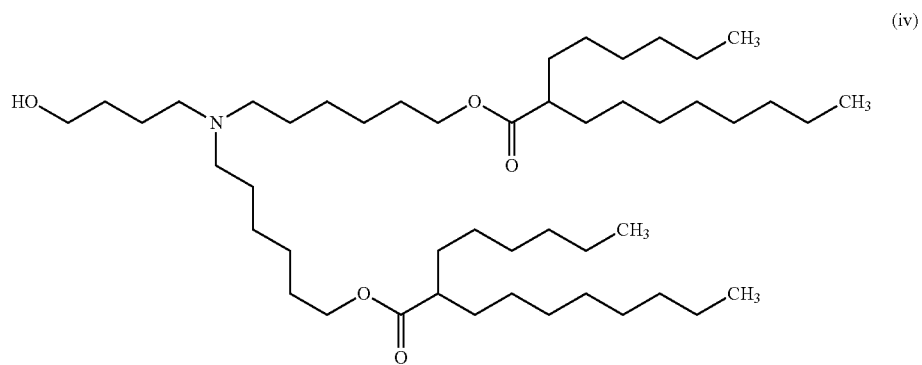

(iv)

-continued (v)

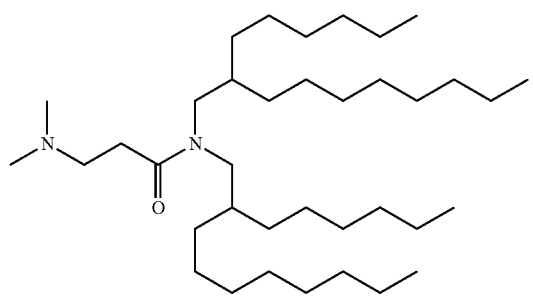

In some embodiments an LNP comprising Formula (v) is used to deliver a DNA composition described herein to the liver and/or hepatocyte cells.

(vi)

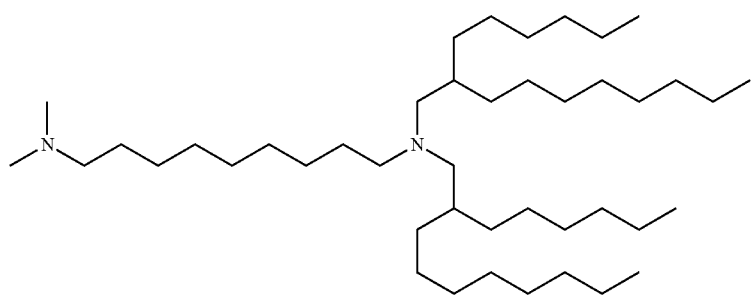

n some embodiments an LNP comprising Formula (vi) is used to deliver a DNA composition described herein to the liver and/or hepatocyte cells.

(vii)

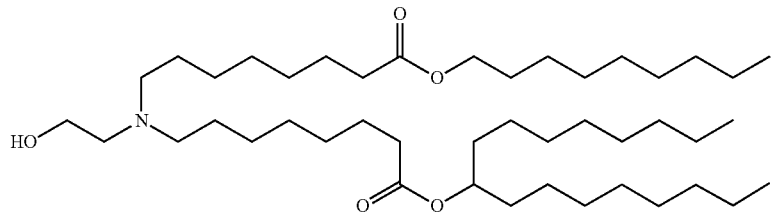

(viii)

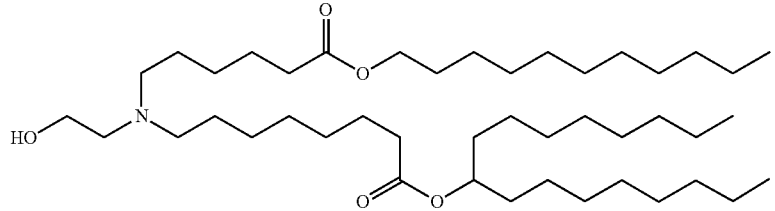

In some embodiments an LNP comprising Formula vii or (viii) is used to deliver a DNA composition described herein to the liver and/or hepatocyte cells.

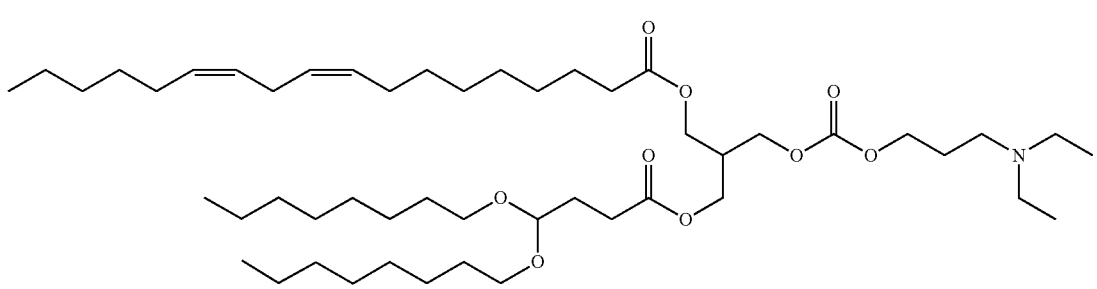
(ix)

In some embodiments an LNP comprising Formula (ix) is used to deliver a DNA composition described herein to the liver and/or hepatocyte cells.

In some embodiments an LNP comprising Formula (x) is used to deliver a DNA composition described herein to the liver and/or hepatocyte cells:

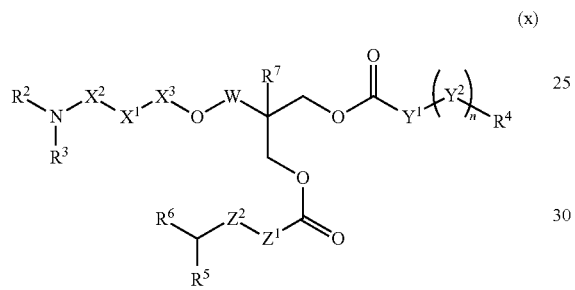
(x)

wherein
$X^1$ is O, $NR^1$, or a direct bond, $X^2$ is C2-5 alkylene, $X^3$ is C(=O) or a direct bond, $R^1$ is H or Me, $R^3$ is Ci-3 alkyl, $R^2$ is Ci-3 alkyl, or $R^2$ taken together with the nitrogen atom to which it is attached and 1-3 carbon atoms of $X^2$ form a 4-, 5-, or 6-membered ring, or $X^1$ is $NR^1$, $R^1$ and R2 taken together with the nitrogen atoms to which they are attached form a 5- or 6-membered ring, or $R^2$ taken together with $R^3$ and the nitrogen atom to which they are attached form a 5-, 6-, or 7-membered ring, $Y^1$ is C2-12 alkylene, $Y^2$ is selected from

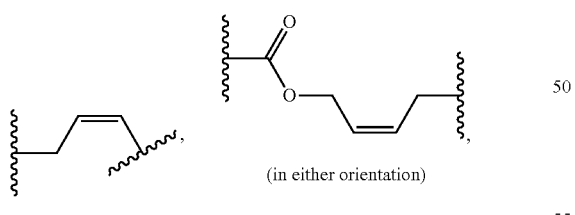

(in either orientation)

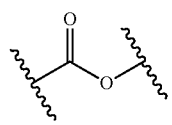 [SMILES: *OC(*)=O]

(in either orientation)

n is 0 to 3, $R^4$ is Ci-15 alkyl, $Z^1$ is Ci-6 alkylene or a direct bond, $Z^2$ is

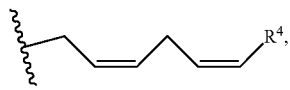

(in either orientation) or absent, provided that if $Z^1$ is a direct bond, $Z^2$ is absent;

$R^5$ is C5-9 alkyl or C6-10 alkoxy, $R^6$ is C5-9 alkyl or C6-10 alkoxy, W is methylene or a direct bond, and $R^7$ is H or Me, or a salt thereof, provided that if $R^3$ and $R^2$ are C2 alkyls, $X^1$ is O, $X^2$ is linear C3 alkylene, $X^3$ is C(=O), $Y^1$ is linear Ce alkylene, $(Y^2)n$-$R^4$ is $R^4$ is linear C5 alkyl, $Z^1$ is C2 alkylene, $Z^2$ is absent, W is methylene, and $R^7$ is H, then $R^5$ and $R^6$ are not Cx alkoxy.

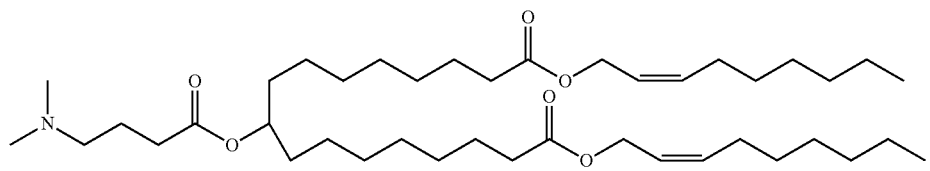
(xi)

In some embodiments an LNP comprising Formula (xi) is used to deliver a DNA composition described herein to the liver and/or hepatocyte cells.

In some embodiments an LNP comprising Formula (xii) is used to deliver a DNA composition described herein to the liver and/or hepatocyte cells.

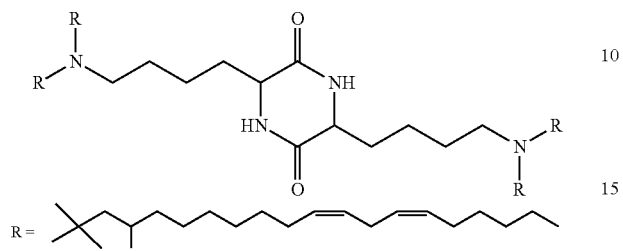

OF-02 where

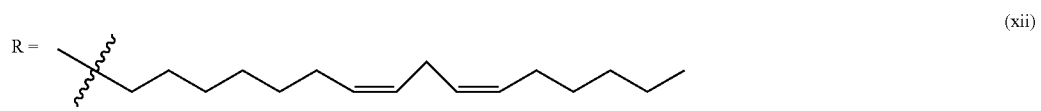
(xii)

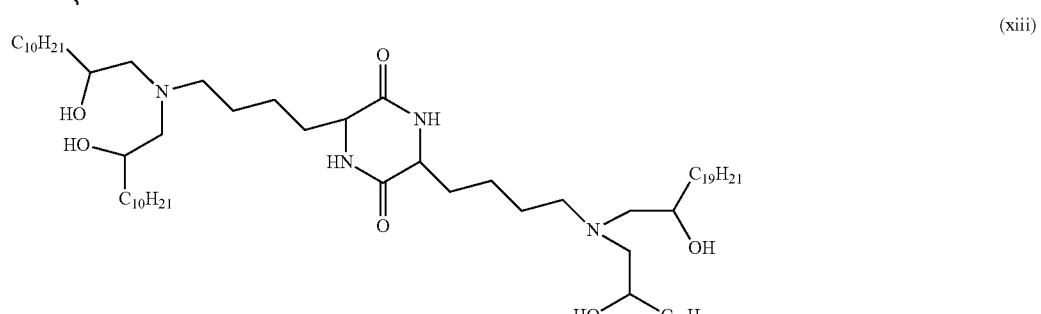
(xiii)

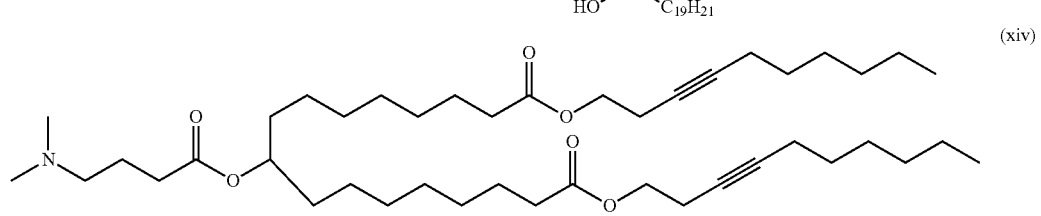
(xiv)

In some embodiments an LNP comprises a compound of Formula (xiii) and a compound of Formula (xiv).

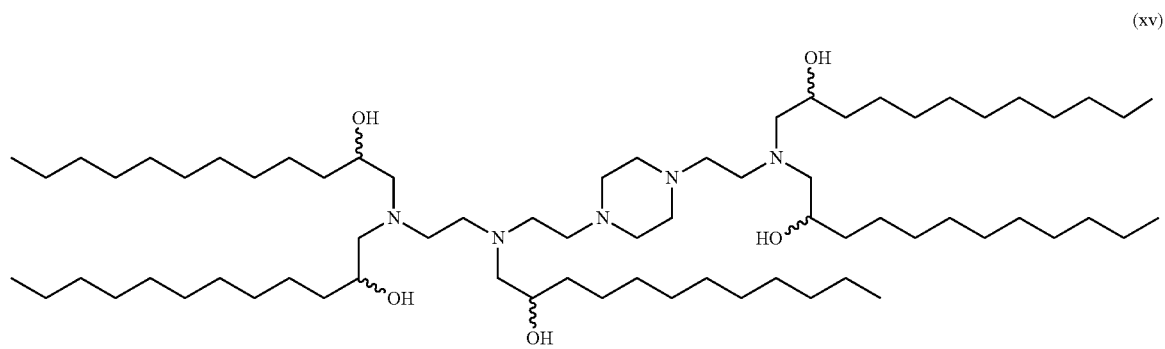 [SMILES: CCCCCCCCCCC(O)CN(CCN1CCN(CCN(CC(O)CCCCCCCCCC)CC(O)CCCCCCCCCC)CC1)CCN(CC(O)CCCCCCCCCC)CC(O)CCCCCCCCCC]
(xv)

In some embodiments an LNP comprising Formula (xv) is used to deliver a DNA composition described herein to the liver and/or hepatocyte cells.

(xvi)

In some embodiments an LNP comprising a formulation of Formula (xvi) is used to deliver a DNA composition described herein to the lung endothelial cells.

In some embodiments an LNP comprising a formulation of Formula (xvii), xviii or xix is used to deliver a DNA composition described herein to the lung endothelial cells.

(xvii)

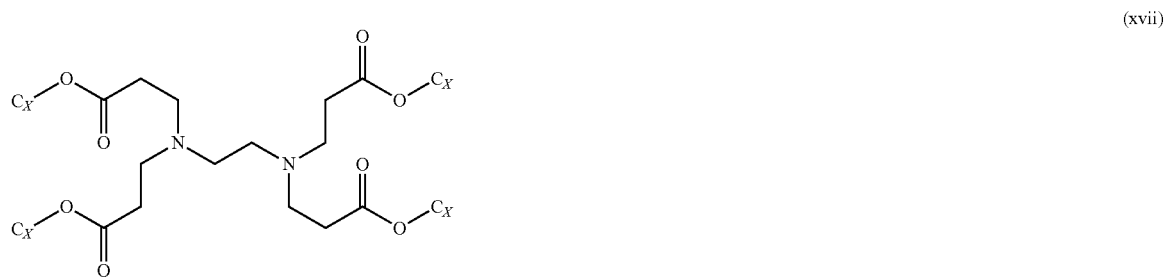

(xviii)(a)

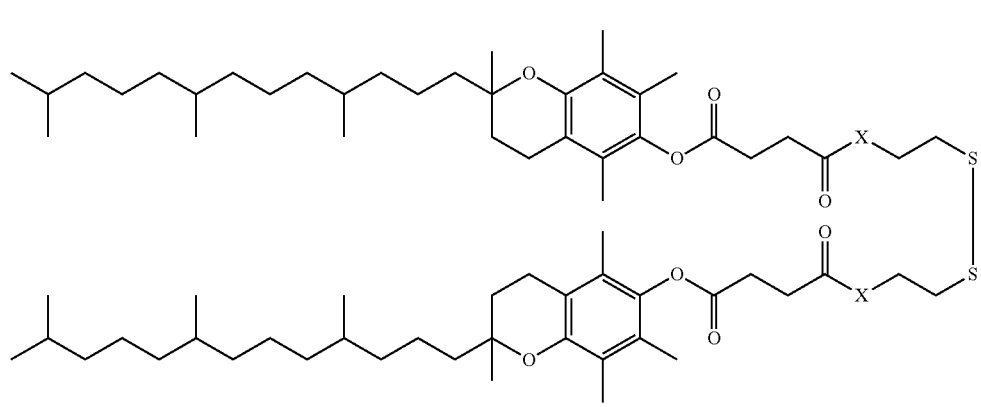

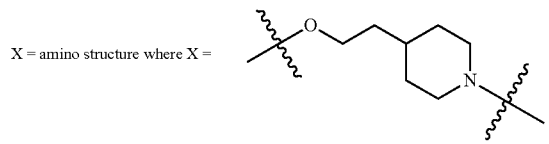

-continued

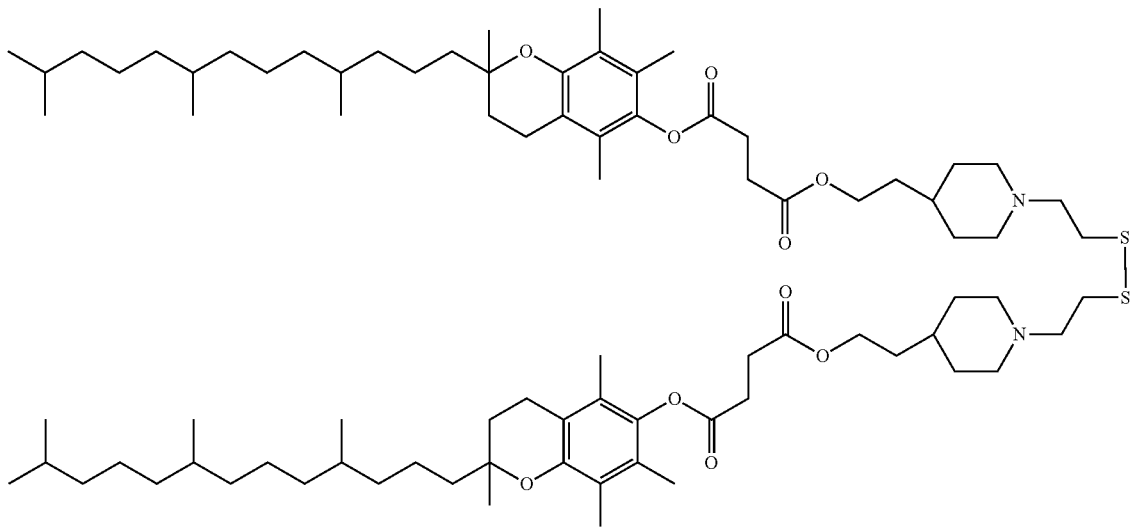

(xviii)(b)

(xix)

In some embodiments, a lipid compound used to form lipid nanoparticles for the delivery of compositions described herein, e.g., nucleic acid (e.g., RNA) described herein is made by one of the following reactions:

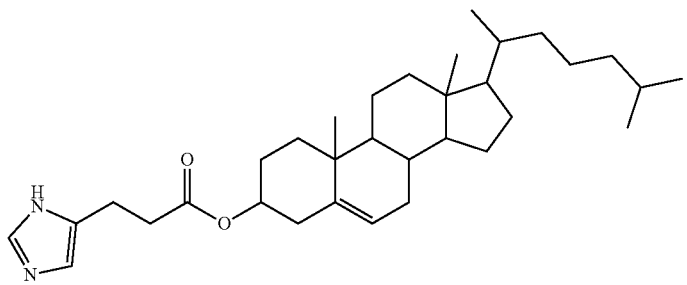

(xx)(a)

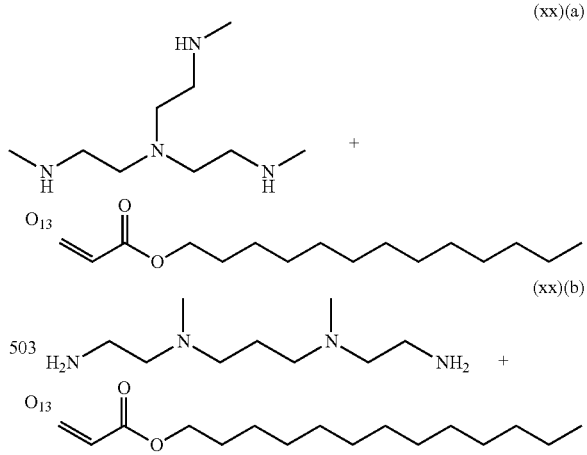

(xx)(b)

In some embodiments, a composition described herein (e.g., a nucleic acid or a protein) is provided in an LNP that comprises an ionizable lipid. In some embodiments, the ionizable lipid is heptadecan-9-yl 8-((2-hydroxyethyl)(6-oxo-6-(undecyloxy)hexyl)amino)octanoate (SM-102); e.g., as described in Example 1 of U.S. Pat. No. 9,867,888 (incorporated by reference herein in its entirety). In some embodiments, the ionizable lipid is 9Z,12Z)-3-((4,4-bis(octyloxy)butanoyl)oxy)-2-((((3-(diethylamino)propoxy)carbonyl)oxy)methyl)propyl octadeca-9,12-dienoate (LP01), e.g., as synthesized in Example 13 of WO2015/095340 (incorporated by reference herein in its entirety). In some embodiments, the ionizable lipid is Di((Z)-non-2-en-1-yl) 9-((4-dimethylamino)butanoyl)oxy)heptadecanedioate (L319), e.g. as synthesized in Example 7, 8, or 9 of US2012/0027803 (incorporated by reference herein in its entirety). In some embodiments, the ionizable lipid is 1,1'-((2-(4-(2-((2-(Bis(2-hydroxydodecyl)amino)ethyl)(2-hydroxydodecyl)amino)ethyl)piperazin-1-yl)ethyl)azanediyl)bis(dodecan-2-ol) (C12-200), e.g., as synthesized in Examples 14 and 16 of WO2010/053572 (incorporated by reference herein in its entirety). In some embodiments, the ionizable lipid is Imidazole cholesterol ester (ICE) lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, e.g., Structure (I) from WO2020/106946 (incorporated by reference herein in its entirety).

In some embodiments, an ionizable lipid may be a cationic lipid, an ionizable cationic lipid, e.g., a cationic lipid that can exist in a positively charged or neutral form depending on pH, or an amine-containing lipid that can be readily protonated. In some embodiments, the cationic lipid is a lipid capable of being positively charged, e.g., under physiological conditions. Exemplary cationic lipids include one or more amine group(s) which bear the positive charge. In some embodiments, the lipid particle comprises a cationic lipid in formulation with one or more of neutral lipids, ionizable amine-containing lipids, biodegradable alkyne lipids, steroids, phospholipids including polyunsaturated lipids, structural lipids (e.g., sterols), PEG, cholesterol and polymer conjugated lipids. In some embodiments, the cationic lipid may be an ionizable cationic lipid. An exemplary cationic lipid as disclosed herein may have an effective pKa over 6.0. In embodiments, a lipid nanoparticle may comprise a second cationic lipid having a different effective pKa (e.g., greater than the first effective pKa), than the first cationic lipid. A lipid nanoparticle may comprise between 40 and 60 mol percent of a cationic lipid, a neutral lipid, a steroid, a polymer conjugated lipid, and a therapeutic agent, e.g., a nucleic acid (e.g., RNA) described herein, encapsulated within or associated with the lipid nanoparticle. In some embodiments, the nucleic acid is co-formulated with the cationic lipid. The nucleic acid may be adsorbed to the surface of an LNP, e.g., an LNP comprising a cationic lipid. In some embodiments, the nucleic acid may be encapsulated in an LNP, e.g., an LNP comprising a cationic lipid. In some embodiments, the lipid nanoparticle may comprise a targeting moiety, e.g., coated with a targeting agent. In embodiments, the LNP formulation is biodegradable. In some embodiments, a lipid nanoparticle comprising one or more lipid described herein, e.g., Formula (i), (ii), (ii), (vii) and/or (ix) encapsulates at least 1%, at least 5%, at least 10%, at least 20%, at least 30%, at least 40%, at least 50%, at least 60%, at least 70%, at least 80%, at least 90%, at least 92%, at least 95%, at least 97%, at least 98% or 100% of an RNA molecule.

Exemplary ionizable lipids that can be used in lipid nanoparticle formulations include, without limitation, those listed in Table 1 of WO2019051289, incorporated herein by reference. Additional exemplary lipids include, without limitation, one or more of the following formulae: X of US2016/0311759; I of US20150376115 or in US2016/0376224; I, II or III of US20160151284; I, IA, II, or IIA of US20170210967; I-c of US20150140070; A of US2013/0178541; I of US2013/0303587 or US2013/0123338; I of US2015/0141678; II, III, IV, or V of US2015/0239926; I of US2017/0119904; I or II of WO2017/117528; A of US2012/0149894; A of US2015/0057373; A of WO2013/116126; A of US2013/0090372; A of US2013/0274523; A of US2013/0274504; A of US2013/0053572; A of WO2013/016058; A of WO2012/162210; I of US2008/042973; I, II, III, or IV of US2012/01287670; I or II of US2014/0200257; I, II, or III of US2015/0203446; I or III of US2015/0005363; I, IA, IB, IC, ID, II, IIA, IIB, IIC, IID, or III-XXIV of US2014/0308304; of US2013/0338210; I, II, III, or IV of WO2009/132131; A of US2012/01011478; I or XXXV of US2012/0027796; XIV or XVII of US2012/0058144; of US2013/0323269; I of US2011/0117125; I, II, or III of US2011/0256175; I, II, III, IV, V, VI, VII, VIII, IX, X, XI, XII of US2012/0202871; I, II, III, IV, V, VI, VII, VIII, X, XII, XIII, XIV, XV, or XVI of US2011/0076335; I or II of US2006/008378; I of US2013/0123338; I or X-A-Y-Z of US2015/0064242; XVI, XVII, or XVIII of US2013/0022649; I, II, or III of US2013/0116307; I, II, or III of US2013/0116307; I or II of US2010/0062967; I-X of US2013/0189351; I of US2014/0039032; V of US2018/0028664; I of US2016/0317458; I of US2013/0195920; 5, 6, or 10 of U.S. Pat. No. 10,221,127; III-3 of WO2018/081480; I-5 or I-8 of WO2020/081938; 18 or 25 of U.S. Pat. No. 9,867,888; A of US2019/0136231; II of WO2020/219876; 1 of US2012/0027803; OF-02 of US2019/0240349; 23 of U.S. Pat. No. 10,086,013; cKK-E12/A6 of Miao et al (2020); C12-200 of WO2010/053572; 7C1 of Dahlman et al (2017); 304-013 or 503-013 of Whitehead et al; TS-P4C2 of U.S. Pat. No. 9,708,628; I of WO2020/106946; I of WO2020/106946.

In some embodiments, the ionizable lipid is MC3 (6Z,9Z,28Z,31Z)-heptatriaconta-6,9,28,3 1-tetraen-19-yl-4-(dimethylamino) butanoate (DLin-MC3-DMA or MC3), e.g., as described in Example 9 of WO2019051289A9 (incorporated by reference herein in its entirety). In some embodiments, the ionizable lipid is the lipid ATX-002, e.g., as described in Example 10 of WO2019051289A9 (incorporated by reference herein in its entirety). In some embodiments, the ionizable lipid is (13Z,16Z)-A,A-dimethyl-3-nonyldocosa-13, 16-dien-1-amine (Compound 32), e.g., as described in Example 11 of WO2019051289A9 (incorporated by reference herein in its entirety). In some embodiments, the ionizable lipid is Compound 6 or Compound 22, e.g., as described in Example 12 of WO2019051289A9 (incorporated by reference herein in its entirety).

Exemplary non-cationic lipids include, but are not limited to, distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethylphosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleoylphosphatidylglycerol (POPG), dielaidoyl-phosphatidylethanolamine (DEPE), lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, or mixtures thereof. It is understood that other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, paimitoyl, stearoyl, or oleoyl. Additional exemplary lipids, in certain embodiments, include, without limitation, those described in Kim et al. (2020) dx.doi.org/10.1021/acs.nanolett.Oc01386, incorporated herein by reference. Such lipids include, in some embodiments, plant lipids found to improve liver transfection with mRNA (e.g., DGTS).

Other examples of non-cationic lipids suitable for use in the lipid nanoparticles include, without limitation, nonphosphorous lipids such as, e.g., stearylamine, dodeeylamine, hexadecylamine, acetyl palmitate, glycerol ricinoleate, hexadecyl stereate, isopropyl myristate, amphoteric acrylic polymers, triethanolamine-lauryl sulfate, alkyl-aryl sulfate polyethyloxylated fatty acid amides, dioctadecyl dimethyl ammonium bromide, ceramide, sphingomyelin, and the like. Other non-cationic lipids are described in WO2017/099823 or US patent publication US2018/0028664, the contents of which is incorporated herein by reference in their entirety.

In some embodiments, the non-cationic lipid is oleic acid or a compound of Formula I, II, or IV of US2018/0028664, incorporated herein by reference in its entirety. The non-cationic lipid can comprise, for example, 0-30% (mol) of the total lipid present in the lipid nanoparticle. In some embodiments, the non-cationic lipid content is 5-20% (mol) or 10-15% (mol) of the total lipid present in the lipid nanoparticle. In embodiments, the molar ratio of ionizable lipid to the neutral lipid ranges from about 2:1 to about 8:1 (e.g., about 2:1, 3:1, 4:1, 5:1, 6:1, 7:1, or 8:1).

In some embodiments, the lipid nanoparticles do not comprise any phospholipids.

In some aspects, the lipid nanoparticle can further comprise a component, such as a sterol, to provide membrane integrity. One exemplary sterol that can be used in the lipid nanoparticle is cholesterol and derivatives thereof. Non-limiting examples of cholesterol derivatives include polar analogues such as 5a-choiestanol, 53-coprostanol, choiesteryl-(2'-hydroxy)-ethyl ether, choiesteryl-(4'-hydroxy)-butyl ether, and 6-ketocholestanol; non-polar analogues such as 5a-cholestane, cholestenone, 5a-cholestanone, 5p-cholestanone, and cholesteryl decanoate; and mixtures thereof. In some embodiments, the cholesterol derivative is a polar analogue, e.g., choiesteryl-(4'-hydroxy)-butyl ether. Exemplary cholesterol derivatives are described in PCT publication WO2009/127060 and US patent publication US2010/0130588, each of which is incorporated herein by reference in its entirety.

In some embodiments, the component providing membrane integrity, such as a sterol, can comprise 0-50% (mol) (e.g., 0-10%, 10-20%, 20-30%, 30-40%, or 40-50%) of the total lipid present in the lipid nanoparticle. In some embodiments, such a component is 20-50% (mol) 30-40% (mol) of the total lipid content of the lipid nanoparticle.

In some embodiments, the lipid nanoparticle can comprise a polyethylene glycol (PEG) or a conjugated lipid molecule. Generally, these are used to inhibit aggregation of lipid nanoparticles and/or provide steric stabilization. Exemplary conjugated lipids include, but are not limited to, PEG-lipid conjugates, polyoxazoline (POZ)-lipid conjugates, polyamide-lipid conjugates (such as *ATTA*-lipid conjugates), cationic-polymer lipid (CPL) conjugates, and mixtures thereof. In some embodiments, the conjugated lipid molecule is a PEG-lipid conjugate, for example, a (methoxy polyethylene glycol)-conjugated lipid.

Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy)propyl-1-0-(w-methoxy(polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, US2017/0119904, and US/099823, the contents of all of which are incorporated herein by reference in their entirety. In some embodiments, a PEG-lipid is a compound of Formula III, III-a-I, III-a-2, III-b-I, III-b-2, or V of US2018/0028664, the content of which is incorporated herein by reference in its entirety. In some embodiments, a PEG-lipid is of Formula II of US20150376115 or US2016/0376224, the content of both of which is incorporated herein by reference in its entirety. In some embodiments, the PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy(polyethylene glycol)-2000]. In some embodiments, the PEG-lipid comprises PEG-DMG, 1,2-dimyristoyl-sn-glycero-3-phosphoethanolamine-N-[methoxy(polyethylene glycol)-2000]. In some embodiments, the PEG-lipid comprises a structure selected from:

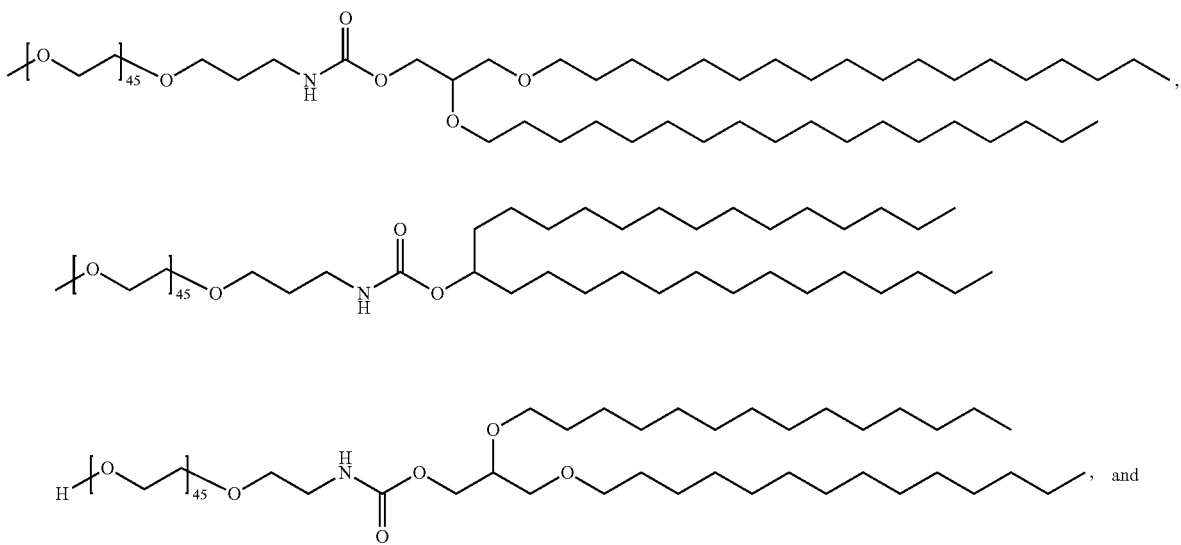

-continued

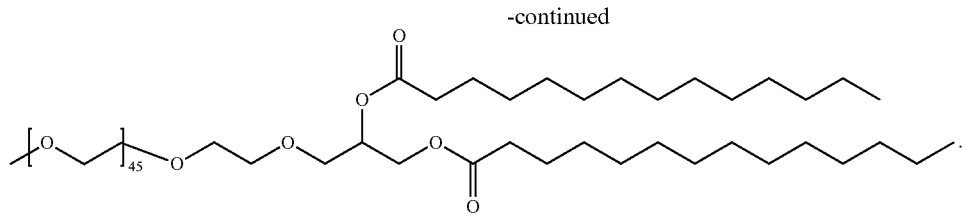

In some embodiments, lipids conjugated with a molecule other than a PEG can also be used in place of PEG-lipid. For example, polyoxazoline (POZ)-lipid conjugates, polyamide-lipid conjugates (such as *ATTA*-lipid conjugates), and cationic-polymer lipid (GPL) conjugates can be used in place of or in addition to the PEG-lipid.

Exemplary conjugated lipids, i.e., PEG-lipids, (POZ)-lipid conjugates, *ATTA*-lipid conjugates and cationic polymer-lipids are described in the PCT and US patent applications listed in Table 2 of WO2019051289A9, the contents of all of which are incorporated herein by reference in their entirety.

In some embodiments, the PEG or the conjugated lipid can comprise 0-20% (mol) of the total lipid present in the lipid nanoparticle. In some embodiments, PEG or the conjugated lipid content is 0.5-10% or 2-5% (mol) of the total lipid present in the lipid nanoparticle. Molar ratios of the ionizable lipid, non-cationic-lipid, sterol, and PEG/conjugated lipid can be varied as needed. For example, the lipid particle can comprise 30-70% ionizable lipid by mole or by total weight of the composition, 0-60% cholesterol by mole or by total weight of the composition, 0-30% non-cationic-lipid by mole or by total weight of the composition and 1-10% conjugated lipid by mole or by total weight of the composition. Preferably, the composition comprises 30-40% ionizable lipid by mole or by total weight of the composition, 40-50% cholesterol by mole or by total weight of the composition, and 10-20% non-cationic-lipid by mole or by total weight of the composition. In some other embodiments, the composition is 50-75% ionizable lipid by mole or by total weight of the composition, 20-40% cholesterol by mole or by total weight of the composition, and 5 to 10% non-cationic-lipid, by mole or by total weight of the composition and 1-10% conjugated lipid by mole or by total weight of the composition. The composition may contain 60-70% ionizable lipid by mole or by total weight of the composition, 25-35% cholesterol by mole or by total weight of the composition, and 5-10% non-cationic-lipid by mole or by total weight of the composition. The composition may also contain up to 90% ionizable lipid by mole or by total weight of the composition and 2 to 15% non-cationic lipid by mole or by total weight of the composition. The formulation may also be a lipid nanoparticle formulation, for example comprising 8-30% ionizable lipid by mole or by total weight of the composition, 5-30% non-cationic lipid by mole or by total weight of the composition, and 0-20% cholesterol by mole or by total weight of the composition; 4-25% ionizable lipid by mole or by total weight of the composition, 4-25% non-cationic lipid by mole or by total weight of the composition, 2 to 25% cholesterol by mole or by total weight of the composition, 10 to 35% conjugate lipid by mole or by total weight of the composition, and 5% cholesterol by mole or by total weight of the composition; or 2-30% ionizable lipid by mole or by total weight of the composition, 2-30% non-cationic lipid by mole or by total weight of the composition, 1 to 15% cholesterol by mole or by total weight of the composition, 2 to 35% conjugate lipid by mole or by total weight of the composition, and 1-20% cholesterol by mole or by total weight of the composition; or even up to 90% ionizable lipid by mole or by total weight of the composition and 2-10% non-cationic lipids by mole or by total weight of the composition, or even 100% cationic lipid by mole or by total weight of the composition. In some embodiments, the lipid particle formulation comprises ionizable lipid, phospholipid, cholesterol and a PEG-ylated lipid in a molar ratio of 50:10:38.5:1.5. In some other embodiments, the lipid particle formulation comprises ionizable lipid, cholesterol and a PEG-ylated lipid in a molar ratio of 60:38.5:1.5.

In some embodiments, the lipid particle comprises ionizable lipid, non-cationic lipid (e.g. phospholipid), a sterol (e.g., cholesterol) and a PEG-ylated lipid, where the molar ratio of lipids ranges from 20 to 70 mole percent for the ionizable lipid, with a target of 40-60, the mole percent of non-cationic lipid ranges from 0 to 30, with a target of 0 to 15, the mole percent of sterol ranges from 20 to 70, with a target of 30 to 50, and the mole percent of PEG-ylated lipid ranges from 1 to 6, with a target of 2 to 5.

In some embodiments, the lipid particle comprises ionizable lipid/non-cationic-lipid/sterol/conjugated lipid at a molar ratio of 50:10:38.5:1.5.

In an aspect, the disclosure provides a lipid nanoparticle formulation comprising phospholipids, lecithin, phosphatidylcholine and phosphatidylethanolamine.

In some embodiments, one or more additional compounds can also be included. Those compounds can be administered separately, or the additional compounds can be included in the lipid nanoparticles of the invention. In other words, the lipid nanoparticles can contain other compounds in addition to the nucleic acid or at least a second nucleic acid, different than the first. Without limitations, other additional compounds can be selected from the group consisting of small or large organic or inorganic molecules, monosaccharides, disaccharides, trisaccharides, oligosaccharides, polysaccharides, peptides, proteins, peptide analogs and derivatives thereof, peptidomimetics, nucleic acids, nucleic acid analogs and derivatives, an extract made from biological materials, or any combinations thereof.

Figure 6:
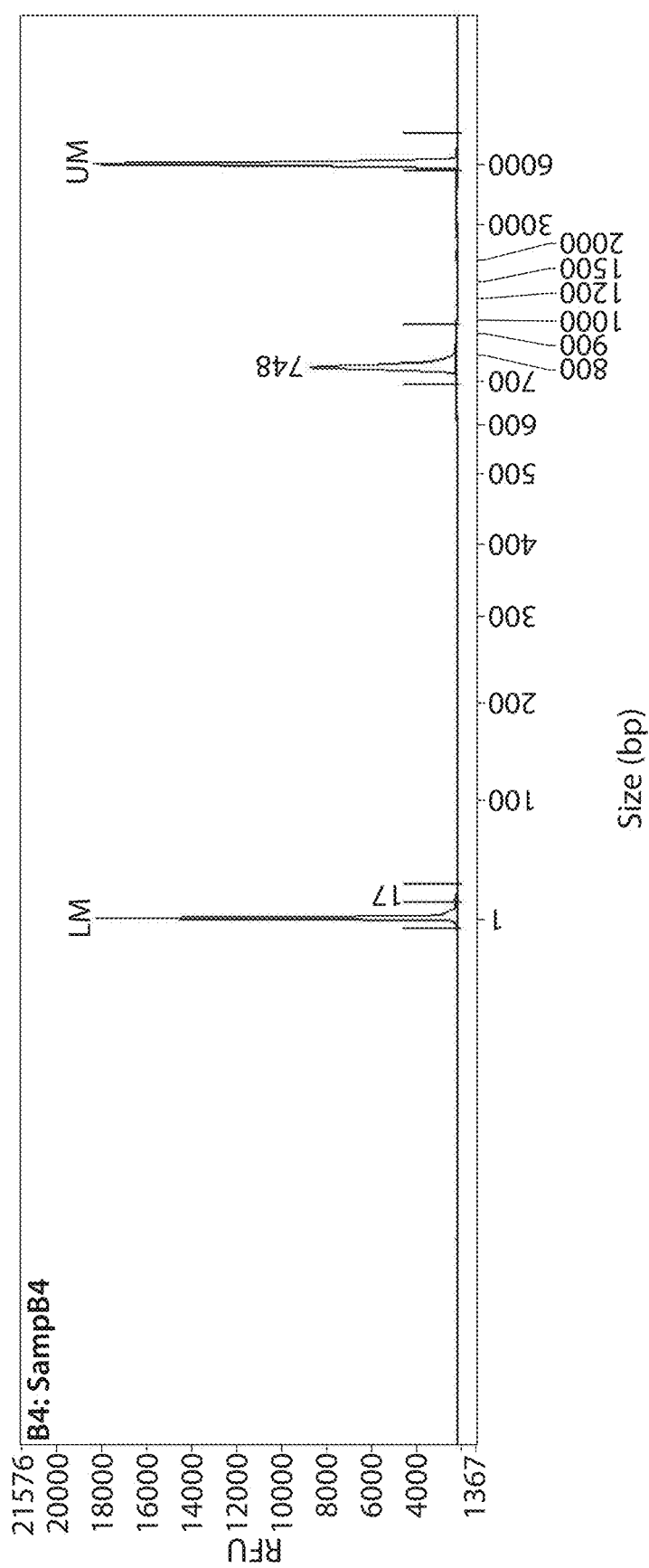
Figure 7:
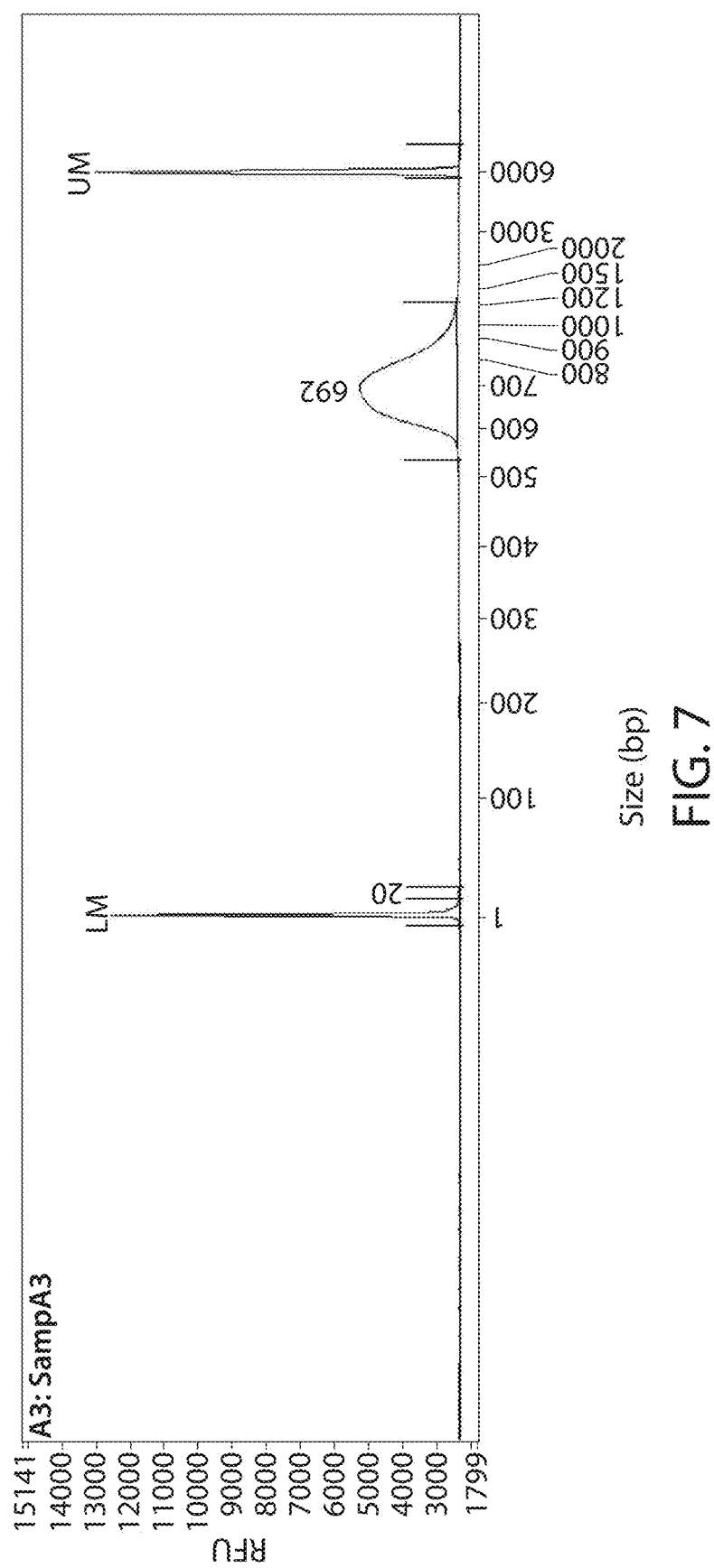
Figure 8:
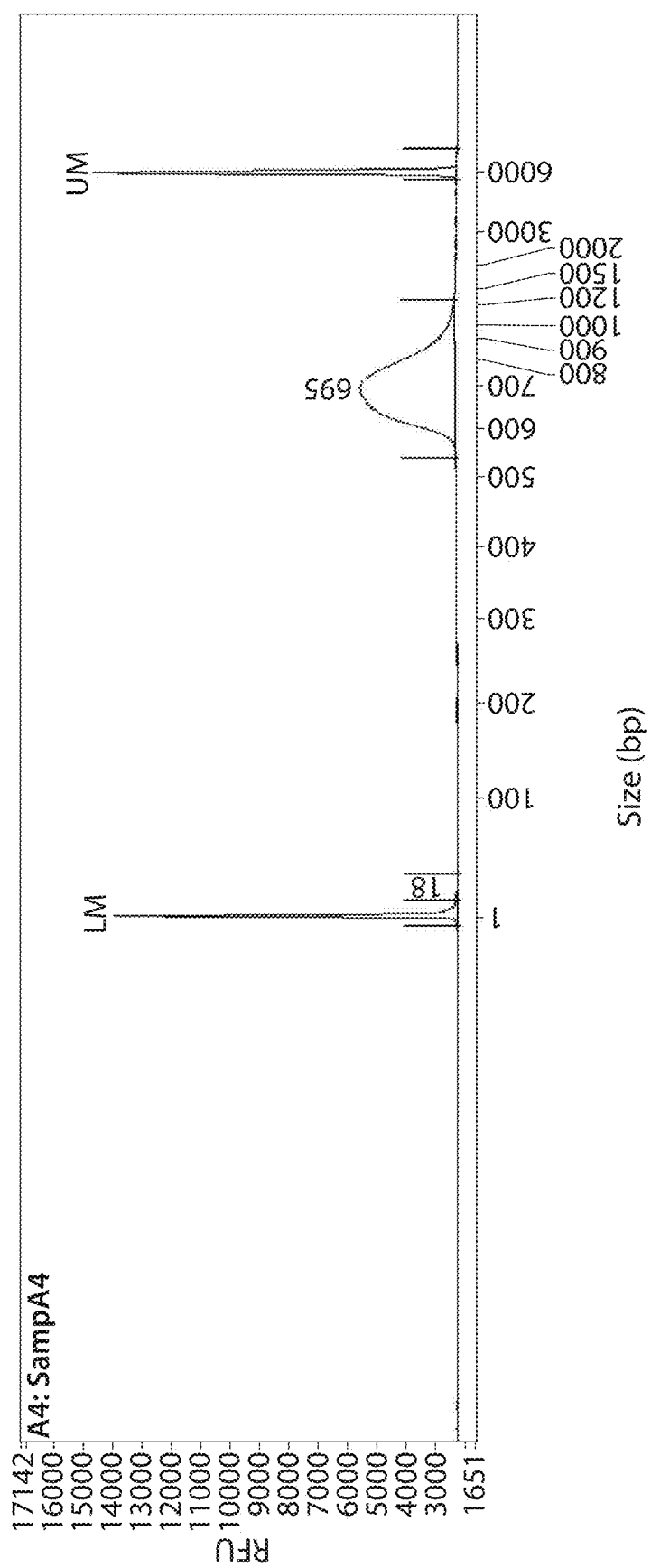

In some embodiments, LNPs are directed to specific tissues by the addition of targeting domains. For example, biological ligands may be displayed on the surface of LNPs to enhance interaction with cells displaying cognate receptors, thus driving association with and cargo delivery to tissues wherein cells express the receptor. In some embodiments, the biological ligand may be a ligand that drives delivery to the liver, e.g., LNPs that display GalNAc result in delivery of nucleic acid cargo to hepatocytes that display asialoglycoprotein receptor (ASGPR). The work of Akinc et al. *Mol Ther* 18(7):1357-1364 (2010) teaches the conjugation of a trivalent GalNAc ligand to a PEG-lipid (GalNAc-PEG-DSG) to yield LNPs dependent on ASGPR for observable LNP cargo effect (see, e.g., FIG. 6 of Akinc et al. 2010, supra). Other ligand-displaying LNP formulations, e.g., incorporating folate, transferrin, or antibodies, are discussed in WO2017223135, which is incorporated herein by reference in its entirety, in addition to the references used therein, namely Kolhatkar et al., *Curr Drug Discov Technol.* 2011 8:197-206; Musacchio and Torchilin, *Front Biosci.* 2011 16:1388-1412; Yu et al., *Mol Membr Biol.* 2010 27:286-298; Patil et al., *Crit Rev Ther Drug Carrier Syst.* 2008 25:1-61; Benoit et al., *Biomacromolecules.* 2011 12:2708-2714; Zhao et al., *Expert Opin Drug Deliv.* 2008 5:309-319; Akinc et al., *Mol Ther.* 2010 18:1357-1364; Srinivasan et al., *Methods Mol Biol.* 2012 820:105-116; Ben-Arie et al., *Methods Mol Biol.* 2012 757:497-507; Peer 2010 *J Control Release.* 20:63-68; Peer et al., *Proc Natl Acad Sci USA.* 2007 104:4095-4100; Kim et al., *Methods Mol Biol.* 2011 721:339-353; Subramanya et al., *Mol Ther.* 2010 18:2028-2037; Song et al., *Nat Biotechnol.* 2005 23:709-717; Peer et al., *Science.* 2008 319:627-630; and Peer and Lieberman, *Gene Ther.* 2011 18:1127-1133.

In some embodiments, LNPs are selected for tissue-specific activity by the addition of a Selective ORgan Targeting (SORT) molecule to a formulation comprising traditional components, such as ionizable cationic lipids, amphipathic phospholipids, cholesterol and poly(ethylene glycol) (PEG) lipids. The teachings of Cheng et al. *Nat Nanotechnol* 15(4):313-320 (2020) demonstrate that the addition of a supplemental "SORT" component precisely alters the in vivo RNA delivery profile and mediates tissue-specific (e.g., lungs, liver, spleen) gene delivery and editing as a function of the percentage and biophysical property of the SORT molecule.

In some embodiments, the LNPs comprise biodegradable, ionizable lipids. In some embodiments, the LNPs comprise (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate) or another ionizable lipid. See, e.g, lipids of WO2019/067992, WO/2017/173054, WO2015/095340, and WO2014/136086, as well as references provided therein. In some embodiments, the term cationic and ionizable in the context of LNP lipids is interchangeable, e.g., wherein ionizable lipids are cationic depending on the pH.

In some embodiments, the average LNP diameter of the LNP formulation may be between 10s of nm and 100s of nm, e.g., measured by dynamic light scattering (DLS). In some embodiments, the average LNP diameter of the LNP formulation may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the average LNP diameter of the LNP formulation may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In some embodiments, the average LNP diameter of the LNP formulation may be from about 70 nm to about 100 nm. In a particular embodiment, the average LNP diameter of the LNP formulation may be about 80 nm. In some embodiments, the average LNP diameter of the LNP formulation may be about 100 nm. In some embodiments, the average LNP diameter of the LNP formulation ranges from about 1 mm to about 500 mm, from about 5 mm to about 200 mm, from about 10 mm to about 100 mm, from about 20 mm to about 80 mm, from about 25 mm to about 60 mm, from about 30 mm to about 55 mm, from about 35 mm to about 50 mm, or from about 38 mm to about 42 mm.

A LNP may, in some instances, be relatively homogenous. A polydispersity index may be used to indicate the homogeneity of a LNP, e.g., the particle size distribution of the lipid nanoparticles. A small (e.g., less than 0.3) polydispersity index generally indicates a narrow particle size distribution. A LNP may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a LNP may be from about 0.10 to about 0.20.

The zeta potential of a LNP may be used to indicate the electrokinetic potential of the composition. In some embodiments, the zeta potential may describe the surface charge of an LNP. Lipid nanoparticles with relatively low charges, positive or negative, are generally desirable, as more highly charged species may interact undesirably with cells, tissues, and other elements in the body. In some embodiments, the zeta potential of a LNP may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a protein and/or nucleic acid, describes the amount of protein and/or nucleic acid that is encapsulated or otherwise associated with a LNP after preparation, relative to the initial amount provided. The encapsulation efficiency is desirably high (e.g., close to 100%). The encapsulation efficiency may be measured, for example, by comparing the amount of protein or nucleic acid in a solution containing the lipid nanoparticle before and after breaking up the lipid nanoparticle with one or more organic solvents or detergents. An anion exchange resin may be used to measure the amount of free protein or nucleic acid (e.g., RNA) in a solution. Fluorescence may be used to measure the amount of free protein and/or nucleic acid (e.g., RNA) in a solution. For the lipid nanoparticles described herein, the encapsulation efficiency of a protein and/or nucleic acid may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In some embodiments, the encapsulation efficiency may be at least 90%. In some embodiments, the encapsulation efficiency may be at least 95%.

A LNP may optionally comprise one or more coatings. In some embodiments, a LNP may be formulated in a capsule, film, or table having a coating. A capsule, film, or tablet including a composition described herein may have any useful size, tensile strength, hardness or density.

Additional exemplary lipids, formulations, methods, and characterization of LNPs are taught by WO2020061457, which is incorporated herein by reference in its entirety. See also: Hou et al. Lipid nanoparticles for mRNA delivery. *Nat Rev Mater* (2021). https://doi.org/10.1038/s41578-021-00358-0.

In some embodiments, in vitro or ex vivo cell lipofections are performed using Lipofectamine MessengerMax (Thermo Fisher) or TransIT-mRNA Transfection Reagent (Mirus Bio). In certain embodiments, LNPs are formulated using the GenVoy_ILM ionizable lipid mix (Precision NanoSystems). In certain embodiments, LNPs are formulated using 2,2-dilinoleyl-4-dimethylaminoethyl-[1,3]-dioxolane (DLin-KC2-DMA) or dilinoleylmethyl-4-dimethylaminobutyrate (DLin-MC3-DMA or MC3), the formulation and in vivo use of which are taught in Jayaraman et al. *Angew Chem Int Ed Engl* 51(34):8529-8533 (2012), incorporated herein by reference in its entirety.

LNP formulations optimized for the delivery of CRISPR-Cas systems, e.g., Cas9-gRNA RNP, gRNA, Cas9 mRNA, are described in WO2019067992 and WO2019067910, both incorporated by reference.

Additional specific LNP formulations useful for delivery of nucleic acids are described in U.S. Pat. Nos. 8,158,601 and 8,168,775, both incorporated by reference, which include formulations used in patisiran, sold under the name ONPATTRO.

Exemplary dosing of a DNA described herein with an LNP may include about 0.1, 0.25, 0.3, 0.5, 1, 2, 3, 4, 5, 6, 8, 10, or 100 mg/kg (DNA).

The following embodiments are contemplated:
A. A lipid nanoparticle (LNP) comprising a ssDNA construct, sequence or composition described herein.
B. The LNP of embodiment A, comprising a cationic lipid.
C. The LNP of embodiment B, wherein the cationic lipid has a structure according to:

lipid, e.g., a pegylated lipid, e.g., PEG-DAG, PEG-PE, PEG-S-DAG, PEG-cer or a PEG dialkyoxypropylcarbamate.

In embodiments, an LNP preparation comprising a ssDNA or construct described herein can be targeted to the desired cell type by surface decoration with targeting effectors. Such targeting effectors include, e.g., cell specific receptor ligands that bind a target cell; antibodies or other binders against a target cell; centryins; cell penetrating peptides; peptides that enable endosomal escape (e.g., GALA, KALA). See, e.g., Tables 1 and 2 of Tai & Gao. 2017. *Adv Drug Deliv Rev.* 110-111:157-168, for a review.

In embodiments, an LNP preparation comprising a ssDNA or construct described herein can be co-administered with an adjuvant, e.g., co-delivered in the same preparation with an adjuvant.

Route of Administration

A ssDNA or construct described herein is introduced into a cell, tissue or subject by any suitable route.

Administration to a target cell or tissue (e.g., ex vivo) may be by methods known in the art such as transfection, e.g., transient or stable transfection using reagents (e.g., liposomal, calcium phosphate) or physical means (e.g., electroporation, gene gun, microinjection, microfluidic fluid shear, cell squeezing). Other methods are described, e.g., in Rad et al. 2021. *Adv. Mater.* 33:2005363, which is incorporated herein by reference.

Administration to a subject, e.g., a mammal, e.g., a human subject, may be by parenteral (e.g., intravenous, intramuscular, intraperitoneal, subcutaneous, intracranial) route; by topical administration, transdermal administration or transcutaneous administration. Other suitable routes include oral, rectal, transmucosal, intranasal, inhalation (e.g., via an aerosol), buccal (e.g., sublingual), vaginal, intrathecal, intraocular, transdermal, intraendothelial, in utero (or in ovo),

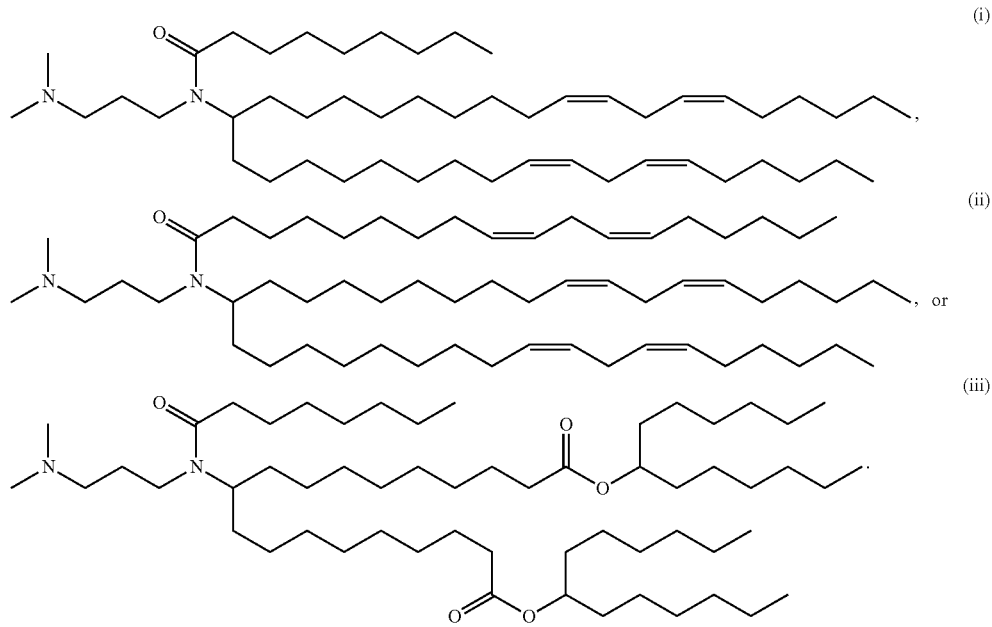

D. The LNP of any of embodiments A-C, further comprising one or more neutral lipid, e.g., DSPC, DPPC, DMPC, DOPC, POPC, DOPE, SM, a steroid, e.g., cholesterol, and/or one or more polymer conjugated intrapleural, intracerebral, intraarticular, topical, intralymphatic. Also included is direct tissue or organ injection (e.g., to liver, eye, skeletal muscle, cardiac muscle, diaphragm, muscle or brain).

Integration into a Genome

In some embodiments, a ssDNA described herein, when introduced into a cell, integrates into the genome of the cell. In other embodiments, a ssDNA described herein, when introduced into a cell, does not integrate into the genome of the cell. In some embodiments, a ssDNA described herein integrates into the genome of a subject at a frequency of less than about 0.0001%, 0.001%, 0.005%, 0.01%, 0.05%, 0.1%, 0.5%, 1%, 1.5%, or 2% of the copies of the ssDNA that are administered to the subject.

In some embodiments, a ssDNA described herein does not comprise a homology arm. In some embodiments, a ssDNA described herein does not comprise two homology arms. In some embodiments, a ssDNA described herein does not comprise more than 70%, 80%, or 90%, identity to any 15 nucleotide portion of the reference human genome hg38. In some embodiments, a ssDNA described herein does not comprise more than 70% identity to any 15 nucleotide portion of the reference human genome hg38. In some embodiments, a ssDNA described herein does not comprise more than 70%, 80%, 90%, 95% identity to any 25 nucleotide portion of the reference human genome hg38. In some embodiments, a ssDNA described herein does not comprise more than 70%, 80%, 90%, 95%, or 98% identity to any 50 nucleotide portion of the reference human genome hg38. In some embodiments, a ssDNA described herein does not comprise more than 70%, 80%, 90%, 95%, 98%, or 99% identity to any 100 nucleotide portion of the reference human genome hg38.

In some embodiments, the ssDNA described herein is not a template for homology-directed repair (HDR). In some embodiments, the ssDNA described herein does not participate in microhomology-mediated end joining (MMEJ). In some embodiments, the ssDNA described herein does not participate in DNA repair.

In some embodiments, the formulation does not comprise a nuclease (e.g., a CRISPR nuclease, e.g., a CRISPR nuclease that produces single stranded or double stranded breaks). In some embodiments, the formulation does not comprise a protein that promotes integration of the ssDNA into the genome, e.g., wherein the protein comprises a recombinase or integrase.

Applications

The ssDNA and constricts described herein can be used in therapeutic or health applications for a subject, e.g., a human. Although the descriptions of pharmaceutical compositions provided herein are principally directed to pharmaceutical compositions which are suitable for administration to humans, it will be understood by the skilled artisan that such compositions are generally suitable for administration to any other animal. The subject can be any animal, e.g., a mammal, e.g., a human or non-human mammal. In embodiments, the subject is a vertebrate animal (e.g., mammal, bird, fish, reptile, or amphibian). In embodiments, the subject is a human. In embodiments, the method subject is a non-human mammal. In embodiments, the subject is a non-human mammal is such as a non-human primate (e.g., monkeys, apes), ungulate (e.g., cattle, buffalo, sheep, goat, pig, camel, llama, alpaca, deer, horses, donkeys), carnivore (e.g., dog, cat), rodent (e.g., rat, mouse), or lagomorph (e.g., rabbit). In embodiments, the subject is a bird, such as a member of the avian taxa Galliformes (e.g., chickens, turkeys, pheasants, quail), Anseriformes (e.g., ducks, geese), Paleaognathae (e.g., ostriches, emus), Columbiformes (e.g., pigeons, doves), or Psittaciformes (e.g., parrots). In embodiments, the subject is an invertebrate such as an arthropod (e.g., insects, arachnids, crustaceans), a nematode, an annelid, a helminth, or a mollusk.

In some embodiments, a ssDNA or construct described herein imparts a biological effect of the effector, e.g., expression of a therapeutic polypeptide, on a host cell, tissue or subject over a time period of at least 2, 3, 4, 5, 6 days or a week; at least 8, 9, 10, 12, 14 days or two weeks; at least 16, 18, 20 days or 3 weeks; at least 22, 24, 25, 27, 28 days or a month; at least 2 months, 3 months, 4 months, 5 months, 6 months or more; between one week and 6 months, between 1 month to 6 months, between 3 months to 6 months.

In embodiments, an ssDNA or construct described herein can be used to deliver an effector, e.g., an effector described herein, to a cell, tissue or subject.

In embodiments, an ssDNA or construct described herein can be used to modulate (e.g., increase or decrease) a biological parameter in a cell, tissue or subject. The biological parameter may be an increase or decrease in gene expression of a subject gene in a target cell, tissue or subject.

In embodiments, an ssDNA or construct described herein can be used to treat a cell, tissue or subject in need thereof by administering a ssDNA or construct described herein to such cell, tissue or subject.

EXAMPLES

Example 1: Design and Assembly of a Plasmid Template for a Covalently Closed ssDNA This example describes how to create a plasmid template for a ssDNA construct. In this example, a construct template is designed with the following specific sequence components.

```
Promoter Ef1a:
                                                           (SEQ ID NO: 37)
5'ggctccggtgcccgtcagtgggcagagcgcacategcccacagtccccgagaagttgggggag gggtcggcaattgaaccggtgcctagagaaggtggcgcggggtaaactgggaaagtgatgtcgtgt actggctccgccttttcccgagggtggggaaccgtatataagtgcagtagtcgccgtgaacgttc tttttcgcaacgggtttgccgccagaacacaggtaagtgccgtgtgtggttcccgcgggcctggcc tctttacgggttatggcccttgcgtgccttgaattacttccacctggctgcagtacgtgattcttg atcccgagcttcgggttggaagtgggggagagttcgaggccttgcgcttaaggagccccttcgcc tcgtgcttgagttgaggcctggcctgggcgctggggccgccgcgtgcgaatctggtggcaccttcg cgcctgtctcgctgctttcgataagtctctagccatttaaaattttttgatgacctgctgcgacgct
```

-continued
tttttctggcaagatagtcttgtaaatgcgggcaagatctgcacactggtatttcggtttttgg ggccgcgggcggcgacggggcccgtgcgtcccagcgcacatgttcggcgaggcggggcctgcgagc gcggccaccgagaatcggacgggggtagtctcaagctggccggcctgctctggtgcctggcctcgc gccgccgtgtatcgccccgccctgggcggcaaggctggcccggtcggcaccagttgcgtgagcgga aagatggccgcttcccggccctgctgcagggagctcaaaatggaggacgcggcgctcgggagagcg gggggtgagtcacccacacaaaggaaaagggcctttccgtcctcagccgtcgcttcatgtgactcc acggagtaccgggcgccgtccaggcacctcgattagttctcgagcttttggagtacgtcgtcttta ggttgggggagggtttatgcgatggagtttccccacactgagtgggtggagactgaagttagg ccagcttggcacttgatgtaattctccttggaatttgccctttttgagtttggatcttggttcatt ctcaagcctcagacagtggttcaaagttttttctccatttcaggtgtcgtga-3'

Effector sequence encoding a model/marker protein (mCherry):
(SEQ ID NO: 38)
5'atggtgagcaagggcgaggaggataacatggccatcatcaaggagttcatgcgcttcaaggtgc acatggagggctccgtgaacggccacgagttcgagatcgagggcgagggcgagggccgcccctacg agggcacccagaccgccaagctgaaggtgaccaagggtggccccctgcccttcgcctgggacatcc tgtcccctcagttcatgtacggctccaaggcctacgtgaagcaccccgccgacatcccccgactact tgaagctgtccttccccgagggcttcaagtgggagcgcgtgatgaacttcgaggacggcggcgtgg tgaccgtgacccaggactctccctgcaggacggcgagttcatctacaaggtgaagctgcgcggca ccaacttcccctccgacggccccgtaatgcagaagaagaccatgggctgggaggcctcctccgagc ggatgtaccccgaggacggcgccctgaagggcgagatcaagcagaggetgaagctgaaggacggcg gccactacgacgctgaggtcaagaccacctacaaggccaagaagcccgtgcagctgcccggcgcct acaacgtcaacatcaagttggacatcacctcccacaacgaggactacaccatcgtggaacagtacg aacgcgccgagggccgccactccaccggcggcatggacgagctgtacaagtaa-3'

Optional:
(SEQ ID NO: 1)
NTS: SV40 enhancer: 5'-cccaagaagaagaggaaagtc-3'

Maintenance sequence: human interferon-ß MAR
(SEQ ID NO: 39)
5'tataattcactggaattttttgtgtgtatggtatgacatatgggttccctttatttttaca tataaatatatttccctgtttttctaaaaaagaaaaagatcatcattttcccattgtaaaatgcca tattttttcataggtcacttacata3'

Second strand motif: AAV2 wildtype ITR
(SEQ ID NO: 26)
5'aggaacccctagtgatggagttggccactccctctctgcgcgctcgctcgctcactgaggccgg gcgaccaaaggtcgcccgacgcccgggctttgcccgggcggcctcagtgagcgagcgagcgcgcag ctgcctgcagg-3'

A plasmid template is designed with these elements using standard DNA design manipulation software. Assembly is performed via Golden Gate Assembly following published protocols and commercially available kits (Marillonnet & GriGtzner. 2020. Synthetic DNA assembly using golden gate cloning and the hierarchical modular cloning pipeline. *Current Protocols in Molecular Biology*.130:el 15; Golden Gate Assembly Protocol for Using NEB Golden Gate Assembly Mix (E1600) (New England Biolabs)). Golden Gate assembly of the designed construct is performed using a series of primers 120 bp long with the first 30 bp matching the relevant adjacent fragment, the next 60 bp encoding for the new sequence, and the final 30 bp annealing to the target sequence. Fragments are assembled into the final construct design (NEB Golden Gate Assembly Kit) and sequences are confirmed by Sanger Sequencing (Sigma Aldrich) according to manufacturer protocols.

Example 2: Conversion of Plasmid DNA to Circular ssDNA

This example describes generation of a ssDNA from the template prepared as described in Example 1, following the methods in Minev et al., 2019, *Rapid in vitro production of single-stranded DNA, Nucleic Acids Research*, Volume 47, Issue 22:11956-11962, which is incorporated herein by reference. Briefly, PCR with a forward primer bearing a methanol-responsive polymer generates a tagged amplicon that enables selective precipitation of the modified strand under denaturing conditions. Unmodified and modified bases can be incorporated into the constructs using these methods.

The final sample is analyzed with NanoDrop to determine purity and concentration. The sequence of the construct is validated with next generation sequencing according to manufacturer protocols (Illumina).

Example 3: Generation of Circularized ssDNA

The linear ssDNA construct made as described in Example 2 is circularized, e.g., covalently closed, using a DNA ligase, such as Ampligase® Thermostable DNA Ligase (Lucigen, MA023E-Ampligase® Thermostable DNA Ligase) or CircLigase™ II ssDNA Ligase (Lucigen, MA298E-CircLigase-II-ssDNA-Ligase). Ampligase ligates DNA ends that are annealed adjacent to each other on a complementary DNA sequence, while CircLigase II ssDNA Ligase ligates ends of ssDNA in the absence of a complementary sequence. Remaining linear DNA constructs after ligation are removed by treating with Exonuclease I and Exonuclease III. Agarose gel electrophoresis of the starting and resulting product is performed to confirm that the DNA construct is circularized.

Example 4: Formulation of Circular ssDNA with LNP

This example describes how to formulate the constructs made as described in the previous examples with a lipid nanoparticle.

Nucleic acid constructs are combined with lipid components via microfluidic devices according to the method of Chen et al. 2012. *J Am Chem Soc.* Volume 134, Issue 16:6948-6951. Briefly, the microfluidic devices are fabricated in polydimethylsiloxane (PDMS) according to standard lithographic procedures (McDonald & Whitesides. 2002. *Accounts Chem Res* Volume 35, Issue 7:491-499). The lipid components, typically containing cationic lipids, cholesterol, helper lipids, polyethylene glycol modified lipids, and lipids facilitating targeting moiety conjugation (optional), are combined and solubilized in 90% ethanol. The nucleic acid constructs are dissolved in buffer. The nucleic acid solution, the lipid solution, and phosphate buffer saline (PBS) are injected into the microfluidic device. The freshly prepared LNPs are dialyzed against PBS buffer using membranes with MWCO of 3.5kD to remove ethanol and exchange buffer.

The LNPs are characterized in terms of effective diameter, polydispersity, and zeta potential using dynamic light scattering (DLS) (ZetaPALS, Brookhaven Instruments, NY, 15-mW laser, incident beam 676 nm); and total nucleic acid concentration is determined using Quant-iT™ OliGreen® ssDNA Assay Kit according to the manufacturer protocols (ThermoFisher Scientific, 011492).

Example 5: Assessment of Innate Immune Response in Cells In Vitro

This example describes how to test gene expression, as well as how to determine a construct's effect on the innate immune response of cultured cells.

Experimental constructs are prepared as in examples 1-4 above. The constructs and controls are administered via electroporation at multiple concentrations to cells selected from HEK, keratinocytes, macrophages, T cells and epithelial cells. After electroporation the cells are moved to the final culture vessels. Constructs formulated with LNPs are directly administered to the cells in well plates.

To determine expression of constructs encoding the fluorescent reporter mCherry, cells are first washed with PBS before flow cytometric analysis. All flow cytometry is performed on MACSQuant VYB by Miltenyi. For detection of mCherry signal, a yellow laser (wavelength 561 nm) is used for excitation and a 615/620 nm emission filter is used. 20,000 events are recorded for each sample and data is analyzed using Flowjo V.9.0 software. Cells are first gated on FSC-A and SSC-A plot to remove cell debris. The population is further plotted on an FSC-A and FSC-H plot to circumscribe the single cell population. Finally, a bivariate plot between the fluorescent signal expressing and non-expressing cells is used to determine the percentage of expressing cells. A distribution of expressing cells is used to determine the level of expression within each cell. Expression analysis is performed at multiple time points.

qPCR is performed on cells to determine the RNA level of IFN-b in the test cells as described in Jakobsen et al. 2013. *Proc Natl Acad Sci USA* Volume 110, Issue 48:E4571-80. Briefly, the probe-primer sets used in qPCR are human IFN-b (ThermoFisher, Hs01077958_s1) and b-actin (ThermoFisher, Hs00357333_g1). The analyses are performed using pre-made Taqman assays and the RNA-to-Ct one step kit (Applied Biosystems). qPCR is performed on an MX3005 system (Stratagene). RNA expression is normalized to b-actin and to the relevant untreated control. Data are stated as the mean±SEM from biological replicates.

ELISA is performed on cell supernatants according to the manufacturer protocol to determine the secreted level of IFN-b.

Example 6. Preparation of Circular Single Stranded DNA (ssDNA)

This Example demonstrates preparation of circular ssDNA.

Plasmid DNA (1 ng/50 ul PCR reaction) was used as a template for PCR amplification using Q5 polymerase (M0494L, New England Biolabs). Other commercially available polymerases may also be used. In addition to containing sequences complementary to the plasmid, primers contained additional sequences useful in downstream processes:
   a. Nicking enzyme(s) recognition sequence;
   b. Restriction enzyme recognition sequence (e.g. BsaI, KpnI, or NheI), used to create sticky-ends in the DNA after restriction enzyme digestion and facilitate DNA circularization; and
   c. Additional bases (e.g., 5'-CCGTGGTCCTTC-3') (SEQ ID NO: 40) to increase restriction enzyme digestion efficiency.

The PCR product was purified using DNA purification columns (M0494L, Zymo Research). DNA was digested, in an overnight reaction, using the restriction enzyme corresponding to the restriction enzyme recognition sequence, for instance, BsaI—HF-V2 (R3733L, New England Biolabs). DNA was then purified using DNA purification columns.

Digested DNA was circularized using T4 DNA ligase (M0202M, New England Biolabs) for one hour at room temperature. Non-circularized DNA was degraded by incubating the DNA with T5 exonuclease (M0663L, New England Biolabs) for one hour at 37° C. T5 exonuclease was used to digest linear dsDNA but not circular dsDNA. DNA was purified using DNA purification columns. Other similar methods may also be used, for instance agarose gel purification.

Figure 11:
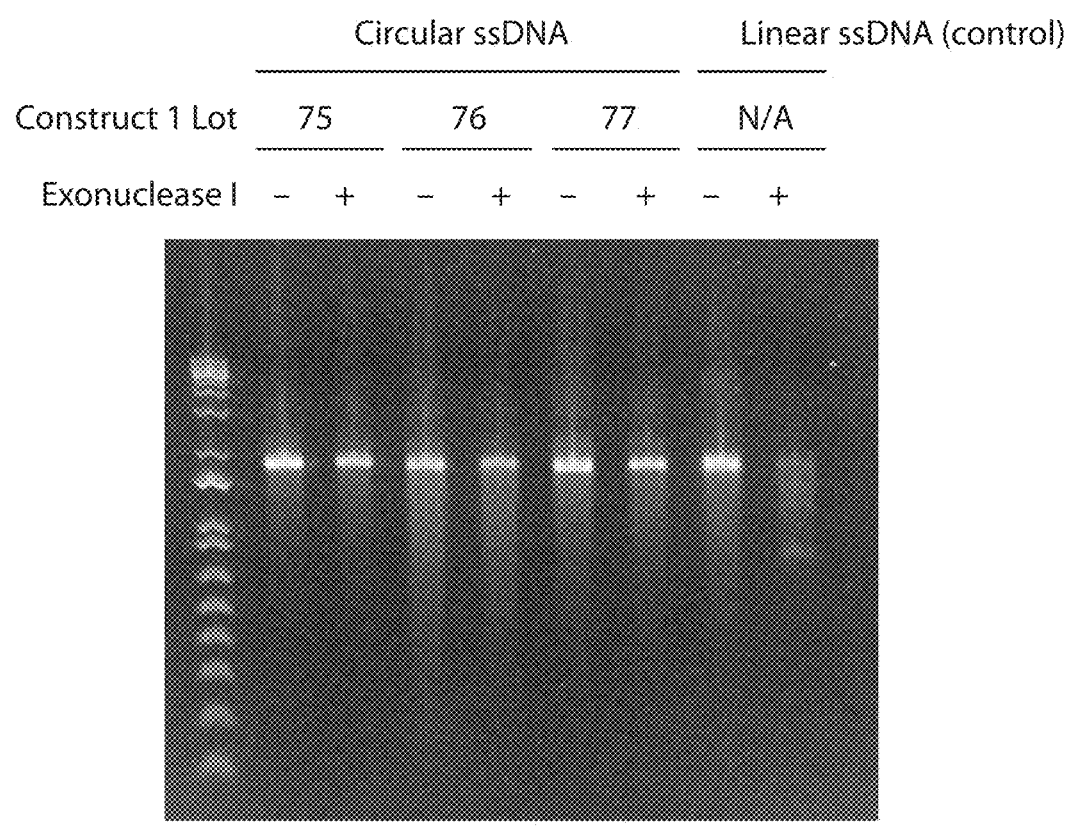
FIG. 11 is a DNA gel electrophoresis image showing circular ssDNA and linear ssDNA incubated in the absence (−) and presence (+) of Exonuclease I. Circular ssDNA preparations were resistant to degradation by Exonuclease I, while linear ssDNA was degraded in the presence of Exonuclease I.
Figure 12A:
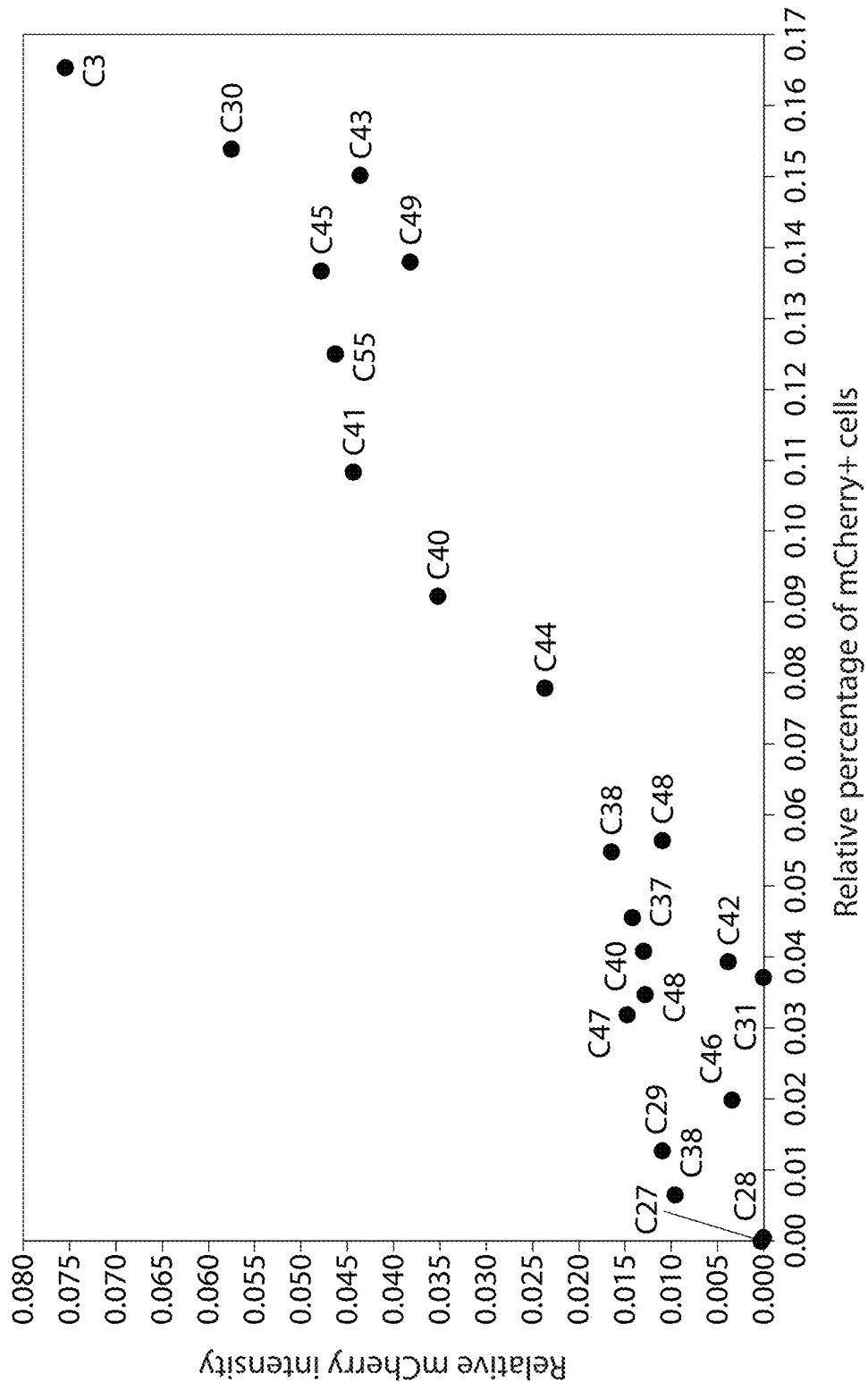
Figure 12B:
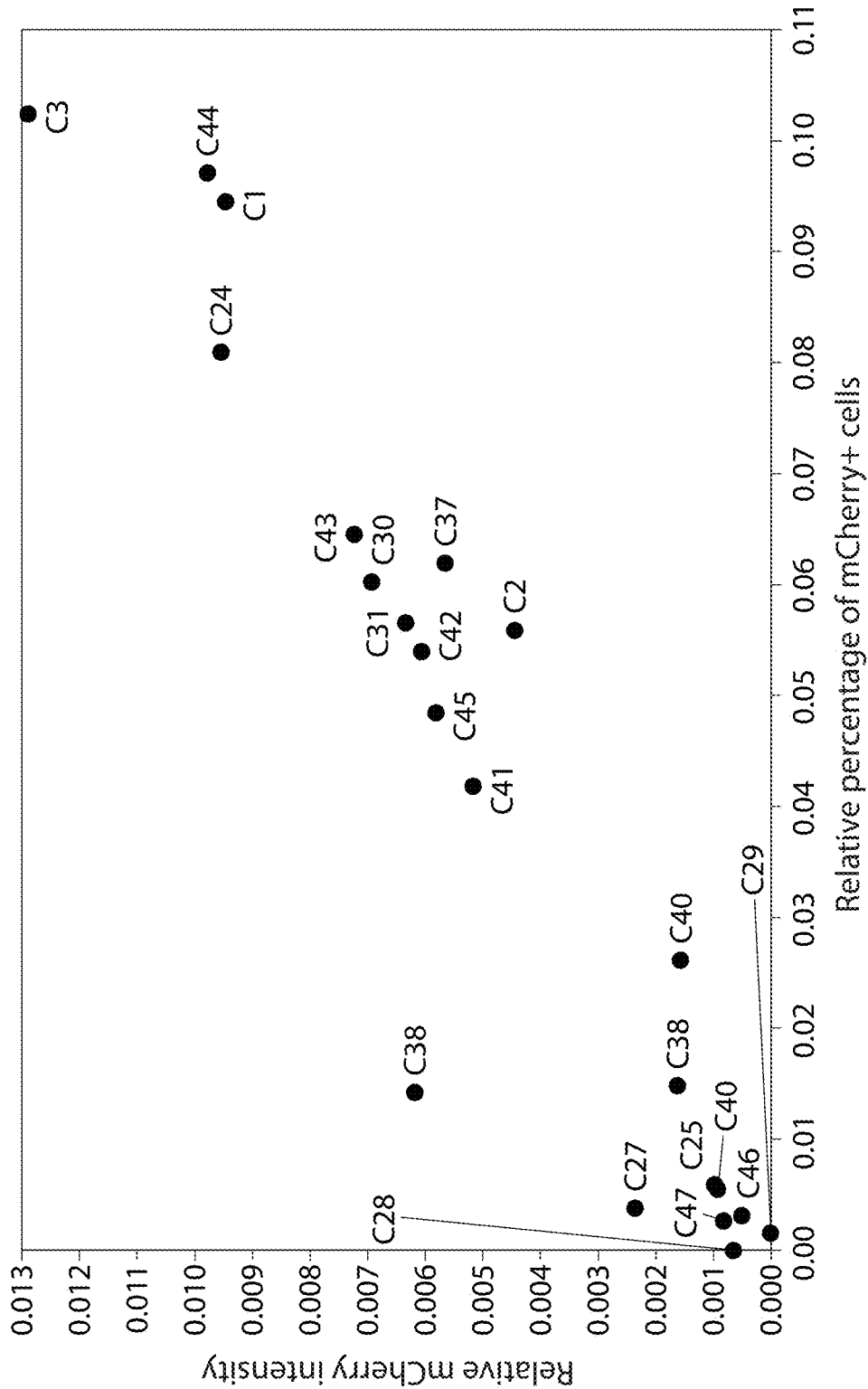
Figure 12C:
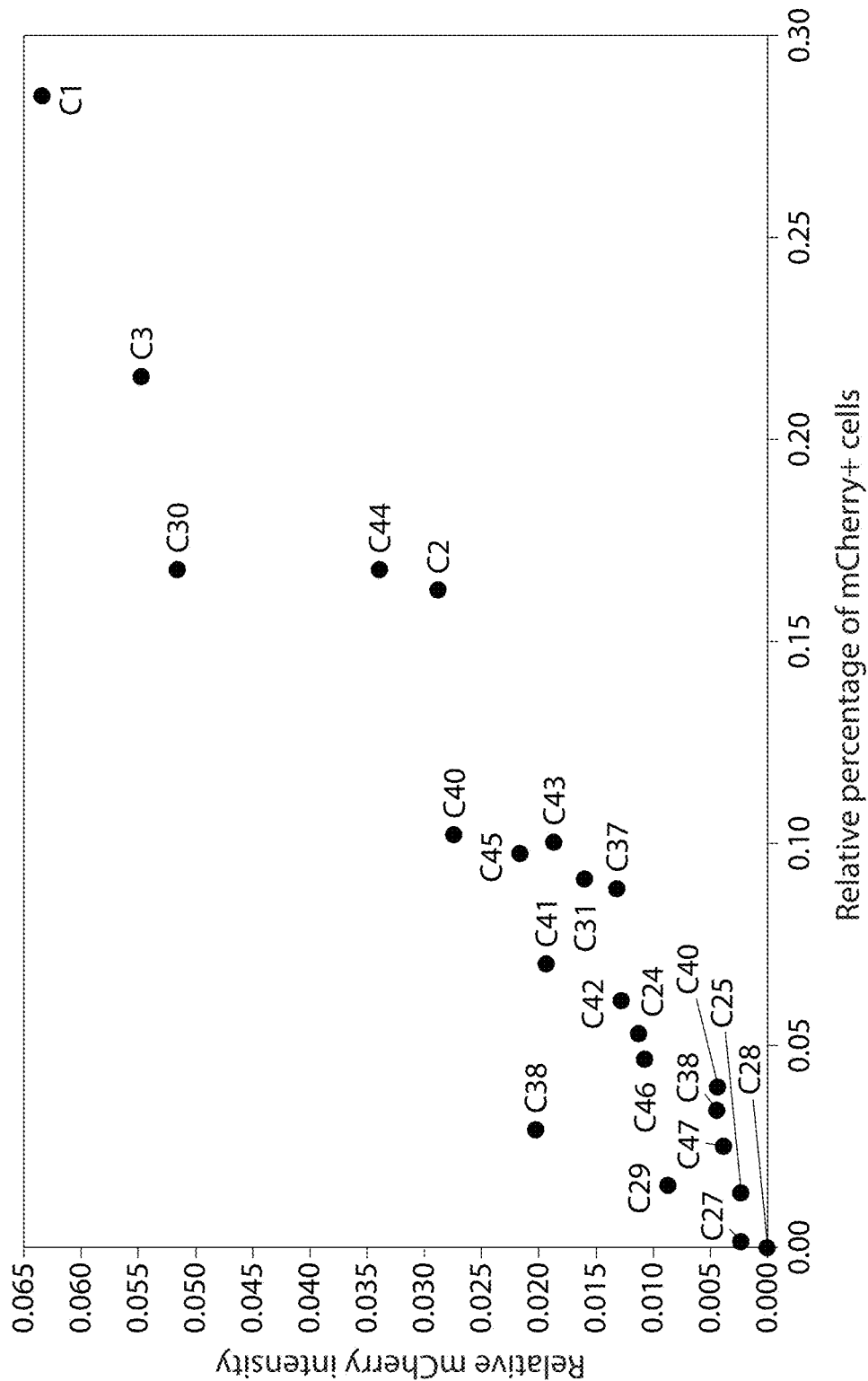

Circular dsDNA was incubated with a nicking endonuclease (e.g. Nb.BsrDI, R0648L, New England Biolabs). This endonuclease is sequence specific and cleaves only one strand on a dsDNA molecule. The nicked DNA strand was removed by incubating the DNA with T7 exonuclease (New England Biolabs, M0263) of 30 min at 25° C. Exonuclease III (M0206, New England Biolabs) may also be used, e.g., for 30 min at 37° C. Incubation of DNA with exonucleases is described in further detail in Example 7. A sample of the reaction was run in an agarose gel to verify production of circular ssDNA (nicked DNA runs slower than circular ssDNA). Circular ssDNA was directly purified using purification columns (Oligo Clean & Concentrator, D4061. Zymo Research) or agarose gel purification (Long ssDNA Gel Extraction Kit for 3kb, DS640, DiagnoCine). Circular ssDNA prepared by the methods described herein was shown to be resistant to degradation by Exonuclease I, while linear ssDNA was degraded by Exonuclease I (FIG. 11).

Analysis of the composition and purity of both single and double-stranded DNA forms was performed on an Agilent 5300 Fragment Analyzer using the CRISPR Discovery Kit (DNF-930-K1000CP). The dsDNA inlet buffer and running gel with intercalating dye was prepared fresh each day, while the marker tray with mineral oil overlay and capillary conditioning solution were prepared fresh each month. The buffers were prepared to the manufacturer's specifications. Single stranded DNA samples were diluted in water to a final concentration of 1 ng/uL and double stranded DNA samples were diluted in water to a final concentration of 100 pg/uL. For each sample well, 2 µL of the DNA samples were added to 22 µL of Dilution Buffer (0.1× TE), and each sample was run with 2-4 replicates, with one well used for the MDK DNA ladder. The samples were run via the instrument controller software using default settings of the CRISPR Discovery Method (CRP-910-33).

Sample traces were analyzed using the ProSize Data Analysis Software v4.0.2.7. Peak Analysis conditions were set at a 'Peak Width (sec)' of 15 and a 'Min. peak height (RFU)' of 75, #Extra Valley Points of 3, and with 'Valley to Valley Baseline?' turned off. Manual baseline was set at −2 min from the lower marker and +2 min to from the upper marker. Peaks were automatically detected by the software under these conditions, and peaks widths were chosen by the software except for instances where manual adjustments were required to due to broad peaks, peak shoulders, or to multiple peaks within a narrow size range.

Circular ssDNA and circular dsDNA of two constructs (CONSTRUCT029) and (CONSTRUCT001) were purified and analyzed using the methods described in this Example. Each DNA preparation was analyzed in 4× replicates on the Fragment Analyzer, and the sample traces are shown in FIGS. 3-9.

Figure 3:
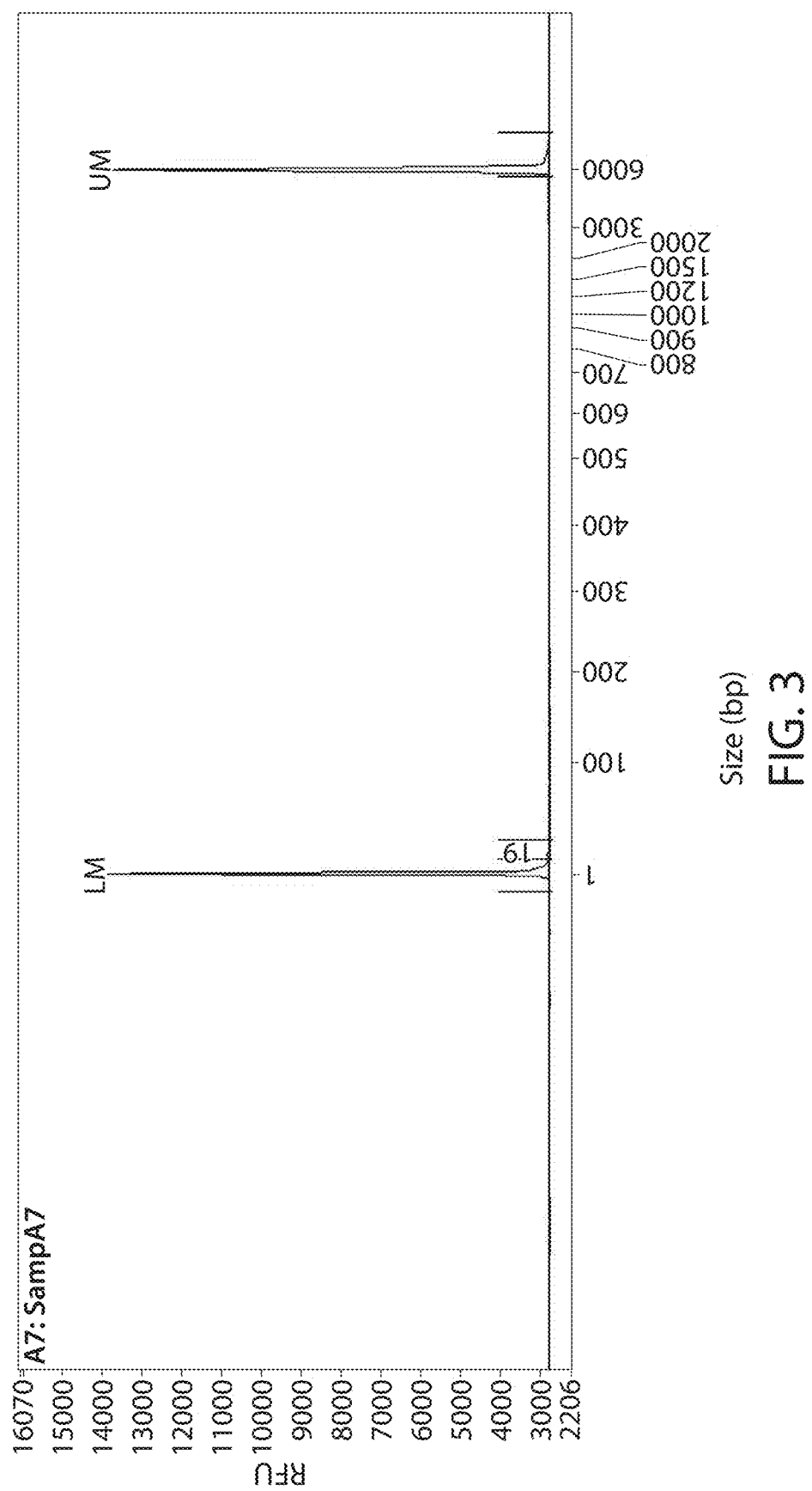
FIGS. 3-8 are a set of traces obtained using the Fragment Analyzer of a blank well (FIG. 3) and preparations of CONSTRUCT029 circular ssDNA (FIG. 4), CONSTRUCT029 circular dsDNA (FIG. 5), CONSTRUCT001 circular dsDNA (FIG. 6), CONSTRUCT001 circular ssDNA preparation #1 (FIG. 7), and CONSTRUCT001 circular ssDNA preparation #2 (FIG. 8). LM: Lower Marker, UM: Upper Marker.
Figure 4:
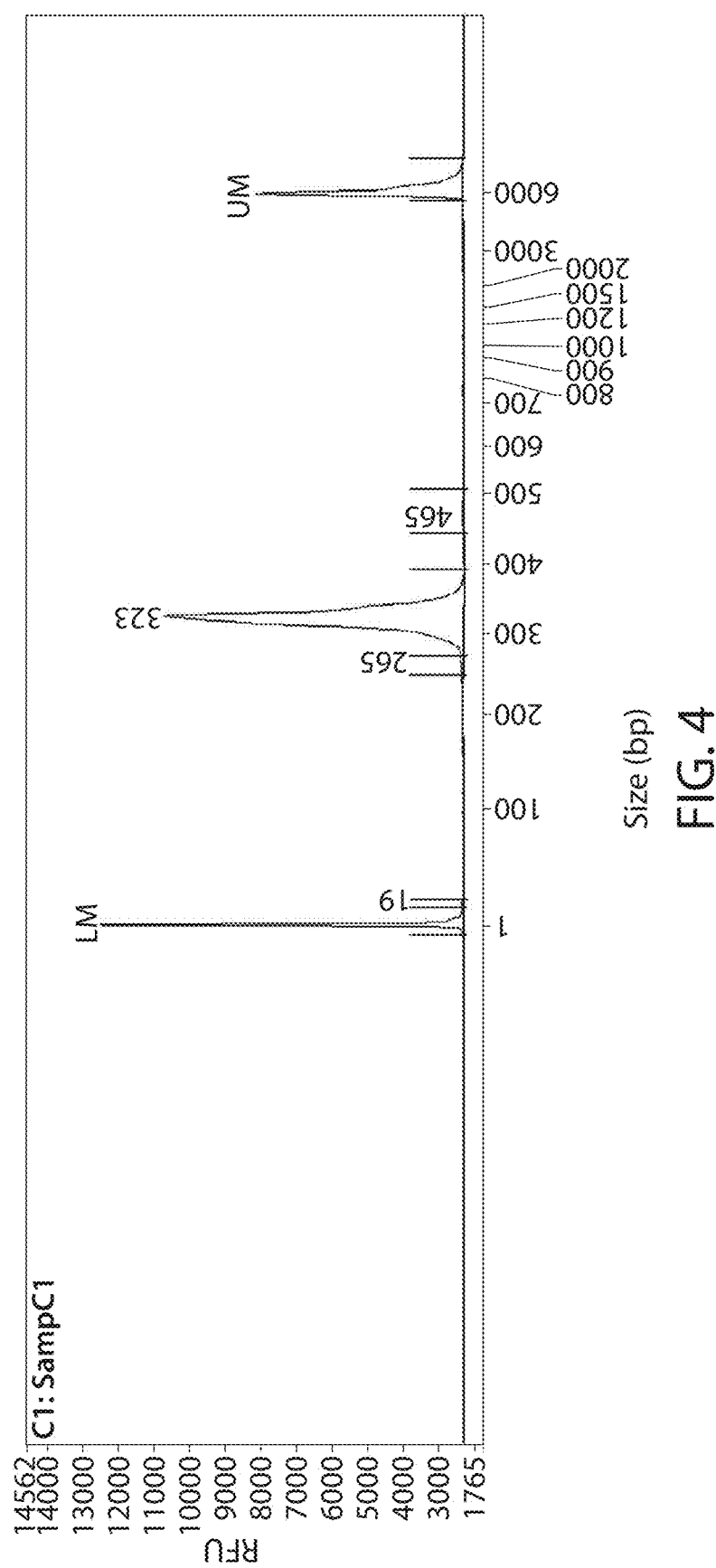
Figure 5:
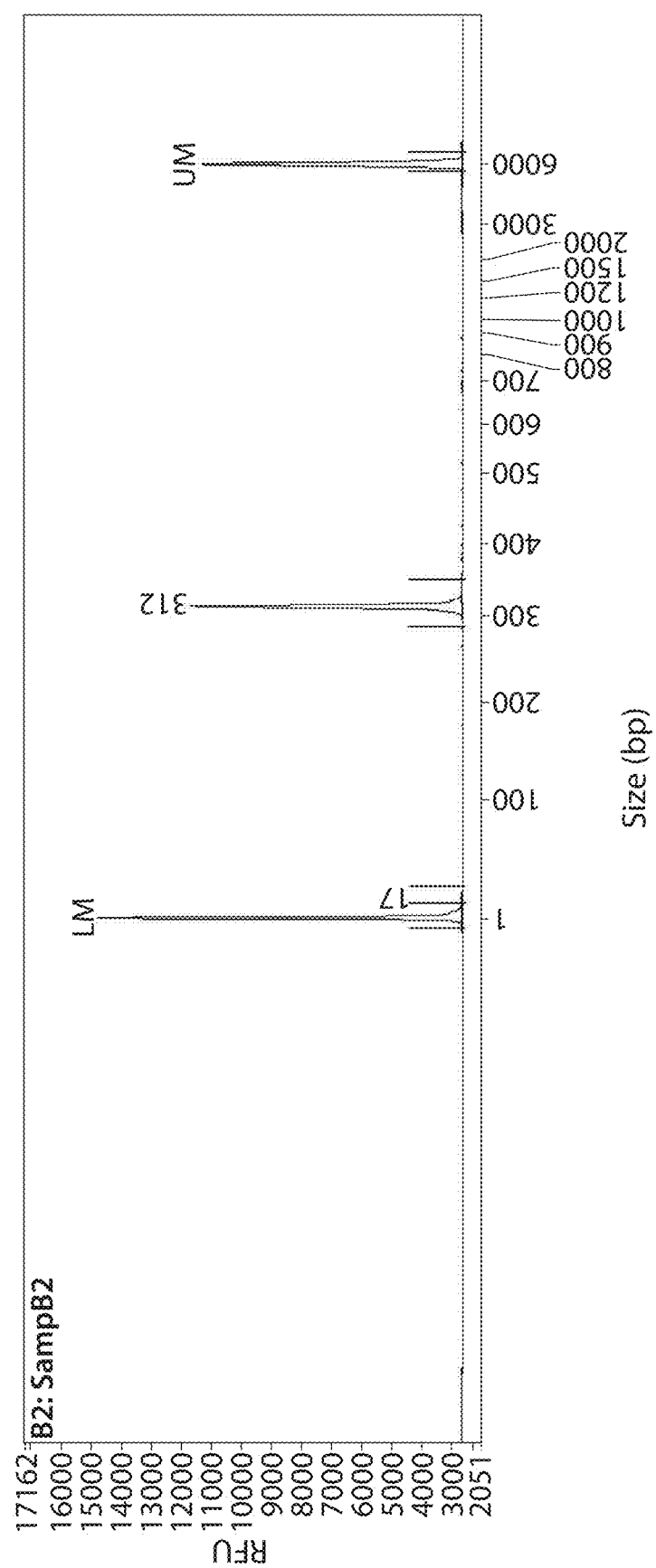

Notable Peaks Include:
  Lower Marker (LM)=1 bp,
  Residual peak at 19 bp (this peak was also present in the blank wells and not derived from the DNA preparation, and hence, was not considered in the final peak quantification values),
  Primary peak,
  Secondary peaks (impurities), and
  Upper Marker (UM)=6000 bp The trace of the blank well shows presence of a peak at 19 bp only (FIG. 3). CONSTRUCT029 circular ssDNA was quantified at 98.8% of the total peak area (n=4; FIG. 4; Table 4). CONSTRUCT029 circular dsDNA, CONSTRUCT001 circular dsDNA, CONSTRUCT001 circular ssDNA preparation #1, and CONSTRUCT001 circular ssDNA preparation #2 were each quantified at 100% of the respective sample, i.e., no impurities were detected (n=4; FIGS. 5-8).

Figure 9:
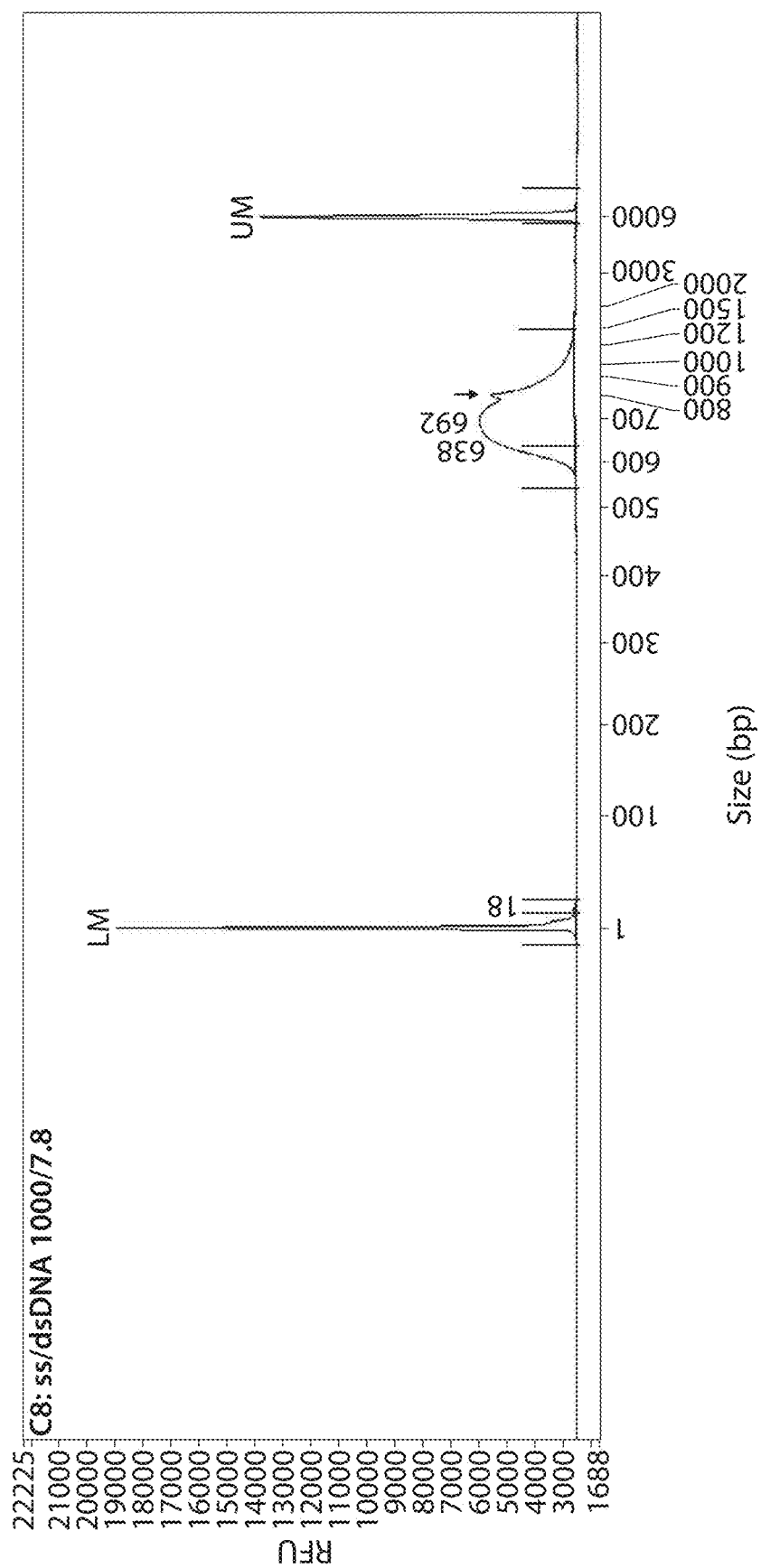
FIG. 9 is a trace of obtained when 7.8 pg of CONSTRUCT001 circular dsDNA were spiked per 1 ng of CONSTRUCT001 circular ssDNA. The peak corresponding to circular dsDNA is indicated by an arrow.

To assess identification of circular dsDNA contamination in circular ssDNA preparations, 7.8 pg of CONSTRUCT001 circular dsDNA were spiked per 1 ng of CONSTRUCT001 circular ssDNA, the lowest concentration tested in which the peaks can be reliably differentiated. The peak corresponding to circular dsDNA is indicated by a red arrow (FIG. 9). The impurity resolution was >6 pg/uL.

TABLE 4

Relative Peak Quantification of CONSTRUCT029 circular ssDNA.

| | | % (Conc.) | | | | |
|---|---|---|---|---|---|---|
| Peak | Size (bp) | Rep 1 | Rep 2 | Rep 3 | Rep 4 | AVG |
| 1 | 1 (LM) | 0.3 | 0.9 | 0.9 | | |
| 2 | 263 | 0.4 | | | 1.1 | |
| 3 | 272 | 99.3 | 98.4 | 98.4 | 98.9 | 98.8 |
| 4 | 325 | 0 | 0.7 | 0.7 | | |
| 5 | 472 | | | | | |
| 6 | 6000 (UM) | | | | | |

LM: Lower Marker,
UM: Upper Marker

In summary, this Example describes successful preparation of circular ssDNA having a high purity from plasmid DNA.

Example 7. Incubation of DNA with Exonucleases

This Example describes the effects of Exonuclease III and T7 exonuclease on nicked circular dsDNA. As described above, certain manufacturing methods described herein involve treating nicked circular dsDNA with one of these exonucleases to remove the nicked strand, yielding circular ssDNA. Although these enzymes are generally thought of as being specific for linear or nicked DNA, this Example demonstrates that these enzymes also have some activity against circular ssDNA. This Example illustrates suitable digestion conditions that reduce the amount of nicked DNA while preserving high levels of circular ssDNA.

Figure 10:
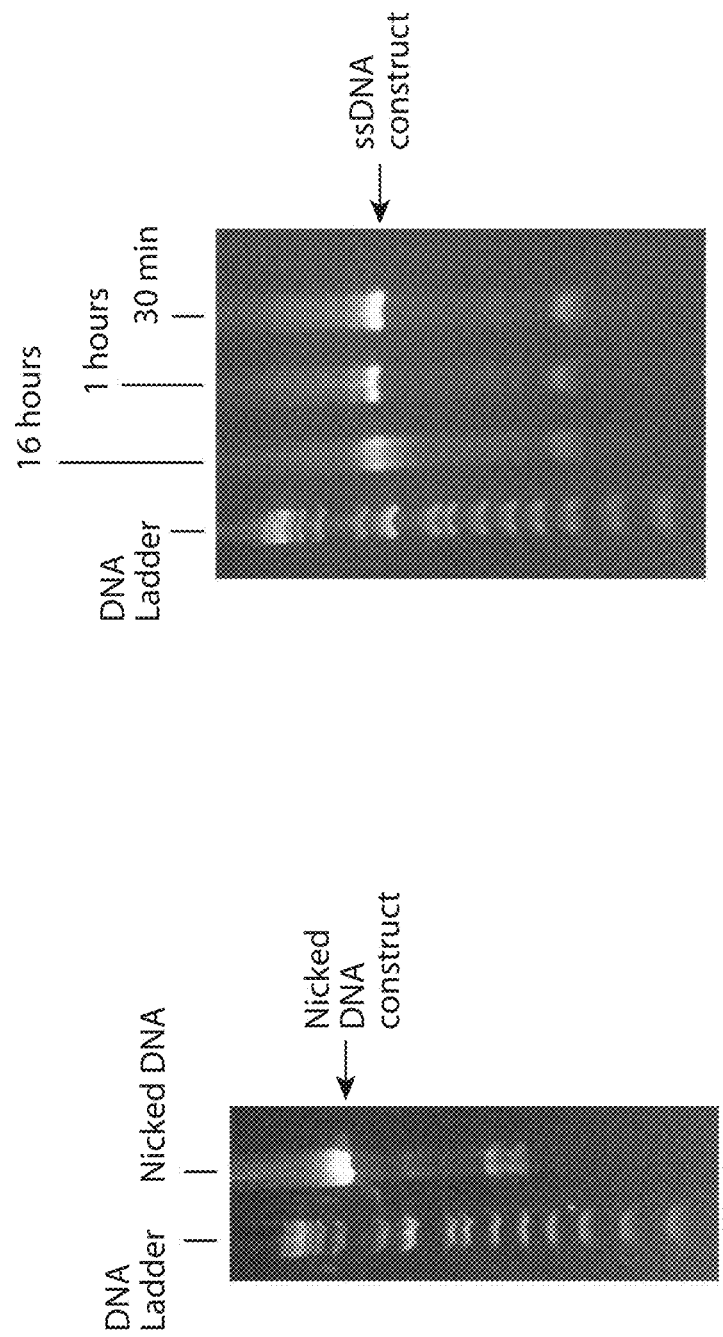
FIG. 10A and FIG. 10B depict a set of DNA gel electrophoresis images.

7.2 µg of circular dsDNA, in 100 µl of 1× rCutSmart buffer (NEB, B6004S), were nicked with 20 units of Nb.BsrDI (NEB, R0648L) for 30 minutes at 37° C. The enzyme was heat-inactivated by incubating the reaction at 80° C. for 20 minutes. FIG. 10A depicts the nicked DNA construct as visualized through DNA gel electrophoresis. Nicked DNA was converted into ssDNA by incubating a sample of 50 µl (3.6 µg of DNA) with 7.5 units of T7 exonuclease (NEB, M0263L) at 25° C. for 30 min (FIG. 10B; lane 4), 1 hour (FIG. 10B; lane 3) 16 hours (FIG. 10B; lane 2). A 30 min incubation resulted in loss of detectable nicked DNA and persistence of high amounts of circular ssDNA. In contrast, a 16 hour incubation period with T7 exonuclease led to some degradation of circular single stranded DNA.

This example also describes the effects of Exonuclease I on linear and circular dsDNA. FIG. 11 shows Exonuclease I degradation of linear and circular ssDNA forms of CONSTRUCT001. Circular ssDNA prepared by the methods herein was shown to be resistant to degradation by Exonuclease I, while linear ssDNA was degraded by Exonuclease I. This highlights the general resistance of circular DNAs to exonucleases, which otherwise contribute to the intracellular degradation of DNAs, including of therapeutic constructs.

Example 8: Assessment of Reporter Gene Expression In Vitro

This Example describes successful gene expression using circular ssDNA constructs in cultured cells.

Experimental constructs were prepared as in Examples 1-4 above. The circular ssDNA constructs and controls used in this Example are listed in Table 5. The constructs and controls were administered via electroporation with the Neon Transfection System (ThermoFisher, MPK5000) at multiple concentrations. Recipient cell lines included HEKa keratinocytes (American Type Culture Collection (ATCC), PCS-200-011), HepG2 hepatocytes (ATCC, HB-8065), U2OS osteosarcoma cells (ATCC, HTB-96), and HEK293 epithelial cells (ATCC, CRL-1573). For electroporation experiments, approximately $5 \times 10^6$ cells were electroporated at 1500 volts for 30 ms in DPBS buffer. After electroporation the cells were moved to the final culture vessels. Constructs formulated with LNPs were directly administered to the cells in well plates.

Experimental constructs and controls were also administered via lipid transfection (lipofection). Lipofection for DNA was performed using the Lipofectamine3000 transfection reagent (#L3000001, ThermoFisher) in HEKa, HepG2, HEK293, and U2OS cells according to manufacturer's instructions. A 1:2:3 ratio of DNA:P3000:Lipofectamine3000 was used for all DNA constructs and controls. 10,000 cells were pre-seeded into each well of 96-well plates one day before transfection. Transfection was performed when cells reached roughly 80 to 90% confluence. For each well of a 96-well plate, 3× Lipofectamine3000 was first diluted in 5 µL of Opti-MEM™ I Reduced Serum Medium (#31985070, ThermoFisher). DNA was diluted in 5 uL Opti-MEM™ I Reduced Serum Medium with 2× P3000 reagent. The DNA was then added into the Lipofectamine3000 containing Opti-MEM™ I Reduced Serum Medium and mixed gently by pipetting. After incubating for 15 minutes at room temperature, the DNA-Lipofectamine3000 complex was added to target cells with full culture medium in a dropwise manner to different areas of the well. The plate was gently rocked back-and-forth and side-to-side to evenly distribute the DNA-Lipofectamine3000 complex. Following transfection, cells were incubated in a C02 tissue culture incubator, and culture medium was changed 6 to 8 hours after transfection.

To determine expression of constructs encoding the fluorescent reporter mCherry, cells were first washed with PBS before flow cytometric analysis. All flow cytometry was performed on MACSQuant VYB by Miltenyi. For detection of mCherry signal, a yellow laser (wavelength 561 nm) was used for excitation and a 615/620 nm emission filter was

TABLE 5

Circular single-stranded DNA constructs with distinct combinations of sequence elements. "C001" corresponds to CONSTRUCT001, "C002" corresponds to CONSTRUCT002, etc.

| Name | Length (nt) | 5' Element A | 5' Element B | Promoter | Transgene | PolyA signal | 3' Element A | 3' Element B | 3' Element C |
|---|---|---|---|---|---|---|---|---|---|
| C001 | 2191 | | | EF1a | mCherry | bGH | Nicking site(s) | | |
| C002 | 2263 | SV40 Enhancer | | EF1a | mCherry | bGH | Nicking site(s) | | |
| C003 | 2301 | 3NF | | EF1a | mCherry | bGH | 3NF | Nicking site(s) | |
| C010 | 2304 | Anellovirus Hairpin | | EF1a | mCherry | bGH | Nicking site(s) | | |
| C024 | 2416 | Anellovirus Hairpin | 3NF | EF1a | mCherry | bGH | Nicking site(s) | 3NF | |
| C025 | 2376 | SV40 Enhancer | Anellovirus Hairpin | EF1a | mCherry | bGH | Nicking site(s) | | |
| C027 | 2191 | | | EF1a | mCherry (no ATG) | bGH | Nicking site(s) | | |
| C028 | 1012 | | | | mCherry | bGH | Nicking site(s) | | |
| C029 | 787 | | | | mCherry | | Nicking site(s) | | |
| C030 | 2380 | SV40 Enhancer | | EF1a | mCherry | bGH | Nicking site(s) | SV40 Enhancer | |
| C031 | 2258 | | | EF1a | mCherry | bGH | Nicking site(s) | SV40 Enhancer | |
| C037 | 2299 | | | EF1a | mCherry | bGH | Nicking site(s) | Anellovirus Hairpin | |
| C038 | 2462 | Anellovirus Hairpin | | EF1a | mCherry | bGH | Nicking site(s) | Anellovirus Hairpin | |
| C040 | 2534 | Anellovirus Hairpin | SV40 Enhancer | EF1a | mCherry | bGH | Nicking site(s) | Anellovirus Hairpin | |
| C041 | 2416 | 3NF | | EF1a | mCherry | bGH | Nicking site(s) | 3NF | Anellovirus Hairpin |
| C042 | 2554 | Anellovirus Hairpin | 3NF | EF1a | mCherry | bGH | Nicking site(s) | 3NF | Anellovirus Hairpin |
| C043 | 2420 | 3NF | 3NF | EF1a | mCherry | bGH | Nicking site(s) | 3NF | 3NF |
| C044 | 2308 | 3NF | 3NF | EF1a | mCherry | bGH | Nicking site(s) | | |
| C045 | 2237 | 3NF | | EF1a | mCherry | bGH | Nicking site(s) | | | used. 20,000 events were recorded for each sample and data were analyzed using Flowjo V.9.0 software. Cells were first gated on FSC-A and SSC-A plot to remove cell debris. The population was further plotted on an FSC-A and FSC-H plot to circumscribe the single cell population. Finally, a bivariate plot between the fluorescent signal expressing and non-expressing cells was used to determine the percentage of expressing cells. A distribution of expressing cells was used to determine the level of expression within each cell. Expression analysis was performed at multiple time points.

FIGS. 12A-12D show expression of circular ssDNA constructs in HEK293, HepG2, U20S, and HEKa cells, respectively. Positive correlations were observed between the proportion of reporter-positive cells (X-axis) and the fluorescent intensity of such cells (Y-axis), normalized to the expression of CONSTRUCT001 plasmid. These results demonstrate that circular ssDNAs with multiple different sequence elements (Table 5) express a reporter gene (mCherry) with similar expression profiles.

Example 9: Assessment of Innate Immune Response in Cells In Vitro

This example describes the effect of circular ssDNA constructs on the innate immune response of cultured cells.

Experimental constructs were prepared as in Examples 1-4 above, then administered to cells as in Example 8 above. qPCR was performed on cells to determine the RNA level of cytokines IFN-b, IL-6, IL-1b, TNF-α, and CXCL10 in the test cells. Briefly, the probe-primer sets used in qPCR were human IFN-b (forward sequence: CTTGGATTCCTA-CAAAGAAGCAGC (SEQ ID NO: 41); reverse sequence: TCCTCCTTCTGGAACTGCTGCA) (SEQ ID NO: 42); human IL-6 (forward sequence: AGACAGCCACT-CACCTCTTCAG (SEQ ID NO: 43); reverse sequence: TTCTGCCAGTGCCTCTTTGCTG (SEQ ID NO: 44)); human IL-1b (forward sequence: CCACAGACCTTCCAG-GAGAATG (SEQ ID NO: 45); reverse sequence: GTGCAGTTCAGTGATCGTACAGG (SEQ ID NO: 46)); human TNF-α (forward sequence: CTCTTCTGCCTGCTGCACTTTG (SEQ ID NO: 47); reverse sequence: ATGGGCTACAGGCTTGTCACTC (SEQ ID NO: 48)); human CXCL10 (forward sequence: GGTGAGAAGAGATGTCTGAATCC (SEQ ID NO: 49); reverse sequence: GTCCATCCTTGGAAGCACTGCA (SEQ ID NO: 50)); human CCL20 (forward sequence: AAGTTGTCTGTGTGCGCAAATCC (SEQ ID NO: 51); reverse sequence: CCATTCCAGAAAAGCCACAGTTTT (SEQ ID NO: 52)), human GAPDH (forward sequence: GTCTCCTCTGACTTCAACAGCG (SEQ ID NO: 53); reverse sequence: ACCACCCTGTTGCTGTAGCCAA (SEQ ID NO: 54)). The analyses were performed using the QuantStudio7 Flex Real-time PCR System with SYBR Select Master Mix from Life Technologies Corporation. RNA expression was normalized to GAPDH and expressed as fold-changes relative to the relevant untreated control.

Figure 13A:
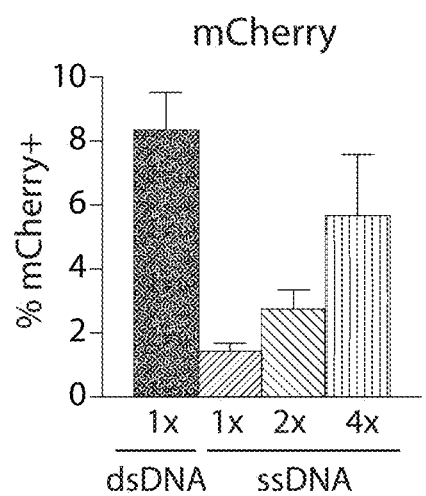
FIGS. 13A-13B are a series of graphs depicting the percentage of HEKa cells expressing mCherry following lipofection with CONSTRUCT001. CONSTRUCT001 was produced as circular ssDNA and circular dsDNA, and relative molarities of ssDNA or dsDNA are shown (e.g., 1×, 2×, or 4×).
Figure 13B:
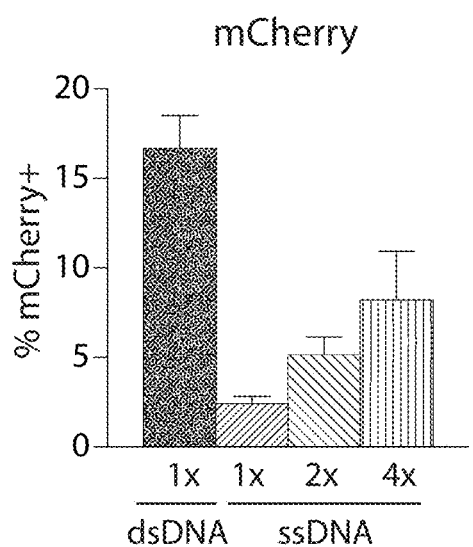

Expression and immunogenicity of CONSTRUCT001 (which comprises the transgene mCherry), produced as circular ssDNA and circular dsDNA and delivered to HEKa cells via lipofection, are shown in FIGS. 13A-13B and 14A-14E. Circular ssDNA was expressed at a lower level, as defined by the proportion of mCherry+cells, than equal molarities ("1×") and equal masses ("2×") of circular dsDNA (FIGS. 13A-13B). Conversely, as shown in FIGS. 14A-14E, equal molarities and masses of circular ssDNA were considerably less immunogenic than circular dsDNA, as evidenced by reduced production of interferons (i.e., IFN-β) and pro-inflammatory cytokines and chemokines (e.g., IL-6). These results demonstrate reduced innate immunogenicity of circular ssDNA relative to circular dsDNA.

Example 10. Preparation of Circular Single Stranded DNA (ssDNA) with Chemical Modification This example describes preparation and expression profiling of circular ssDNA with a chemical modification.

DNA was nicked by mixing 4 µg of circular dsDNA and 20 units of Nb.BsrDI (NEB, R0648) in 50 ul of 1× CutSmart buffer (NEB, B6004). Reactions were incubated for 30 minutes at 37° C.

DNA was methylated by adding 150 µl of methyltransferase reaction mix (S-adenosylmethionine to a final concentration of 160 µM and 20 units of EcoGII methyltransferase (NEB, M0603)) to the nicked DNA in 1× CutSmart buffer. Reactions were incubated for one hour at 37° C.

DNA was purified using Zymo DNA purification columns as previously described. Nicked circular methylated dsDNA was converted into methylated circular ssDNA form by combining 4 µg of DNA with 15 units of T7 Exonuclease (NEB, M0263) in 50 µl of 1× CutSmart buffer and incubating the reactions for 30 min at 25° C. DNA was purified by gel electrophoresis as previously described.

Figure 15:
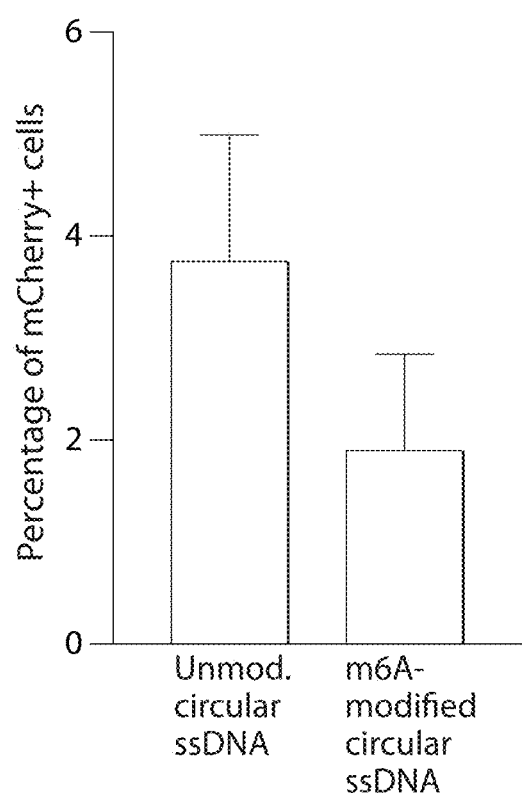
FIG. 15 is a graph depicting the percentages of mCherry+ cells following transfection with CONSTRUCT001 in two forms: unmodified single-stranded circular DNA, and single-stranded circular with m6A ($N^6$-methyladenosine) DNA modification.

FIG. 15 shows expression of CONSTRUCT00I in two forms: unmodified single-stranded circular DNA, and single-stranded circular with m6A ($N^6$-methyladenosine) DNA modification. The chemically modified circular single-stranded DNA retained detectable function, as evidenced by the expression of mCherry reporter in transfected cells. This result indicates that transgene expression from circular ssDNA can be influenced by chemical modification.

Example 11: Computational Prediction of DNA Secondary Structure

This example describes modeling of secondary structure of circular ssDNA.

Double stranded regions formed by a ssDNA described herein was determined as described by Lorenz et al. 2011. ViennaRNA Package 2.0. *Algorithms for Molecular Biology*, Volume 6, Article 26. The RNAFold web server (http://rna.tbi.univie.ac.at//cgi-bin/RNAWebSuite/RNAfold.cgi) was used to predict double stranded regions of CONSTRUCT001 described herein. Briefly, default "fold algorithms" and "basic options" were used to model the secondary structure of CONSTRUCT00I on the basis of minimum free energy. Default "advanced folding options" were used, except for the selection of "DNA" and "circular" parameters.

FIGS. 16A-16D show the resulting structure prediction of CONSTRUCT001 as circular ssDNA. No regions of double-strandedness greater than 16 continuous base pairs were predicted. This result suggests that circular ssDNA constructs can be produced which lack long regions of double-strandedness associated with stimulation of the innate immune response under physiological conditions (see Luecke et al. 2017. *EMBO Reports* Volume 18, Issue 10:1707-1715).

Example 12: Purity Levels of cssDNA Construct

Circular single stranded DNA constructs were produced as described in Examples 1-4. Their levels and purity were determined. Purity was determined using absorbance ratios, specifically A260/A280 and A230/A260 (Table 6).

TABLE 6

Purity measurements of sense (SEN) and antisense (ANS) strands of circular single-stranded DNA constructs.

| Construct | ng/ul | ug total | 260/280 ratio | 230/260 ratio |
| --- | --- | --- | --- | --- |
| C001-circSS-SEN | 46.3 | 2.3 | 1.69 | 1.79 |
| C001-circSS-SEN | 18.6 | 1.9 | 1.63 | 0.89 |
| C001-circSS-ANS | 49 | 7.1 | 1.76 | 0.34 |
| C029-circSS-SEN | 51.9 | 5.7 | 1.72 | 1.68 |
| C029-circSS-ANS | 46.1 | 5.3 | 1.63 | 1.64 |

All publications, patents, and patent applications cited herein are incorporated by reference in their entirety to the same extent as if each individual publication, patent, or patent application was specifically and individually indicated to be incorporated by reference. In the event of a conflict between a term herein and a term in an incorporated reference, the term herein controls.

The invention claimed is:

1. A pharmaceutical formulation comprising:
  a lipid nanoparticle (LNP) comprising a single stranded DNA (ssDNA), wherein the ssDNA:
    (a) encodes only one protein, which is a therapeutic protein,
    (b) is covalently closed,
    (c) does not form a double stranded structure longer than 40 base pairs,
    (d) is at least 200 nucleotides in length, and
    (e) does not comprise a protelomerase target sequence;
  wherein:
    (i) at least 95% by mass of total DNA in the composition is the ssDNA that is covalently closed;
    (ii) the pharmaceutical formulation is free of polypeptides; and
    (iii) the therapeutic protein is expressed when the ssDNA is introduced into a target cell.

2. The pharmaceutical formulation of claim 1, wherein the ssDNA comprises a promoter sequence operably linked to a sequence encoding the therapeutic protein.

3. The pharmaceutical formulation of claim 1, wherein the therapeutic protein is selected from the group consisting of: a transcription factor, a chromatin remodeling factor, an antigen, a peptide, a hormone, an enzyme, an antibody, a receptor ligand, a receptor, a clotting factor, and a membrane protein.

4. The pharmaceutical formulation of claim 1, wherein the ssDNA has a GC content of 30-40%, 40-50%, 50-60%, or 60-70%.

5. The pharmaceutical formulation of claim 1, wherein the ssDNA further comprises a nuclear targeting sequence (NTS).

6. The pharmaceutical formulation of claim 1, wherein the ssDNA further comprises a maintenance sequence.

7. The pharmaceutical formulation of claim 1, wherein the ssDNA further comprises a second strand motif (SSM).

8. The pharmaceutical formulation of claim 1, wherein the ssDNA comprises between 200 and 3,000 nucleotides.

9. The pharmaceutical formulation of claim 1, wherein the ssDNA comprises between 500 and 2,000 nucleotides.

10. The pharmaceutical formulation of claim 1, wherein the ssDNA is a sense ssDNA strand.

11. The pharmaceutical formulation of claim 1, wherein the ssDNA comprises at least one nucleotide modification.

12. The pharmaceutical formulation of claim 11, wherein the nucleotide modification is 5-formylcytosine.

13. The pharmaceutical formulation of claim 1, wherein the pharmaceutical formulation is formulated for parenteral administration.

14. The pharmaceutical formulation of claim 1, wherein the pharmaceutical formulation is formulated for topical administration.

15. The pharmaceutical formulation of claim 1, wherein the pharmaceutical formulation is free of one or more of: endotoxin, mononucleotides, modified mononucleotides, and double stranded DNA.

16. The pharmaceutical formulation of claim 1, wherein the ssDNA lacks one or both of a bacteriophage packaging site and a bacteriophage origin of replication, or wherein the ssDNA does not encode a bacteriophage capsid gene.

17. A method of delivering a therapeutic protein to a subject, comprising administering to the subject the pharmaceutical formulation of claim 1.

18. The method of claim 17, wherein the method does not result in substantial integration of the ssDNA into the genome of the subject.

19. A pharmaceutical formulation comprising:
  an LNP comprising a single stranded DNA (ssDNA), wherein the ssDNA:
    (a) encodes only one protein, which is a therapeutic protein,
    (b) is covalently closed,
    (c) does not form a double stranded structure longer than 100 base pairs,
    (d) is at least 200 nucleotides in length, and
    (e) does not comprise a protelomerase target sequence;
  wherein:
    (i) at least 95% by mass of total DNA in the composition is the ssDNA that is covalently closed;
    (ii) the pharmaceutical formulation is free of viral protein; and
    (iii) the therapeutic protein is expressed when the ssDNA is introduced into a target cell.

20. The pharmaceutical formulation of claim 3, wherein the antibody is a monoclonal antibody, Fab fragment, or single-chain Fv.

21. A pharmaceutical formulation comprising:
  an LNP comprising a single stranded DNA (ssDNA), wherein the ssDNA:
    (a) encodes a therapeutic protein,
    (b) is covalently closed,
    (c) does not form a double stranded structure longer than 100 base pairs,
    (d) is at least 200 nucleotides in length, and
    (e) does not comprise a protelomerase target sequence;
  wherein:
    (i) at least 95% by mass of total DNA in the composition is the ssDNA that is covalently closed;
    (ii) the pharmaceutical formulation is free of polypeptides;
    (iii) the therapeutic protein is expressed when the ssDNA is introduced into a target cell; and
    (iv) the ssDNA does not encode viral protein.

22. A pharmaceutical formulation comprising:
  an LNP comprising a single stranded DNA (ssDNA), wherein the ssDNA:
    (a) encodes a therapeutic protein,
    (b) is covalently closed,
    (c) does not comprise a region of intramolecular complementarity longer than 100 base pairs,
    (d) is at least 200 nucleotides in length, and
    (e) does not comprise a protelomerase target sequence;

wherein:
(i) at least 95% by mass of total DNA in the composition is the ssDNA that is covalently closed;
(ii) the pharmaceutical formulation is free of polypeptides;
(iii) the therapeutic protein is expressed when the ssDNA is introduced into a target cell;
(iv) the therapeutic protein is selected from the group consisting of: a transcription factor, a chromatin remodeling factor, an antigen, a peptide, a hormone, an enzyme, an antibody, a receptor ligand, a receptor, a clotting factor, and a membrane protein; and
(v) the ssDNA does not encode viral protein.

* * * * *

```
SEQUENCE LISTING

Sequence total quantity: 69
SEQ ID NO: 1            moltype = DNA  length = 21
FEATURE                 Location/Qualifiers
source                  1..21
                        mol_type = genomic DNA
                        organism = Simian virus 40
SEQUENCE: 1
cccaagaaga agaggaaagt c                                             21

SEQ ID NO: 2            moltype = DNA  length = 46
FEATURE                 Location/Qualifiers
source                  1..46
                        mol_type = genomic DNA
                        organism = Homo sapiens
SEQUENCE: 2
ctggggactt tccagcctgg ggactttcca gctgggactt tccagg                  46

SEQ ID NO: 3            moltype =   length =
SEQUENCE: 3
000

SEQ ID NO: 4            moltype = DNA  length = 72
FEATURE                 Location/Qualifiers
source                  1..72
                        mol_type = genomic DNA
                        organism = Homo sapiens
SEQUENCE: 4
ggtgtggaaa gtccccaggc tccccagcag gcagaagtat gcaaagcatg catctcaatt   60
agtcagcaac ca                                                       72

SEQ ID NO: 5            moltype = DNA  length = 336
FEATURE                 Location/Qualifiers
source                  1..336
                        mol_type = genomic DNA
                        organism = Homo sapiens
SEQUENCE: 5
cagggcagca ggggcaggtg ccagcaagga aggcaggcac gccaggaaga cacccatggt   60
gagaagtgca gatggcccga gggcaagttt gctcaactca cccaggtttg ctcttgctgg  120
ggccaagagg actcatgtgc cagggccaag ggcccttggg ggctctcaca gggggcttat  180
ctgggcttcg gttctggagg gccaggaaca aacaggcttc aaagccaagg gcttggctgg  240
cacacagggg gcttggtcct tcacctctgt cccctctccc tacggacaca tataagaccc  300
tggtcacacc tgggagagga ggagaggaga gcatag                            336

SEQ ID NO: 6            moltype = DNA  length = 36
FEATURE                 Location/Qualifiers
source                  1..36
                        mol_type = genomic DNA
                        organism = Homo sapiens
SEQUENCE: 6
ggctggtctt gaactcctgr gctcargtga tcctcc                             36

SEQ ID NO: 7            moltype =   length =
SEQUENCE: 7
000

SEQ ID NO: 8            moltype = DNA  length = 27
```

```
FEATURE              Location/Qualifiers
source               1..27
                     mol_type = genomic DNA
                     organism = Homo sapiens
SEQUENCE: 8
tgcggccaaa tctcccgcca ggtcagc                                           27

SEQ ID NO: 9         moltype = DNA  length = 27
FEATURE              Location/Qualifiers
source               1..27
                     mol_type = genomic DNA
                     organism = Homo sapiens
SEQUENCE: 9
gctgacctgg cgggagattt ggccgca                                           27

SEQ ID NO: 10        moltype = DNA  length = 32
FEATURE              Location/Qualifiers
source               1..32
                     mol_type = genomic DNA
                     organism = Homo sapiens
SEQUENCE: 10
aattctcctc cccaccttcc ccaccctccc ca                                     32

SEQ ID NO: 11        moltype =   length =
SEQUENCE: 11
000

SEQ ID NO: 12        moltype = DNA  length = 18
FEATURE              Location/Qualifiers
source               1..18
                     mol_type = genomic DNA
                     organism = Homo sapiens
SEQUENCE: 12
rnynncnngy ngktnyny                                                     18

SEQ ID NO: 13        moltype = DNA  length = 11
FEATURE              Location/Qualifiers
source               1..11
                     mol_type = genomic DNA
                     organism = Homo sapiens
SEQUENCE: 13
wtttatrttt w                                                            11

SEQ ID NO: 14        moltype = DNA  length = 404
FEATURE              Location/Qualifiers
source               1..404
                     mol_type = genomic DNA
                     organism = Homo sapiens
SEQUENCE: 14
aggcagaccc aggggccgca tgcagcaggg cctgaggagg gaggtgtgga cggaggaggc       60
ccgctgccat tcttggtatg gttctcactc caggagcaca gctgcatctg gtctcactct      120
gggcagctta taaggcctgg tgtgagtttt gtttatgcaa gtgcagcata aaaggaacaa      180
atctaccagc accggggctg ttgccactga gtccttttgc atacattttt caaatgataa      240
ctcactctac ccaccccct tccctacccc caaggcgatt tattgaaaaa accacctat        300
atggtaatat tgctaacaca ccgtcagctg gccttttag ggactttgtt taaagaagat       360
ccgcctctgg ggttttatat tgctctggta ttcatgccaa agac                       404

SEQ ID NO: 15        moltype =   length =
SEQUENCE: 15
000

SEQ ID NO: 16        moltype = DNA  length = 336
FEATURE              Location/Qualifiers
source               1..336
                     mol_type = genomic DNA
                     organism = Homo sapiens
SEQUENCE: 16
cagggcagca ggggcaggtg ccagcaagga aggcaggcac gccaggaaga cacccatggt       60
gagaagtgca gatggcccga gggcaagttt gctcaactca cccaggtttg ctcttgctgg      120
ggccaagagg actcatgtgc cagggccaag ggcccttggg ggctctcaca ggggcttat       180
ctgggcttcg gttctggagg gccaggaaca aacaggcttc aaagccaagg gcttggctgg     240
cacacagggg gcttggtcct tcacctctgt ccctctccc tacgacaca tataagaccc       300
tggtcacacc tgggagagga ggagaggaga gcatag                                336

SEQ ID NO: 17        moltype = DNA  length = 55
FEATURE              Location/Qualifiers
source               1..55
                     mol_type = genomic DNA
                     organism = Homo sapiens
```

```
SEQUENCE: 17
ggggactttc cggggacttt ccggggactt tccgggact ttccgggac ttttcc        55

SEQ ID NO: 18              moltype = DNA   length = 404
FEATURE                    Location/Qualifiers
source                     1..404
                           mol_type = genomic DNA
                           organism = Homo sapiens
SEQUENCE: 18
aggcagaccc aggggccgca tgcagcaggg cctgaggagg gaggtgtgga cggaggaggc    60
ccgctgccat tcttggtatg gttctcactc caggagcaca gctgcatctg gtctcactct   120
gggcagctta aaggcctgg tgtgagtttt gtttatgcaa gtgcagcata aaaggaacaa    180
atctaccagc accggggctg ttgccactga gtccttttgc atacattttt caaatgataa   240
ctcactctac ccacccccct tccctacccc caaggcgatt tattgaaaaa accaccttat   300
atggtaatat tgctaacaca ccgtcagctg gccttttag ggactttgtt taaagaagat    360
ccgcctctgg ggtttatat tgctctggta ttcatgccaa agac                     404

SEQ ID NO: 19              moltype = DNA   length = 176
FEATURE                    Location/Qualifiers
source                     1..176
                           mol_type = genomic DNA
                           organism = Homo sapiens
SEQUENCE: 19
ttcaaatgat aactcactct acccacccc cttccctacc cccaaggcga tttattgaaa    60
aaaccacctt atatggtaat attgctaaca caccgtcagc tggccttttt agggactttg   120
tttaaagaag atccgcctct ggggttttat attgctctgg tattcatgcc aaagac       176

SEQ ID NO: 20              moltype =    length =
SEQUENCE: 20
000

SEQ ID NO: 21              moltype = DNA   length = 336
FEATURE                    Location/Qualifiers
source                     1..336
                           mol_type = genomic DNA
                           organism = Homo sapiens
SEQUENCE: 21
cagggcagca ggggcaggtg ccagcaagga aggcaggcac gccaggaaga cacccatggt    60
gagaagtgca gatggcccga gggcaagttt gctcaactca cccaggtttg ctcttgctgg   120
ggccaagagg actcatgtgc cagggccaag ggcccttggg ggctctcaca ggggcttat    180
ctgggcttcg gttctggagg gccaggaaca aacaggcttc aaagcaagg gcttggctgg   240
cacacagggg gcttggtcct tcacctctgt cccctctccc tacggacaca tataagaccc   300
tggtcacacc tgggagagga ggagaggaga gcatag                             336

SEQ ID NO: 22              moltype = DNA   length = 404
FEATURE                    Location/Qualifiers
source                     1..404
                           mol_type = genomic DNA
                           organism = Homo sapiens
SEQUENCE: 22
aggcagaccc aggggccgca tgcagcaggg cctgaggagg gaggtgtgga cggaggaggc    60
ccgctgccat tcttggtatg gttctcactc caggagcaca gctgcatctg gtctcactct   120
gggcagctta aaggcctgg tgtgagtttt gtttatgcaa gtgcagcata aaaggaacaa    180
atctaccagc accggggctg ttgccactga gtccttttgc atacattttt caaatgataa   240
ctcactctac ccacccccct tccctacccc caaggcgatt tattgaaaaa accaccttat   300
atggtaatat tgctaacaca ccgtcagctg gccttttag ggactttgtt taaagaagat    360
ccgcctctgg ggtttatat tgctctggta ttcatgccaa agac                     404

SEQ ID NO: 23              moltype = DNA   length = 2186
FEATURE                    Location/Qualifiers
source                     1..2186
                           mol_type = genomic DNA
                           organism = Homo sapiens
SEQUENCE: 23
catgcaggaa aaggacaagc agcgaaaatt cacgcccct tgggaggtgg cggcatatgc     60
aaaggatagc actcccactc tactactggg tatcatatgc tgactgtata tgcatgagga   120
tagcatatgc taccccggata cagattagga tagcatatac tacccagata tagattagga   180
tagcatatgc tacccagata tagattagga tagcctatgc tacccagata taaattagga   240
tagcatatac tacccagata tagattagga tagcatatgc tacccagata tagattagga   300
tagcctatgc tacccagata tagattagga tagcatatgc tacccagata tagattagga   360
tagcatatgc tatccagata tttgggtagt atatgctacc cagatataaa ttaggatagc   420
atatactacc ctaatctcta ttaggatagc atatgctacc cggatacaga ttaggatagc   480
atatactacc cagatataga ttaggatagc atatgctacc cagatataga ttaggatagc   540
ctatgctacc cagatataaa ttaggatagc atatactacc cagatataga ttaggatagc   600
atatgctacc cagatataga ttaggatagc ctatgctacc cagatataga ttaggatagc   660
atatgctatc cagatatttg ggtagtatat gctacccatg gcaacattag cccaccgtgc   720
tctcagcgac ctcgtgaata tgaggaccaa caacctgtg cttggcgctc aggcgcaagt    780
gtgtgtaatt tgtcctccag atcgcagcaa tcgcgccct atcttggccc gcccacctac    840
ttatgcaggt attccccggg gtgccattag tggttttgtg ggcaagtggt ttgaccgcag   900
```

```
tggttagcgg ggttacaatc agccaagtta ttacacccct atttacagt ccaaaaccgc    960
agggcggcgt gtggggctg acgcgtgccc ccactccaca atttcaaaaa aaagagtggc   1020
cacttgtctt tgtttatggg ccccattggc gtggagcccc gtttaatttt cgggggtgtt   1080
agagacaacc agtggagtcc gctgctgtcg gcgtccactc tctttcccct tgttacaaat   1140
agagtgtaac aacatggttc acctgtcttg gtccctgcct gggacacatc ttaataaccc   1200
cagtatcata ttgcactagg attatgtgtt gcccatagcc ataaattcgt gtgagatgga   1260
catccagtct ttacggcttg tccccacccc atggatttct attgttaaag atattcagaa   1320
tgtttcattc ctacactagt atttattgcc caagggggttt tgagggtta tattggtgtc   1380
atagcacaat gccaccactg aaccccccgt ccaaatttta ttctggggc gtcacctgaa   1440
accttgtttt cgagcacctc acatacacct tactgttcac aactcagcag ttattctatt   1500
agctaaacga aggagaatga agaagcaggc gaagattcag gagagttcac tgcccgctcc   1560
tgatcttca gccactgccc ttgtgactaa aatggttcac tacccctcgtg aatcctgac   1620
cccatgtaaa taaaaccgtg acagctcatg gggtgggaga tatcgctgtt ccttaggacc   1680
cttttactaa ccctaattcg atagcatatg cttcccgttg ggtaacatat gctattgaat   1740
tagggttagt ctggatagta tatactacta cccgggaagc atatgctacc cgtttagggt   1800
taacaagggg gccttataaa cactattgct aatgccctct tgagggtccg cttatcggta   1860
gctacacagg ccccctctgat tgacgttggt gtagcctccc gtagtcttcc tgggcccctg   1920
ggaggtacat gtcccccagc attggtgtaa gagcttcagc caagagttac acataaaggc   1980
aatgttgtgt tgcagtccac agactgcaaa gtctgctcca ggatgaaagc cactcagtgt   2040
tggcaaatgt gcacatccat ttataaggat gtcaactaca gtcagagaac ccctttgtgt   2100
ttggtccccc ccgtgtcac atgtggaaca gggcccagtt ggcaagttgt accaaccaac   2160
tgaagggatt acatgcactg ccccgc                                      2186

SEQ ID NO: 24          moltype = DNA   length = 176
FEATURE                Location/Qualifiers
source                 1..176
                       mol_type = genomic DNA
                       organism = Homo sapiens
SEQUENCE: 24
ttcaaatgat aactcactct acccacccc cttccctacc cccaaggcga tttattgaaa     60
aaaccacctt atatggtaat attgctaaca caccgtcagc tggccttttt agggactttg   120
tttaaagaag atccgcctct ggggttttat attgctctgg tattcatgcc aaagac       176

SEQ ID NO: 25          moltype = DNA   length = 141
FEATURE                Location/Qualifiers
source                 1..141
                       mol_type = other DNA
                       organism = synthetic construct
SEQUENCE: 25
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca   120
actccatcac tagggggttcc t                                            141

SEQ ID NO: 26          moltype = DNA   length = 141
FEATURE                Location/Qualifiers
source                 1..141
                       mol_type = other DNA
                       organism = synthetic construct
SEQUENCE: 26
aggaacccct agtgatggag ttggccactc cctctctgcg cgctcgctcg ctcactgagg     60
ccgggcgacc aaaggtcgcc cgacgcccgg gctttgcccg gcggcctcag gtgagcgagc   120
gagcgcgcag ctgcctgcag g                                             141

SEQ ID NO: 27          moltype = DNA   length = 121
FEATURE                Location/Qualifiers
source                 1..121
                       mol_type = other DNA
                       organism = synthetic construct
SEQUENCE: 27
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca   120
a                                                                   121

SEQ ID NO: 28          moltype = DNA   length = 121
FEATURE                Location/Qualifiers
source                 1..121
                       mol_type = other DNA
                       organism = synthetic construct
SEQUENCE: 28
ttggccactc cctctctgcg cgctcgctcg ctcactgagg ccgggcgacc aaaggtcgcc     60
cgacgcccgg gctttgcccg gcggcctcag gtgagcgagc gagcgcgcag ctgcctgcag   120
g                                                                   121

SEQ ID NO: 29          moltype = DNA   length = 80
FEATURE                Location/Qualifiers
source                 1..80
                       mol_type = other DNA
                       organism = synthetic construct
SEQUENCE: 29
```

```
cccgagggcg ggtgccgaag gtgagtttac acaccgaagt caaggggcaa ttcgggctcg    60
ggactggccg ggctatgggc                                                80

SEQ ID NO: 30           moltype =    length =
SEQUENCE: 30
000

SEQ ID NO: 31           moltype =    length =
SEQUENCE: 31
000

SEQ ID NO: 32           moltype =    length =
SEQUENCE: 32
000

SEQ ID NO: 33           moltype =    length =
SEQUENCE: 33
000

SEQ ID NO: 34           moltype =    length =
SEQUENCE: 34
000

SEQ ID NO: 35           moltype =    length =
SEQUENCE: 35
000

SEQ ID NO: 36           moltype =    length =
SEQUENCE: 36
000

SEQ ID NO: 37           moltype = DNA   length = 1179
FEATURE                 Location/Qualifiers
source                  1..1179
                        mol_type = other DNA
                        organism = synthetic construct
SEQUENCE: 37
ggctccggtg cccgtcagtg ggcagagcgc acatcgccca cagtcccga gaagttgggg    60
ggaggggtcg gcaattgaac cggtgcctag agaaggtggc gcggggtaaa ctgggaaagt   120
gatgtcgtgt actggctccg cctttttccc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acgggttatg gcccttgcgt gccttgaatt   300
acttccacct ggctgcagta cgtgattctt gatcccgagc ttcgggttgg aagtgggtgg   360
gagagttcga ggccttgcgc ttaaggagcc ccttcgcctc gtgcttgagt tgaggcctgg   420
cctgggcgct ggggccgccg cgtgcgaatc tggtggcacc ttcgcgcctg tctcgctgct   480
ttcgataagt ctctagccat ttaaaatttt tgatgacctg ctgcgacgct ttttttctgg   540
caagatagtc ttgtaaatgc gggccaagat ctgcacactg gtatttcggt ttttggggcc   600
gcgggcggcg acggggcccg tgcgtcccag cgcacatgtt cggcgaggcg gggcctgcga   660
gcgcggccac cgagaatcgg acgggggtag tctcaagctg gccggcctgc tctggtgcct   720
ggcctcgcgc cgccgtgtat cgccccgccc tgggcggcaa ggctggccg gtcggcacca    780
gttgcgtgag cggaaagatg gccgcttccc ggccctgctc cagggagctc aaaatggagg   840
acgcggcgct cgggagagcg ggcgggtgag tcacccacac aaaggaaaag gccttttccg   900
tcctcagccg tcgcttcatg tgactccacg gagtaccggg cgccgtccag gcacctcgat   960
tagttctcga gcttttggag tacgtcgtct ttaggttggg gggagggggtt ttatgcgatg  1020
gagtttcccc acactgagtg ggtggagact gaagttaggc cagcttggca cttgatgtaa  1080
ttctccttgg aatttgcct ttttgagttt ggatctggt tcattctcaa gcctcagaca    1140
gtggttcaaa gtttttttct tccatttcag gtgtcgtga                         1179

SEQ ID NO: 38           moltype = DNA   length = 711
FEATURE                 Location/Qualifiers
source                  1..711
                        mol_type = other DNA
                        organism = synthetic construct
SEQUENCE: 38
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc ccctcagttc atgtacggct ccaaggccta cgtgaagcac   240
cccgccgaca tccccgacta cttgaagctg tccttcccg agggcttcaa gtgggagcgc    300
gtgatgaact tcgaggacgg cggcgtggtg accgtgaccc aggactcctc cctgcaggac   360
ggcgagttca tctacaaggt gaagctgcgc ggcaccaact cccctccga cggcccgta    420
atgcagaaga gaccatgggc tgggaggcc tcctccgagc ggatgtaccc cgaggacggc    480
gccctgaagg gcgagatcaa gcagaggctg aagctgaagg acggcggcca ctacgacgct   540
gaggtcaaga ccacctacaa ggcaagaag ccgtgcagc tgcccggcgc ctacaagtc      600
aacatcaagt tggacatcac ctcccacaac gaggactaca ccatcgtgga acagtacgaa   660
cgcgccgagg ccgcccactc caccggcggc atggacgagc tgtacaagta a            711

SEQ ID NO: 39           moltype = DNA   length = 156
FEATURE                 Location/Qualifiers
```

```
source                          1..156
                                mol_type = genomic DNA
                                organism = Homo sapiens
SEQUENCE: 39
tataattcac tggaattttt ttgtgtgtat ggtatgacat atgggttccc ttttattttt        60
tacatataaa tatatttccc tgttttctta aaaagaaaa agatcatcat tttcccattg        120
taaaatgcca tattttttc ataggtcact tacata                                  156

SEQ ID NO: 40                   moltype = DNA  length = 12
FEATURE                         Location/Qualifiers
source                          1..12
                                mol_type = other DNA
                                organism = synthetic construct
SEQUENCE: 40
ccgtggtcct tc                                                            12

SEQ ID NO: 41                   moltype = DNA  length = 24
FEATURE                         Location/Qualifiers
source                          1..24
                                mol_type = other DNA
                                organism = synthetic construct
SEQUENCE: 41
cttggattcc tacaaagaag cagc                                               24

SEQ ID NO: 42                   moltype = DNA  length = 22
FEATURE                         Location/Qualifiers
source                          1..22
                                mol_type = other DNA
                                organism = synthetic construct
SEQUENCE: 42
tcctccttct ggaactgctg ca                                                 22

SEQ ID NO: 43                   moltype = DNA  length = 22
FEATURE                         Location/Qualifiers
source                          1..22
                                mol_type = other DNA
                                organism = synthetic construct
SEQUENCE: 43
agacagccac tcacctcttc ag                                                 22

SEQ ID NO: 44                   moltype = DNA  length = 22
FEATURE                         Location/Qualifiers
source                          1..22
                                mol_type = other DNA
                                organism = synthetic construct
SEQUENCE: 44
ttctgccagt gcctctttgc tg                                                 22

SEQ ID NO: 45                   moltype = DNA  length = 22
FEATURE                         Location/Qualifiers
source                          1..22
                                mol_type = other DNA
                                organism = synthetic construct
SEQUENCE: 45
ccacagacct tccaggagaa tg                                                 22

SEQ ID NO: 46                   moltype = DNA  length = 23
FEATURE                         Location/Qualifiers
source                          1..23
                                mol_type = other DNA
                                organism = synthetic construct
SEQUENCE: 46
gtgcagttca gtgatcgtac agg                                                23

SEQ ID NO: 47                   moltype = DNA  length = 22
FEATURE                         Location/Qualifiers
source                          1..22
                                mol_type = other DNA
                                organism = synthetic construct
SEQUENCE: 47
ctcttctgcc tgctgcactt tg                                                 22

SEQ ID NO: 48                   moltype = DNA  length = 22
FEATURE                         Location/Qualifiers
source                          1..22
                                mol_type = other DNA
                                organism = synthetic construct
SEQUENCE: 48
atgggctaca ggcttgtcac tc                                                 22
```

```
SEQ ID NO: 49          moltype = DNA   length = 23
FEATURE                Location/Qualifiers
source                 1..23
                       mol_type = other DNA
                       organism = synthetic construct
SEQUENCE: 49
ggtgagaaga gatgtctgaa tcc                                             23

SEQ ID NO: 50          moltype = DNA   length = 22
FEATURE                Location/Qualifiers
source                 1..22
                       mol_type = other DNA
                       organism = synthetic construct
SEQUENCE: 50
gtccatcctt ggaagcactg ca                                              22

SEQ ID NO: 51          moltype = DNA   length = 23
FEATURE                Location/Qualifiers
source                 1..23
                       mol_type = other DNA
                       organism = synthetic construct
SEQUENCE: 51
aagttgtctg tgtgcgcaaa tcc                                             23

SEQ ID NO: 52          moltype = DNA   length = 24
FEATURE                Location/Qualifiers
source                 1..24
                       mol_type = other DNA
                       organism = synthetic construct
SEQUENCE: 52
ccattccaga aaagccacag tttt                                            24

SEQ ID NO: 53          moltype = DNA   length = 22
FEATURE                Location/Qualifiers
source                 1..22
                       mol_type = other DNA
                       organism = synthetic construct
SEQUENCE: 53
gtctcctctg acttcaacag cg                                              22

SEQ ID NO: 54          moltype = DNA   length = 22
FEATURE                Location/Qualifiers
source                 1..22
                       mol_type = other DNA
                       organism = synthetic construct
SEQUENCE: 54
accaccctgt tgctgtagcc aa                                              22

SEQ ID NO: 55          moltype = DNA   length = 2191
FEATURE                Location/Qualifiers
source                 1..2191
                       mol_type = other DNA
                       organism = synthetic construct
SEQUENCE: 55
ccttcgagac cggctccggt gcccgtcagt gggcagagcg cacatcgccc acagtccccg       60
agaagttggg gggaggggtc ggcaattgaa ccggtgccta gagaaggtgg gcgcggggtaa     120
actgggaaag tgatgtcgtg tactggctcc gccttttttcc cgagggtggg ggagaaccgt     180
atataagtgc agtagtcgcc gtgaacgttc ttttttcgcaa cgggtttgcc gccagaacac     240
aggtaagtgc cgtgtgtggt tcccgcgggc ctggcctctt tacgggttat ggccttgcg      300
tgccttgaat tacttccacc tggctgcagt acgtcgattct tgatcccgag cttcgggttg     360
gaagtgggtg ggagagttcg aggccttgcg cttaaggagc cccttcgcct cgtgcttgag     420
ttgaggcctg gcctgggcgc tggggccgcc gcgtgcgaat ctggtggcac cttcgcgcct     480
gtctcgctgc tttcgataag tctctagcca tttaaatttt ttgatgacct gctgcgacgc     540
ttttttttctg gcaagatagt cttgtaaatg cgggccaaga tctgcacact ggtatttcgg     600
tttttggggc cgcggggcgg cgacggggccc gtgcgtccca gcgcacatgt tcggcgaggc     660
ggggcctgcg agcgcggcca ccgagaatcg gacgggggta gtctcaagct ggccggcctg     720
ctctggtgcc tggcctcgcg ccgccgtgta tcgccccgcc ctgggcggca aggctggccc     780
ggtcggcacc agttgcgtga gcggaaagat ggccgcttcc cgcccctgct gcaggggagct    840
caaaatggag gacgcggcgc tcgggagagc gggcgggtga gtcacccaca caaaggaaaa     900
gggcctttcc gtcctcagcc gtcgcttcat gtgactccac ggagtaccgg gcgccgtcca     960
ggcacctcga ttagttctcg agcttttgga gtacgtcgtc tttaggttgg ggggaggggt    1020
tttatgcgat ggagtttccc cacactgagt gggtggagac tgaagttagg ccagcttggc    1080
acttgatgta attctcccttg gaattttgccc ttttttgagtt tggatcttgg ttcattctca   1140
agcctcagac agtggttcaa agttttttttc ttccatttca ggtgtcgtga ggatccgcca    1200
ccatggtgag caaggggcag gaggataaca tggccatcat caaggagttc atgcgcttca    1260
aggtgcacat ggagggctcc gtgaacggcc acgagttcga gatcgagggc gagggcgagg    1320
ccgccccta cgagggcacc cagaccgcca agctgaaggt gaccaagggt ggccccctgc    1380
ccttcgcctg ggacatcctg tcccctcagt tcatgtacgg ctccaaggcc tacgtgaagc    1440
```

```
accccgccga catccccgac tacttgaagc tgtccttccc cgagggcttc aagtgggagc    1500
gcgtgatgaa cttcgaggac ggcggcgtgg tgaccgtgac ccaggactcc tccctgcagg    1560
acggcgagtt catctacaag gtgaagctgc gcggcaccaa cttcccctcc gacgcccccg    1620
taatgcagaa gaagaccatg ggctgggagg cctcctccga gcggatgtac cccgaggacg    1680
gcgccctgaa gggcgagatc aagcagaggc tgaagctgaa ggacggcggc cactacgacg    1740
ctgaggtcaa gaccacctac aaggccaaga agcccgtgca gctgcccggc gcctacaacg    1800
tcaacatcaa gttggacatc acctcccaca acgaggacta caccatcgtg aacagtacg     1860
aacgcgccga gggccgccac tccaccggcg gcatggacga gctgtacaag taagtttaaa    1920
cccgctgatc agcctcgact gtgccttcta gttgccagcc atctgttgtt tgcccctccc    1980
ccgtgccttc cttgaccctg gaaggtgcca ctcccactgt cctttcctaa taaaatgagg    2040
aaattgcatc gcattgtctg agtaggtgtc attctattct gggggtgggg gtggggcagg    2100
acagcaaggg ggaggattgg gaagacaata gcaggcatgc tggggatgcg gtgggctcta    2160
tggctgcaat ggctcttcat ctgaggtctc g                                   2191

SEQ ID NO: 56           moltype = DNA   length = 11
FEATURE                 Location/Qualifiers
source                  1..11
                        mol_type = genomic DNA
                        organism = Homo sapiens
SEQUENCE: 56
ggggactttc c                                                         11

SEQ ID NO: 57           moltype = DNA   length = 106
FEATURE                 Location/Qualifiers
source                  1..106
                        mol_type = other DNA
                        organism = synthetic construct
SEQUENCE: 57
ccttcgagac cggctccggt gcccgtcagt gggcagagcg cacatcgccc acagtccccg    60
agaagttggg gggaggggtc ggcaattgaa ccggtgccta gagaag                   106

SEQ ID NO: 58           moltype = DNA   length = 264
FEATURE                 Location/Qualifiers
source                  1..264
                        mol_type = other DNA
                        organism = synthetic construct
SEQUENCE: 58
gtggcgcggg gtaaactggg aaagtgatgt cgtgtactgg ctccgccttt tccccgaggg    60
tgggggagaa ccgtatataa gtgcagtagt cgccgtgaac gttcttttc gcaacgggtt     120
tgccgccaga acacaggtaa gtgccgtgtg tggttcccgc gggcctggcc tctttacggg    180
ttatggcct tgcgtgcctt gaattacttc cacctggctg cagtacgtga ttcttgatcc     240
cgagcttcgg gttggaagtg ggtg                                           264

SEQ ID NO: 59           moltype = DNA   length = 355
FEATURE                 Location/Qualifiers
source                  1..355
                        mol_type = other DNA
                        organism = synthetic construct
SEQUENCE: 59
ggagagttcg aggccttgcg cttaaggagc cccttcgcct cgtgcttgag ttgaggcctg    60
gcctgggcgc tggggccgcc gcgtgcgaat ctggtgcgca cttcgcgcct gtctcgctgc    120
tttcgataag tctctagcca tttaaaattt ttgatgacct gctgcgacgc ttttttttctg   180
gcaagatagt cttgtaaatg cgggccaaga tctgcacact ggtatttcgg tttttggggc    240
cgcgggcggc gacggggccc gtgcgtccca gcgcacatgt tcggcgaggc ggggcctgcg    300
agcgcggcca ccgagaatcg gacggggta gtctcaagct ggccggcctg ctctg          355

SEQ ID NO: 60           moltype = DNA   length = 64
FEATURE                 Location/Qualifiers
source                  1..64
                        mol_type = other DNA
                        organism = synthetic construct
SEQUENCE: 60
gtgcctggcc tcgcgccgcc gtgtatcgcc ccgccctggg cggcaaggct ggcccggtcg    60
gcac                                                                 64

SEQ ID NO: 61           moltype = DNA   length = 13
FEATURE                 Location/Qualifiers
source                  1..13
                        mol_type = other DNA
                        organism = synthetic construct
SEQUENCE: 61
cagttgcgtg agc                                                       13

SEQ ID NO: 62           moltype = DNA   length = 12
FEATURE                 Location/Qualifiers
source                  1..12
                        mol_type = other DNA
                        organism = synthetic construct
SEQUENCE: 62
```

```
ggaaagatgg cc                                                            12

SEQ ID NO: 63               moltype = DNA   length = 19
FEATURE                     Location/Qualifiers
source                      1..19
                            mol_type = other DNA
                            organism = synthetic construct
SEQUENCE: 63
gcttcccggc cctgctgca                                                     19

SEQ ID NO: 64               moltype = DNA   length = 790
FEATURE                     Location/Qualifiers
source                      1..790
                            mol_type = other DNA
                            organism = synthetic construct
SEQUENCE: 64
gggagctcaa aatggaggac gcggcgctcg ggagagcggg cgggtgagtc acccacacaa         60
aggaaaaggg cctttccgtc ctcagccgtc gcttcatgtg actccacgga gtaccgggcg        120
ccgtccaggc acctcgatta gttctcgagc ttttggagta cgtcgtcttt aggttggggg        180
gagggggtttt atgcgatgga gtttccccac actgagtggg tggagactga agttaggcca      240
gcttggcact tgatgtaatt ctccttggaa tttgcccttt ttgagtttgg atcttggttc       300
attctcaagc ctcagacagt ggttcaaagt ttttttcttc catttcaggt gtcgtgagga       360
tccgccacca tggtgagcaa gggcgaggag gataacatgg ccatcatcaa ggagttcatg       420
cgcttcaagg tgcacatgga gggctccgtg aacggccacg agttcgagat cgagggcgag      480
ggcgagggcc gcccctacga gggcacccag accgccaagc tgaaggtgac caagggtggc      540
ccccctgccct tcgcctggga catcctgtcc cctcagttca tgtacggctc caaggcctac      600
gtgaagcacc ccgccgacat ccccgactac ttgaagctgt ccttccccga gggcttcaag       660
tgggagcgcg tgatgaactt cgaggacggc ggcgtggtga ccgtgaccca ggactcctcc      720
ctgcaggacg gcgagttcat ctacaaggtg aagctgcgcg gcaccaactt cccctccgac      780
ggccccgtaa                                                             790

SEQ ID NO: 65               moltype = DNA   length = 130
FEATURE                     Location/Qualifiers
source                      1..130
                            mol_type = other DNA
                            organism = synthetic construct
SEQUENCE: 65
tgcagaagaa gaccatgggc tgggaggcct cctccgagcg gatgtacccc gaggacggcg       60
ccctgaaggg cgagatcaag cagaggctga agctgaagga cggcggccac tacgacgctg      120
aggtcaagac                                                             130

SEQ ID NO: 66               moltype = DNA   length = 191
FEATURE                     Location/Qualifiers
source                      1..191
                            mol_type = other DNA
                            organism = synthetic construct
SEQUENCE: 66
cacctacaag gccaagaagc ccgtgcagct gcccggcgcc tacaacgtca acatcaagtt        60
ggacatcacc tccacaacg aggactacac catcgtggaa cagtacgaac gcgccgaggg       120
ccgccactcc accggcggca tggacgagct gtacaagtaa gtttaaaccc gctgatcagc      180
ctcgactgtg c                                                           191

SEQ ID NO: 67               moltype = DNA   length = 247
FEATURE                     Location/Qualifiers
source                      1..247
                            mol_type = other DNA
                            organism = synthetic construct
SEQUENCE: 67
cttctagttg ccagccatct gttgtttgcc cctcccccgt gccttccttg accctggaag       60
gtgccactcc cactgtcctt tcctaataaa atgaggaaat tgcatcgcat tgtctgagta      120
ggtgtcattc tattctgggg ggtgggggtgg ggcaggacag caaggggggag gattgggaag    180
acaatagcag gcatgctggg gatgcggtgg gctctatggc tgcaatggct cttcatctga      240
ggtctcg                                                                247

SEQ ID NO: 68               moltype = DNA   length = 354
FEATURE                     Location/Qualifiers
source                      1..354
                            mol_type = other DNA
                            organism = synthetic construct
SEQUENCE: 68
ggagagttcg aggccttgcg cttaaggagc cccttcgcct cgtgcttgag ttgaggcctg       60
gcctgggcgc tggggccgcc gcgtgcgaat ctggtggcac cttcgcgcct gtctcgctgc     120
tttcgataag tctctagcca tttaaaattt ttgatgacct gctgcgacgc ttttttttctg    180
gcaagatagt cttgtaaatg cgggccaaga tctgcacact ggtatttcgg ttttttgggc     240
cgcgggcggc gacggggccc gtgcgtccca gcgcacatgt tcggcgaggc ggggcctgcg     300
agcgcggcca ccgagaatcg gacggggggta gtctccaagct ggccgcctgc tctg          354

SEQ ID NO: 69               moltype = DNA   length = 18
FEATURE                     Location/Qualifiers
```

```
source          1..18
                mol_type = other DNA
                organism = synthetic construct
SEQUENCE: 69
gcttccggcc ctgctgca                                                    18
```